United States Patent
Py et al.

(10) Patent No.: US 9,637,251 B2
(45) Date of Patent: May 2, 2017

(54) SEALED CONTAINERS AND METHODS OF FILLING AND RESEALING SAME

(71) Applicant: MedInstill Development LLC, New Milford, CT (US)

(72) Inventors: Daniel Py, Larchmont, NY (US); Norbert M. Assion, Shelton, CT (US)

(73) Assignee: MEDINSTILL DEVELOPMENT LLC, New Milford, CT (US)

( * ) Notice: Subject to any disclaimer, the term of this patent is extended or adjusted under 35 U.S.C. 154(b) by 142 days.

(21) Appl. No.: 14/610,016

(22) Filed: Jan. 30, 2015

(65) Prior Publication Data

US 2015/0225094 A1    Aug. 13, 2015

Related U.S. Application Data

(60) Division of application No. 13/193,662, filed on Jul. 29, 2011, now Pat. No. 8,960,242, which is a
(Continued)

(51) Int. Cl.
*B65B 3/00* (2006.01)
*A61J 1/14* (2006.01)
(Continued)

(52) U.S. Cl.
CPC ............. *B65B 3/003* (2013.01); *A61J 1/1406* (2013.01); *A61J 1/1412* (2013.01); *A61J 1/1425* (2015.05);
(Continued)

(58) Field of Classification Search
CPC ......... B65B 3/003; B65B 3/027; B65B 7/161; B65B 51/10; B65B 55/08;
(Continued)

(56) References Cited

U.S. PATENT DOCUMENTS 2,061,958 A   11/1936   Chapman
2,191,447 A    2/1940   Beardsley
(Continued)

FOREIGN PATENT DOCUMENTS

CA          1123792 A1    5/1982
DE         086 14 068     6/1986
(Continued)

OTHER PUBLICATIONS

Office Action Issued Sep. 13, 2016 for Japanese Patent Application JP 2014-255545. 3 pages.
(Continued)

*Primary Examiner* — Timothy L Maust
(74) *Attorney, Agent, or Firm* — McCarter & English, LLP

(57) ABSTRACT

A container and method for filling same. The container includes a penetrable and resealable portion that is resealable, and a container body having a sealed empty chamber in fluid communication with the penetrable and resealable portion for receiving therein a substance. The container also includes a base, a mid-portion, and an upper portion axially spaced from the base on an opposite side of the mid-portion relative to the base. Each of the base and upper portion define a laterally-extending dimension greater than a maximum laterally-extending dimension of the mid-portion. The method of filling the container includes penetrating the penetrable and resealable portion with an injection member and introducing a substance into the chamber, withdrawing the injection member while engaging the base of the body to substantially prevent upward movement of the body, and applying energy to the penetrable and resealable portion to form a gas-tight seal.

17 Claims, 41 Drawing Sheets

Related U.S. Application Data continuation of application No. 12/791,629, filed on Jun. 1, 2010, now Pat. No. 7,992,597, which is a division of application No. 11/515,162, filed on Sep. 1, 2006, now Pat. No. 7,726,352, which is a continuation of application No. 10/655,455, filed on Sep. 3, 2003, now Pat. No. 7,100,646, which is a continuation-in-part of application No. 10/393,966, filed on Mar. 21, 2003, now Pat. No. 6,684,916, which is a division of application No. 09/781,846, filed on Feb. 12, 2001, now Pat. No. 6,604,561.

(60) Provisional application No. 60/182,139, filed on Feb. 11, 2000, provisional application No. 60/408,068, filed on Sep. 3, 2002.

(51) Int. Cl.
| | | |
|---|---|---|
| *A61J 1/18* | (2006.01) | |
| *B65B 7/16* | (2006.01) | |
| *B65D 51/00* | (2006.01) | |
| *B65B 3/02* | (2006.01) | |
| *B65B 51/10* | (2006.01) | |
| *B65B 55/08* | (2006.01) | |
| *A61J 1/20* | (2006.01) | |
| *B65B 39/00* | (2006.01) | |

(52) U.S. Cl.
CPC .............. *A61J 1/1431* (2015.05); *A61J 1/18* (2013.01); *B65B 3/027* (2013.01); *B65B 7/161* (2013.01); *B65B 51/10* (2013.01); *B65B 55/08* (2013.01); *B65D 51/002* (2013.01); *A61J 1/1468* (2015.05); *A61J 1/201* (2015.05); *A61J 1/2013* (2015.05); *A61J 1/2055* (2015.05); *A61J 1/2075* (2015.05); *A61J 1/2096* (2013.01); *A61M 2207/00* (2013.01); *A61M 2209/045* (2013.01); *B65B 2039/009* (2013.01)

(58) Field of Classification Search
CPC . B65B 2039/009; A61J 1/1406; A61J 1/1412; A61J 1/18; A61J 1/2096; A61J 1/201; A61J 1/2055; A61J 1/1425; A61J 1/2075; A61J 1/1431; A61J 1/1468; A61J 1/2013; B65D 51/002; A61M 2207/00; A61M 2209/045
USPC .............. 141/11, 69, 82, 329; 215/247–249; 220/363; 604/411–415; 435/300.1–301.1
See application file for complete search history.

(56) References Cited

U.S. PATENT DOCUMENTS

| | | |
|---|---|---|
| 2,503,147 A | 4/1950 | Applezweig |
| 2,667,986 A | 2/1954 | Perelson |
| 2,734,649 A | 2/1956 | Callahan et al. |
| 2,797,837 A | 7/1957 | Buford |
| 2,804,224 A | 8/1957 | Barton |
| 2,842,276 A | 7/1958 | Butler |
| 2,876,775 A | 3/1959 | Barr, Sr. et al. |
| 3,092,278 A | 6/1963 | Jarnhall |
| 3,136,440 A | 6/1964 | Krug et al. |
| 3,193,128 A | 7/1965 | Ravn |
| 3,278,063 A | 10/1966 | Kranzhoff |
| 3,340,671 A | 9/1967 | Loo |
| 3,358,865 A | 12/1967 | Andersen |
| 3,392,859 A | 7/1968 | Fischer |
| 3,424,329 A | 1/1969 | Herschberg et al. |
| 3,480,171 A | 11/1969 | Rohde |
| 3,637,102 A | 1/1972 | Shaw |
| 3,685,248 A | 8/1972 | Godelaine |
| 3,792,794 A | 2/1974 | Cutter et al. |
| 3,811,591 A | 5/1974 | Novitch |
| 3,826,059 A | 7/1974 | Novitch |
| 3,875,012 A | 4/1975 | Dorn et al. |
| 3,911,640 A | 10/1975 | Rausing |
| 4,041,994 A | 8/1977 | Horwitz et al. |
| 4,048,255 A | 9/1977 | Hillier et al. |
| 4,079,850 A | 3/1978 | Suzuki et al. |
| 4,134,300 A | 1/1979 | Svensson |
| 4,205,754 A | 6/1980 | Nielsen et al. |
| 4,208,852 A | 6/1980 | Pioch |
| 4,235,725 A | 11/1980 | Semersky |
| 4,250,611 A | 2/1981 | Wong |
| 4,251,003 A | 2/1981 | Bodenmann |
| 4,265,364 A | 5/1981 | Baba |
| 4,358,539 A | 11/1982 | Bittings |
| 4,364,485 A | 12/1982 | Knapp |
| 4,366,912 A | 1/1983 | Matukura et al. |
| 4,390,111 A | 6/1983 | Robbins et al. |
| 4,401,423 A | 8/1983 | Bellehache et al. |
| 4,444,330 A | 4/1984 | Kasai et al. |
| 4,456,138 A | 6/1984 | Bereziat |
| 4,471,879 A | 9/1984 | Connor et al. |
| 4,482,071 A | 11/1984 | Ishiwatari |
| 4,499,148 A | 2/1985 | Goodale et al. |
| 4,514,248 A | 4/1985 | Cummings |
| D279,651 S | 7/1985 | Freeman |
| 4,543,770 A | 10/1985 | Walter et al. |
| 4,628,969 A | 12/1986 | Jurgens, Jr. et al. |
| 4,635,807 A | 1/1987 | Knapp |
| 4,664,275 A | 5/1987 | Kasai et al. |
| 4,664,277 A | 5/1987 | Connor |
| 4,682,703 A | 7/1987 | Kasai et al. |
| 4,703,781 A | 11/1987 | Meyer et al. |
| 4,815,619 A | 3/1989 | Turner et al. |
| 4,834,152 A | 5/1989 | Howson et al. |
| 4,842,028 A | 6/1989 | Kaufman et al. |
| 4,863,453 A | 9/1989 | Berger et al. |
| 4,910,435 A | 3/1990 | Wakalopulos |
| 4,968,625 A | 11/1990 | Smith et al. |
| 5,000,804 A | 3/1991 | Nugent |
| 5,009,654 A | 4/1991 | Minshall et al. |
| 5,031,675 A | 7/1991 | Lindgren |
| 5,037,597 A | 8/1991 | McGinley et al. |
| 5,038,839 A | 8/1991 | Morimoto et al. |
| 5,067,532 A | 11/1991 | Lang et al. |
| 5,085,332 A | 2/1992 | Gettig et al. |
| 5,088,612 A | 2/1992 | Storar et al. |
| 5,088,995 A | 2/1992 | Packard et al. |
| 5,129,212 A | 7/1992 | Duffey et al. |
| 5,226,462 A | 7/1993 | Carl |
| 5,247,015 A | 9/1993 | Bayan |
| 5,341,854 A | 8/1994 | Zezulka et al. |
| 5,344,036 A | 9/1994 | Stanescu et al. |
| 5,353,573 A | 10/1994 | Durrant |
| 5,379,908 A | 1/1995 | Rohe |
| 5,390,469 A | 2/1995 | Shimizu et al. |
| 5,411,065 A | 5/1995 | Meador et al. |
| 5,414,267 A | 5/1995 | Wakalopulos |
| 5,431,201 A | 7/1995 | Torchia et al. |
| 5,464,111 A | 11/1995 | Vacek et al. |
| 5,484,566 A | 1/1996 | Gabbard |
| 5,496,302 A | 3/1996 | Minshall et al. |
| RE35,203 E | 4/1996 | Wakalopulos |
| 5,514,339 A | 5/1996 | Leopardi et al. |
| 5,549,141 A | 8/1996 | Meador et al. |
| 5,597,530 A | 1/1997 | Smith et al. |
| 5,601,214 A | 2/1997 | Hendrickson et al. |
| 5,612,588 A | 3/1997 | Wakalopulos |
| 5,641,004 A | 6/1997 | Py |
| 5,656,112 A | 8/1997 | Kuroda |
| D383,214 S | 9/1997 | Brennan |
| 5,669,208 A | 9/1997 | Tabaroni et al. |
| 5,673,535 A | 10/1997 | Jagger |
| 5,687,542 A | 11/1997 | Lawecki et al. |
| 5,702,019 A | 12/1997 | Grimard |
| D389,586 S | 1/1998 | Brennan |
| 5,718,334 A | 2/1998 | Demel |
| 5,718,348 A | 2/1998 | Manera |
| 5,744,082 A | 4/1998 | Bak |

(56) References Cited

U.S. PATENT DOCUMENTS

| | | |
|---|---|---|
| 5,744,087 A | 4/1998 | Williams et al. |
| 5,791,385 A | 8/1998 | Stahlecker |
| 5,803,284 A | 9/1998 | Grimard |
| 5,816,772 A | 10/1998 | Py |
| 5,823,373 A | 10/1998 | Sudo et al. |
| 5,829,594 A | 11/1998 | Warder |
| 5,842,321 A | 12/1998 | Jones |
| 5,902,298 A | 5/1999 | Niedospial, Jr. et al. |
| 5,904,677 A | 5/1999 | Drummey et al. |
| 5,909,032 A | 6/1999 | Wakalopulos |
| 5,931,828 A | 8/1999 | Durkee |
| 5,971,181 A | 10/1999 | Niedospial, Jr. et al. |
| 6,006,932 A | 12/1999 | Morini |
| 6,021,824 A | 2/2000 | Larsen et al. |
| 6,050,435 A | 4/2000 | Bush et al. |
| 6,065,270 A | 5/2000 | Reinhard et al. |
| 6,068,150 A | 5/2000 | Mitchell et al. |
| 6,070,748 A | 6/2000 | Storar |
| 6,094,890 A | 8/2000 | Michellon et al. |
| 6,095,355 A | 8/2000 | Jessen et al. |
| 6,096,358 A | 8/2000 | Murdick et al. |
| 6,119,433 A | 9/2000 | Kitahora et al. |
| 6,134,866 A | 10/2000 | Schoenewolff et al. |
| 6,140,657 A | 10/2000 | Wakalopulos et al. |
| 6,145,277 A | 11/2000 | Lawecki et al. |
| 6,145,688 A | 11/2000 | Smith |
| 6,156,842 A | 12/2000 | Hoenig et al. |
| 6,164,044 A | 12/2000 | Porfano et al. |
| 6,165,402 A | 12/2000 | Gabbard et al. |
| 6,168,037 B1 | 1/2001 | Grimard |
| 6,189,292 B1 | 2/2001 | Odell et al. |
| D439,345 S | 3/2001 | Herchenbach et al. |
| 6,199,350 B1 | 3/2001 | Brechel et al. |
| 6,223,918 B1 | 5/2001 | Browne |
| 6,234,335 B1 | 5/2001 | Gee et al. |
| 6,263,641 B1 | 7/2001 | Odell et al. |
| 6,269,976 B1 | 8/2001 | DeJonge |
| 6,277,331 B1 | 8/2001 | Konrad |
| 6,308,494 B1 | 10/2001 | Yuyama et al. |
| 6,308,847 B1 | 10/2001 | Andersson et al. |
| RE37,471 E | 12/2001 | Jagger |
| 6,326,010 B1 | 12/2001 | Sano et al. |
| 6,343,711 B1 | 2/2002 | Coughlin |
| 6,361,505 B1 | 3/2002 | Rainen et al. |
| RE37,676 E | 4/2002 | Abrams et al. |
| 6,364,864 B1 | 4/2002 | Mohiuddin et al. |
| 6,382,441 B1 | 5/2002 | Carano |
| 6,385,943 B2 | 5/2002 | Yuyama et al. |
| 6,475,435 B1 | 11/2002 | Taggart |
| 6,536,188 B1 | 3/2003 | Taggart |
| 6,568,439 B1 | 5/2003 | Se et al. |
| 6,604,561 B2 | 8/2003 | Py |
| 6,622,457 B2 | 9/2003 | Kurth |
| 6,681,475 B2 | 1/2004 | Thibault et al. |
| 6,702,133 B1 | 3/2004 | Shenkar et al. |
| 6,779,318 B2 | 8/2004 | Wang |
| 6,866,158 B1 | 3/2005 | Sommer et al. |
| 6,929,040 B2 | 8/2005 | Py |
| 7,032,631 B2 | 4/2006 | Py |
| 7,096,896 B2 | 8/2006 | Py |
| 7,100,646 B2 | 9/2006 | Py et al. |
| 7,111,649 B2 | 9/2006 | Py |
| 7,168,149 B2 | 1/2007 | Kalemba et al. |
| 7,243,689 B2 | 7/2007 | Py |
| 7,270,158 B2 | 9/2007 | Py |
| 7,556,066 B2 | 7/2009 | Py |
| 7,677,403 B2 | 3/2010 | Innocenti |
| 2001/0010145 A1 | 8/2001 | Tawa et al. |
| 2001/0041872 A1 | 11/2001 | Paul, Jr. |
| 2002/0006353 A1 | 1/2002 | Bilstad et al. |
| 2002/0010995 A1 | 1/2002 | Thibault et al. |
| 2002/0018731 A1 | 2/2002 | Bilstad et al. |
| 2002/0023409 A1 | 2/2002 | Py |
| 2002/0023893 A1 | 2/2002 | Sudo et al. |
| 2002/0029022 A1 | 3/2002 | Naritomi et al. |
| 2002/0131902 A1 | 9/2002 | Levy |
| 2002/0171179 A1 | 11/2002 | Dundas et al. |
| 2002/0172615 A1 | 11/2002 | Woodworth et al. |
| 2003/0098286 A1 | 5/2003 | Bloom et al. |
| 2003/0156973 A1 | 8/2003 | Bilstad et al. |
| 2003/0159750 A1 | 8/2003 | Py |
| 2004/0256026 A1 | 12/2004 | Py |
| 2005/0217211 A1 | 10/2005 | Py |
| 2005/0223677 A1 | 10/2005 | Py |
| 2006/0200968 A1 | 9/2006 | Thilly et al. |

FOREIGN PATENT DOCUMENTS

| | | |
|---|---|---|
| DE | 295 15 681 U1 | 12/1995 |
| EP | 0 480 196 A1 | 4/1992 |
| EP | 0 564 037 A1 | 10/1993 |
| EP | 0 921 151 B1 | 10/2001 |
| FR | 2 509 689 A1 | 1/1983 |
| GB | 500534 A | 2/1939 |
| GB | 984149 A | 2/1965 |
| GB | 2091229 B | 4/1984 |
| GB | 2364700 B | 6/2002 |
| JP | Sho 55-154025 U | 4/1954 |
| JP | S35-11080 | 5/1960 |
| JP | S62-194521 U | 12/1987 |
| JP | 03-140231 A | 6/1991 |
| JP | 05-016659 U | 3/1993 |
| JP | 07-034858 U | 8/1995 |
| JP | 8238301 A | 9/1996 |
| JP | H 09-502906 A | 3/1997 |
| JP | 10-234819 A | 9/1998 |
| JP | H 11-079227 A | 3/1999 |
| JP | 2934777 B2 | 8/1999 |
| JP | 2001-500824 A | 1/2001 |
| JP | 2001245958 A | 9/2001 |
| JP | 2005-535533 A | 11/2005 |
| WO | WO-95/34381 A3 | 4/1996 |
| WO | 0115984 A1 | 3/2001 |
| WO | WO-02/46043 A1 | 6/2002 |
| WO | WO-02/064439 A1 | 8/2002 |
| WO | WO-02/049821 A3 | 11/2002 |
| WO | WO-03/022313 A3 | 6/2003 |
| WO | WO-2004/000100 A3 | 4/2004 |
| WO | WO-2004/014778 A3 | 9/2004 |

OTHER PUBLICATIONS

Japanese Notice of Allowance issued on Jul. 7, 2015, for Japanese Patent Application No. 2013-118175. 2 pages.

Supplementary European Search Report mailed Jan. 4, 2010 in European Application No. 03 79 7876.

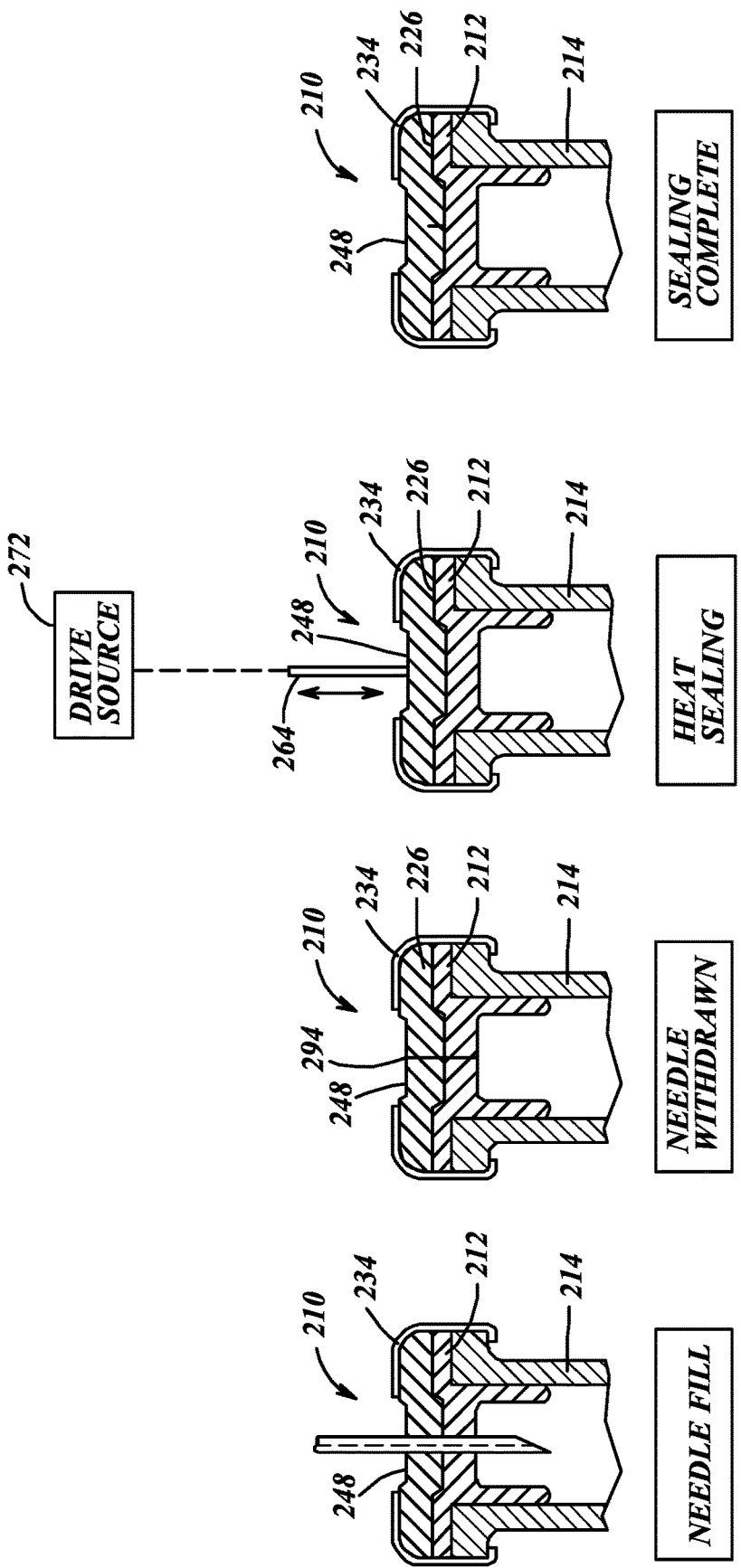

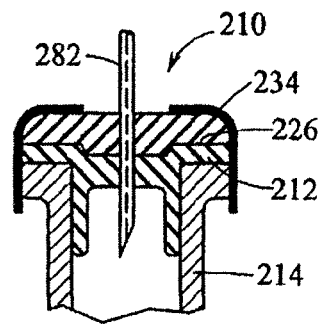
FIG. 13A
NEEDLE FILL
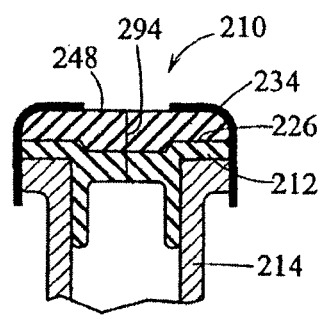
FIG. 13B
NEEDLE WITHDRAWN
FIG. 13C
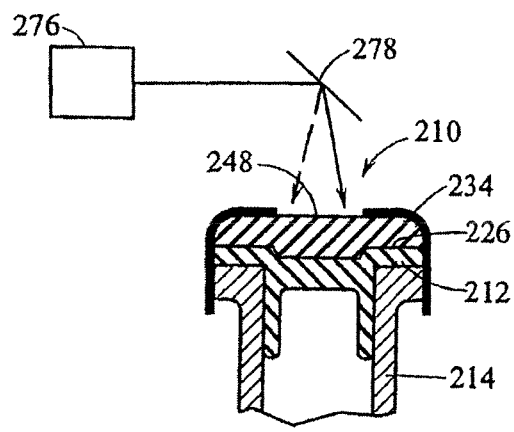
HEAT SEALING

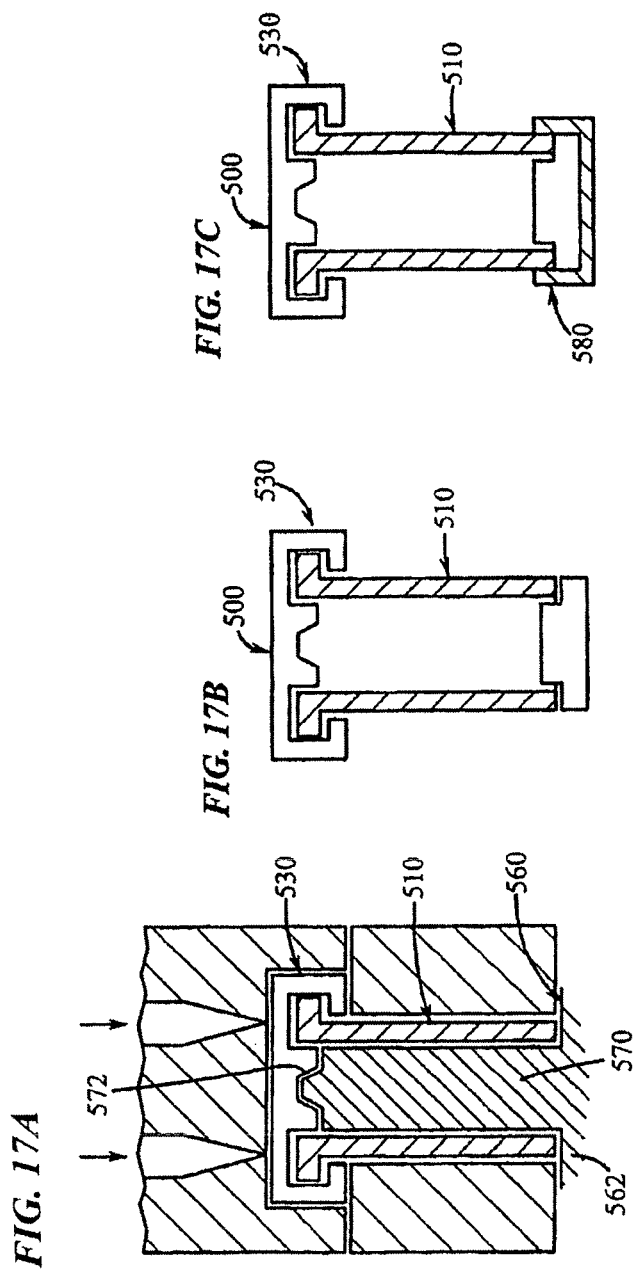

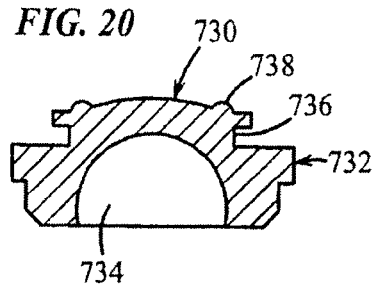
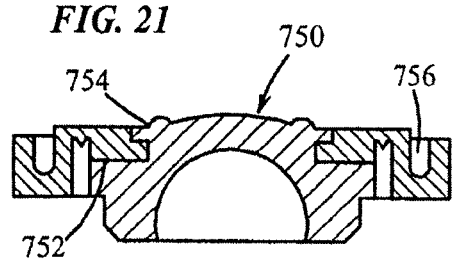

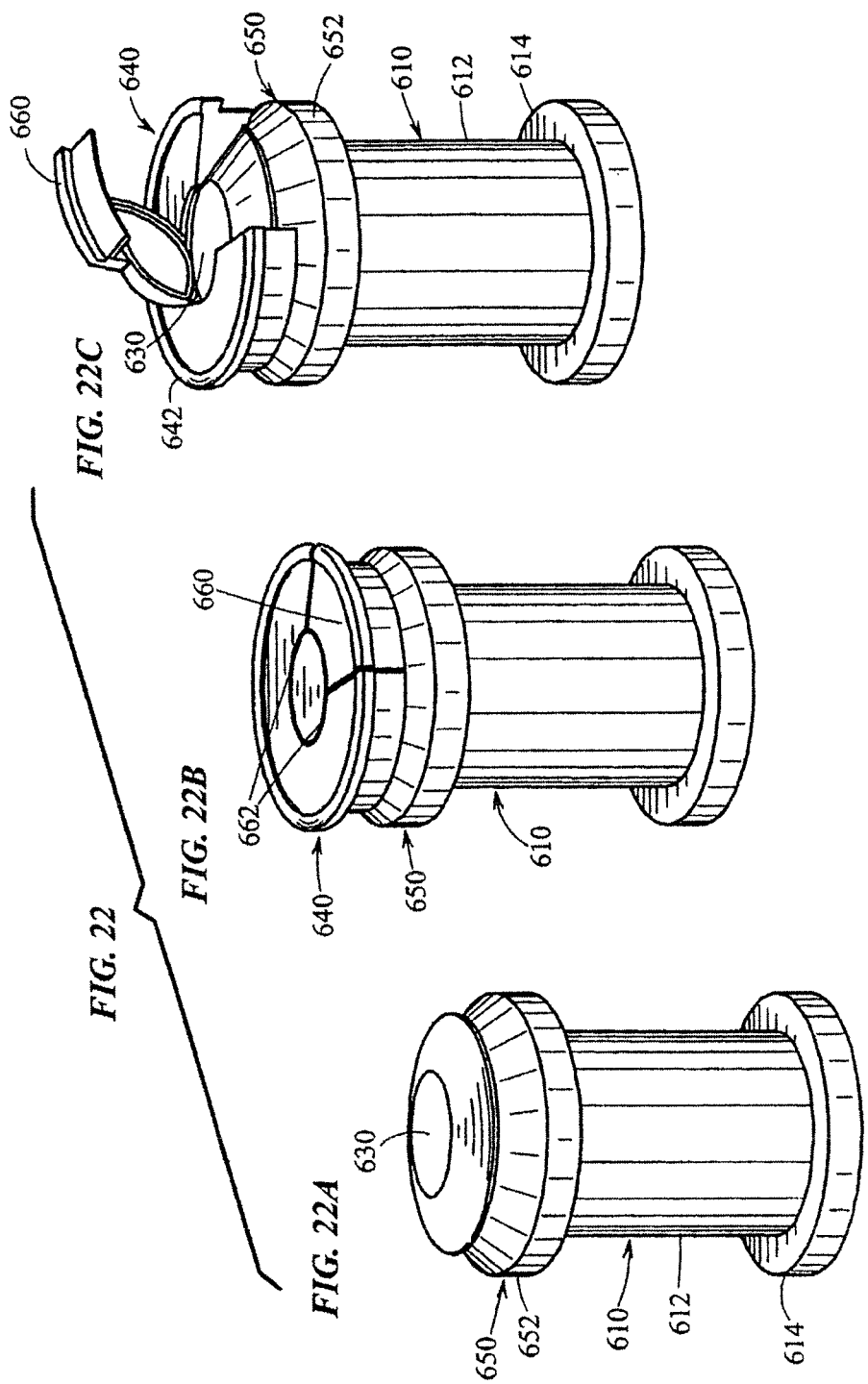

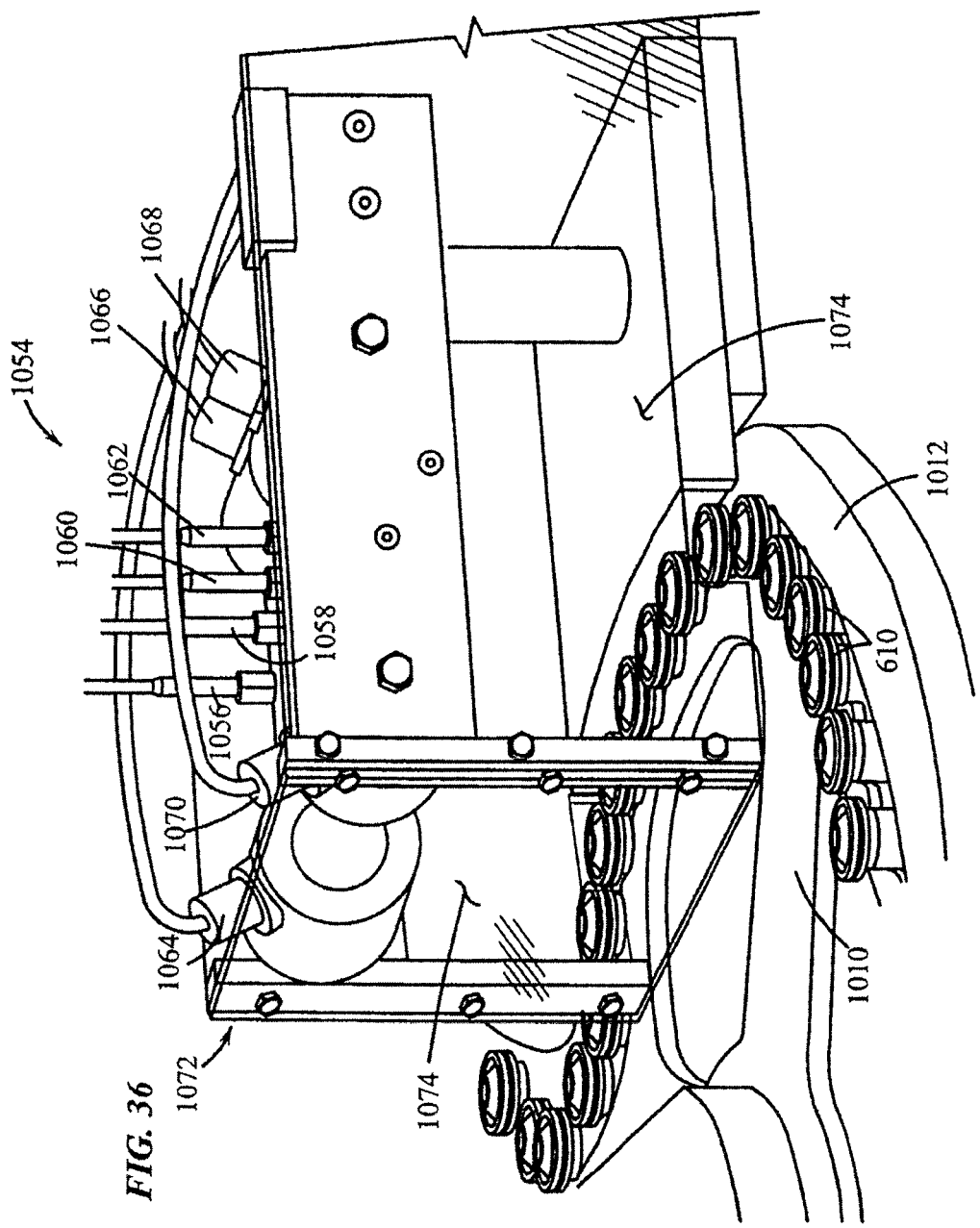

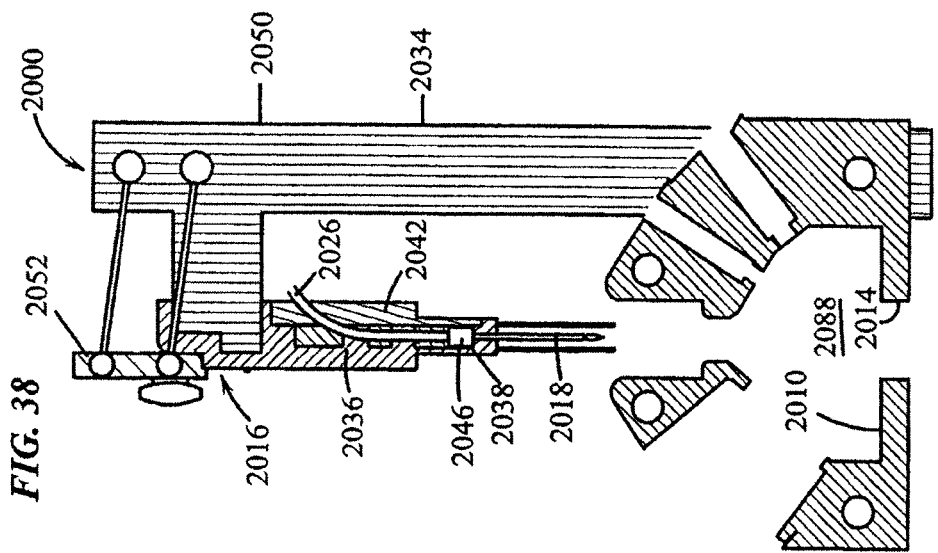
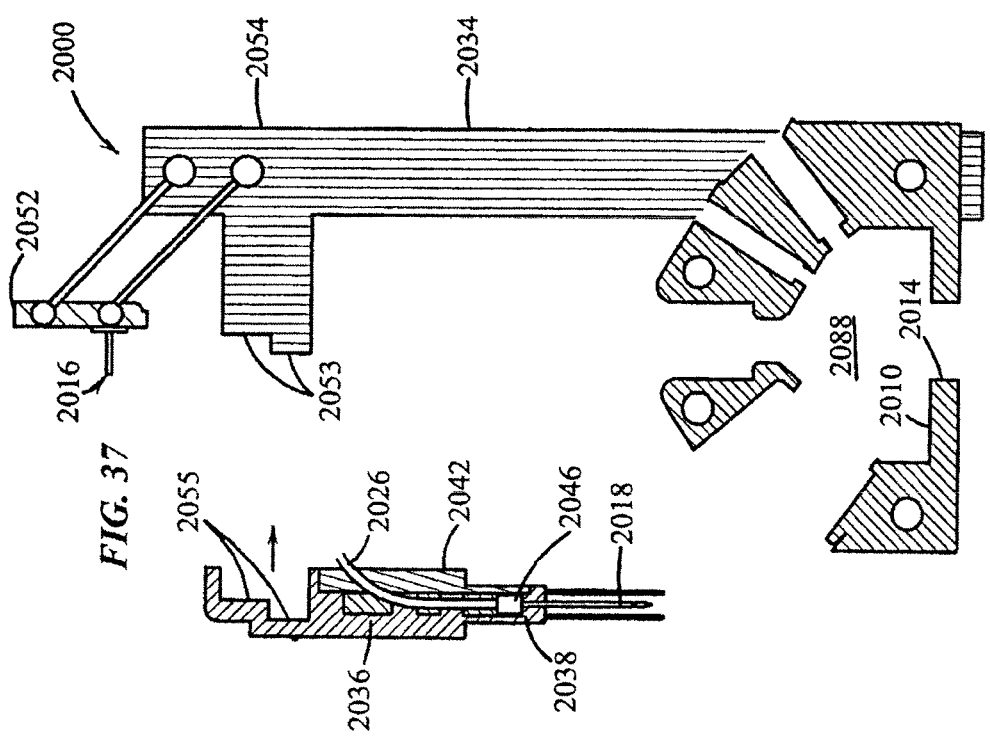

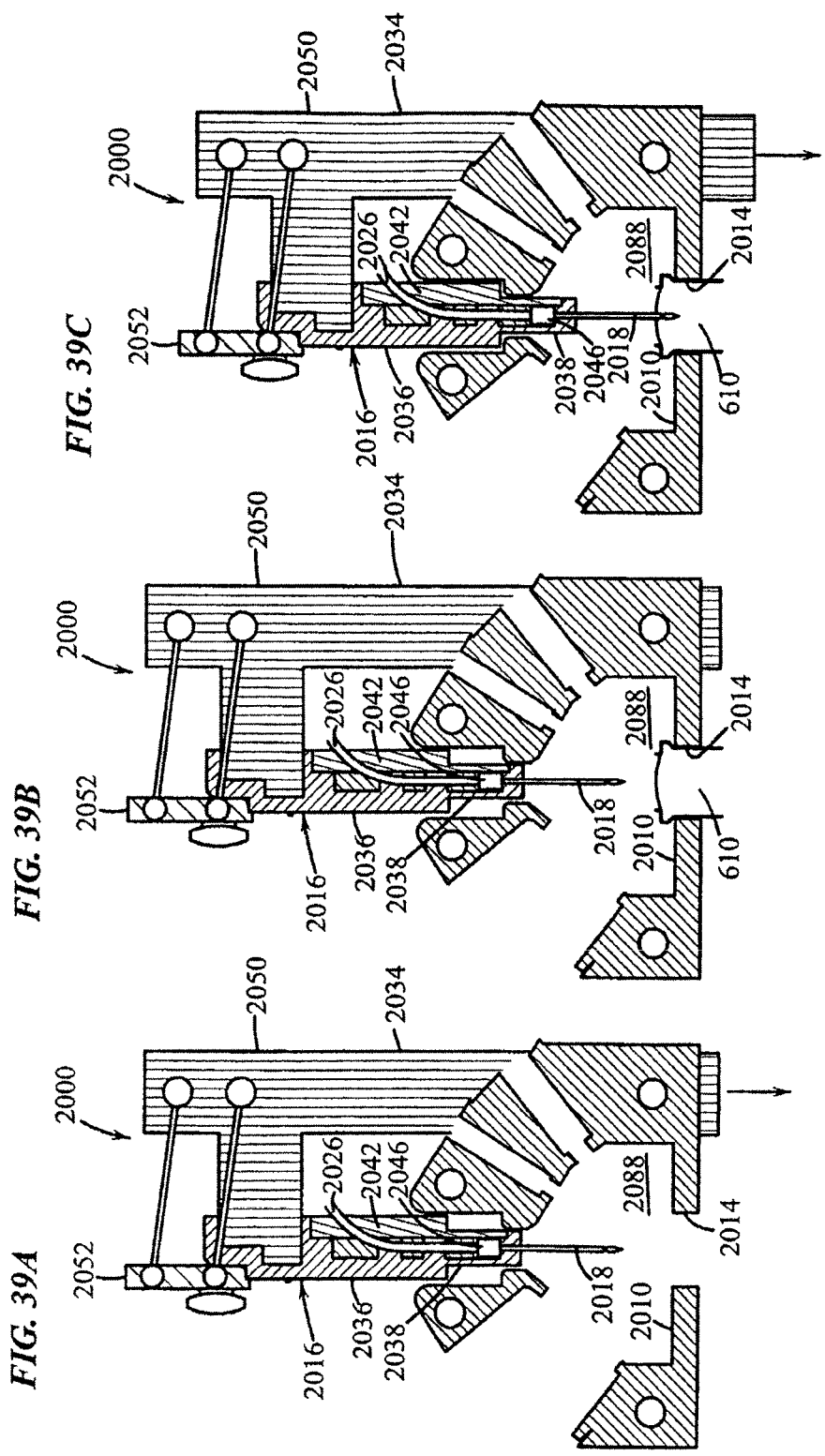

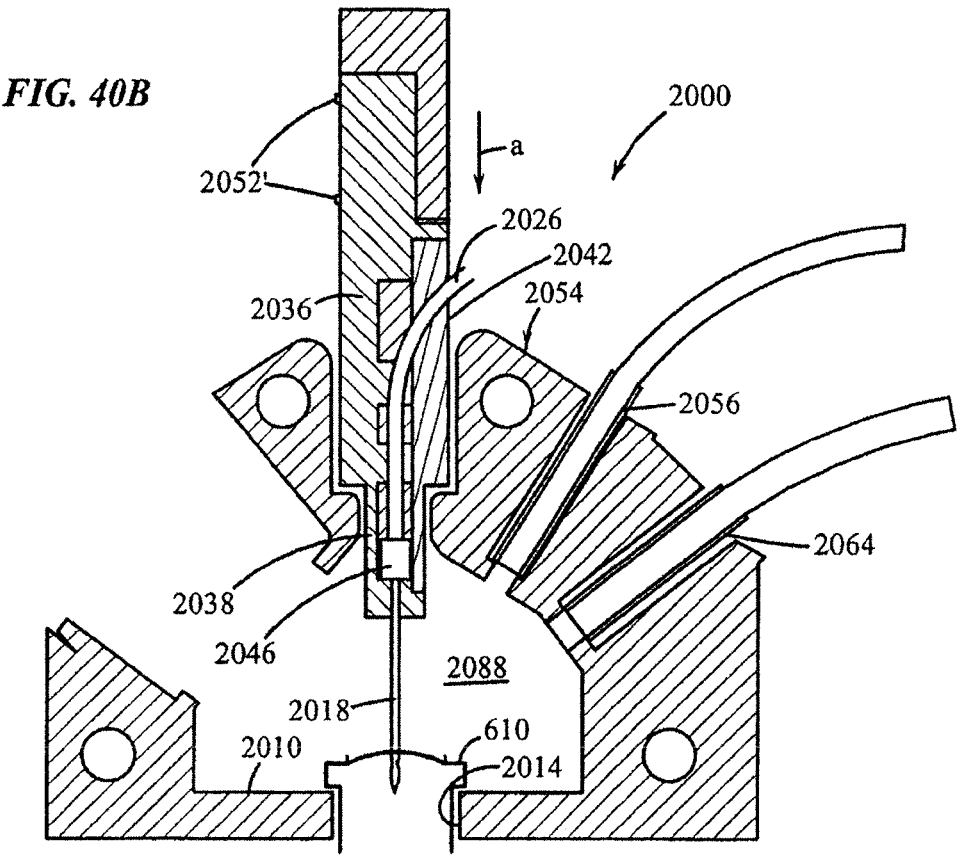

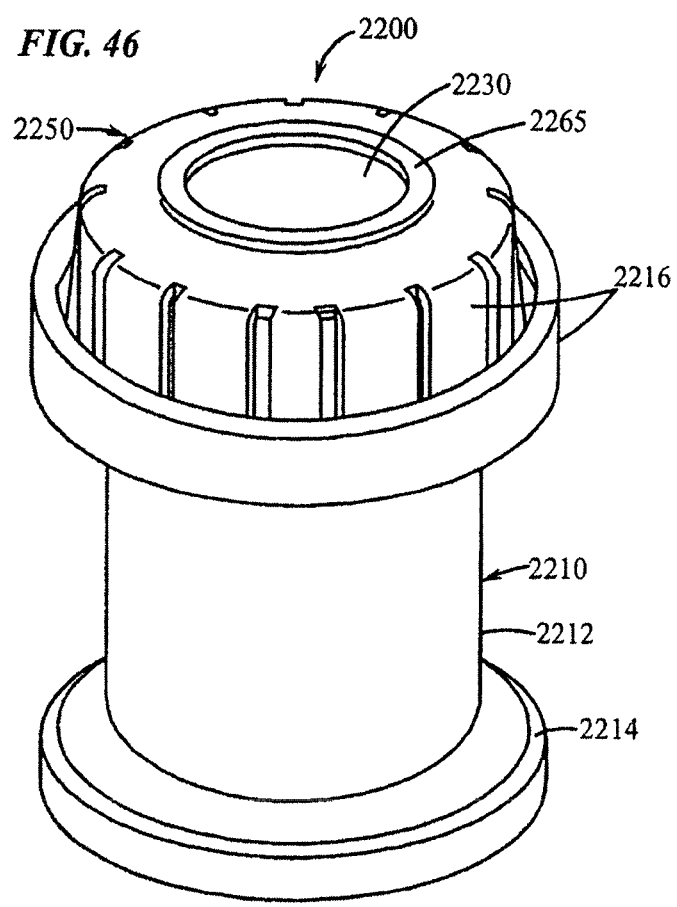

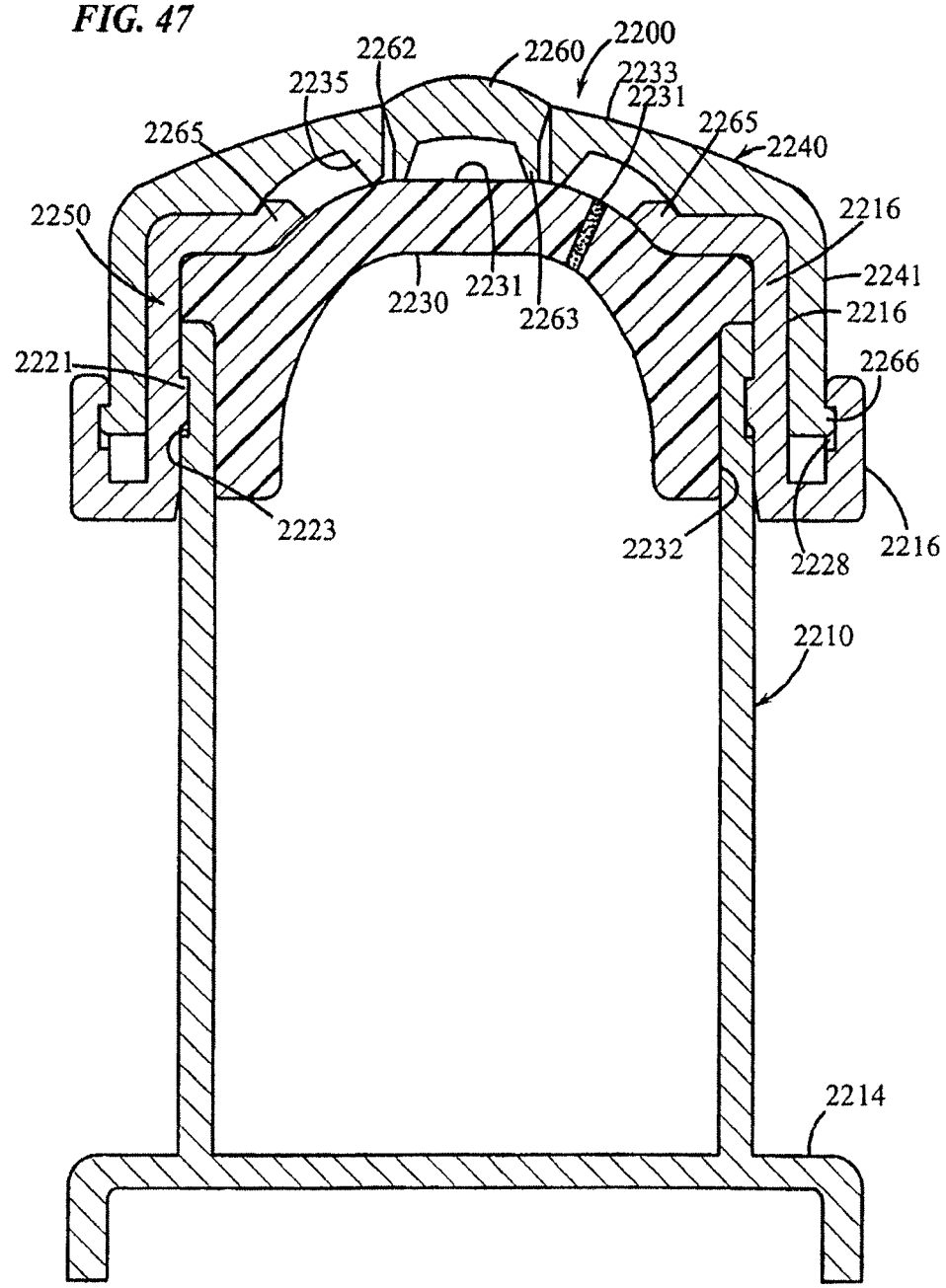

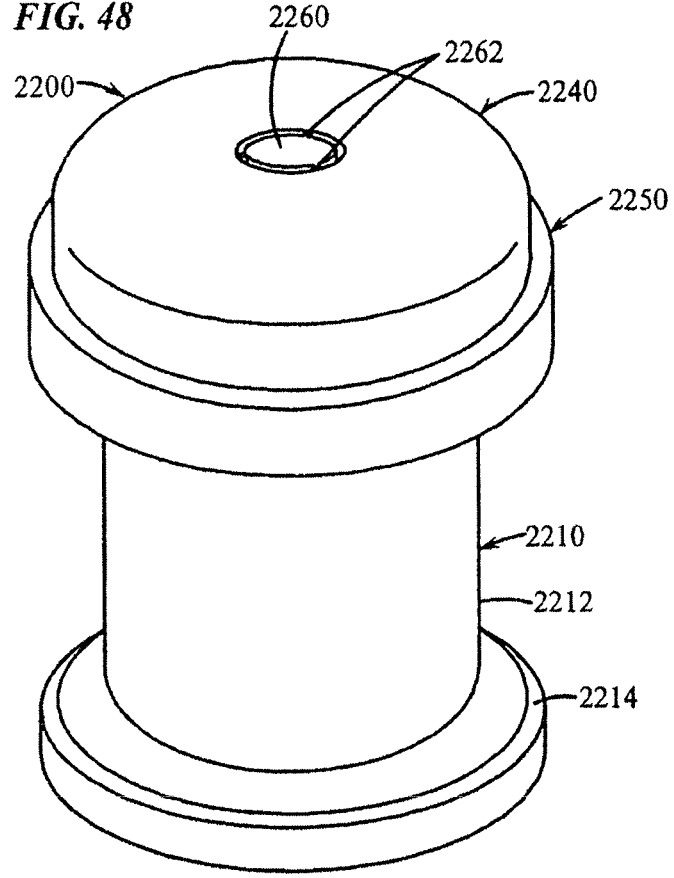

SEALED CONTAINERS AND METHODS OF FILLING AND RESEALING SAME

CROSS REFERENCE TO RELATED APPLICATIONS

This application is a divisional of U.S. patent application Ser. No. 13/193,662, filed Jul. 29, 2011, entitled "Sealed Containers and Methods of Making and Filling Same," which is a continuation of similarly-titled U.S. patent application Ser. No. 12/791,629, filed Jun. 1, 2010, now U.S. Pat. No. 7,992,497, which is a divisional of similarly-titled U.S. patent application Ser. No. 11/515,162, filed Sep. 1, 2006, now U.S. Pat. No. 7,726,352, which is a continuation of similarly-titled U.S. patent application Ser. No. 10/655,455, filed Sep. 3, 2003, now U.S. Pat. No. 7,100,646, which claims priority to similarly-titled U.S. Provisional Patent Application No. 60/408,068, filed Sep. 3, 2002 and is also a continuation-in-part of U.S. patent application Ser. No. 10/393,966, filed Mar. 21, 2003, entitled "Medicament Vial Having A Heat-Sealable Cap, And Apparatus and Method For Filling The Vial," now U.S. Pat. No. 6,684,916, which is a divisional of similarly-titled U.S. patent application Ser. No. 09/781,846, filed Feb. 12, 2001, now U.S. Pat. No. 6,604,561, issued Aug. 12, 2003, which, in turn, claims the benefit of similarly-titled U.S. Provisional Application Ser. No. 60/182,139, filed on Feb. 11, 2000. The above-referenced applications are hereby expressly incorporated by reference as part of the present disclosure.

FIELD OF THE INVENTION

The present invention relates to sealed containers, and more particularly, to containers, such as medicament vials, which have unique spool-like or "diabolo" shaped configurations, and still more particularly, to containers that include a closure device that hermetically seals the container, that can be sterilized using irradiation, such as laser, gamma, e-beam, x-ray or other forms of ionizing radiation, that can be needle filled when sealed to the container, and that can be thermally resealed after needle filling, such as by applying laser radiation to the needle fill hole.

BACKGROUND OF THE RELATED ART

Medicaments such as vaccines are often stored in vials prior to use. Vials typically include a main body portion that is either cylindrical or spherical in shape and has a neck portion depending therefrom. The neck portion defines a mouth for receiving the medicament into an interior chamber defined in the vial body. Normally, the vials are filled with medicament, and then a pre-sterilized cap or closure device is installed to seal the medicament within the vial.

The vial cap is typically a two-piece assembly that includes a stopper and a securing ring. The stopper is inserted into the mouth of the vial and is configured to effectuate a circumferential seal. The securing ring is engaged with the neck of the vial and at least partially overlies the stopper so as to retain the stopper within the vial mouth. The stopper is made of vulcanized rubber or similar resilient material that neither contaminates nor affects the contained medicament. Vulcanized rubber has been determined to be a safe and effective material for manufacturing vial caps for containing numerous types of medicaments. Vulcanized rubber, however, is infusible, and therefore any needle holes in such caps are not heat-resealable.

The securing ring is typically configured such that a portion of the stopper is exposed and can be accessed by a needle, thereby allowing the medicament to be withdrawn. Traditionally, securing rings are threadably engaged with the vial or affixed therewith by a metal crimping technique. In applications such as healthcare, a crimped metal securing ring is frequently preferred, since a crimped ring provides a mechanism for assuring that the vial has not been opened or compromised subsequent to being filled or sterilized.

Referring to FIG. 1, a prior art cap for a medicament vial is designated generally by reference numeral 10. The cap 10 includes a vulcanized rubber stopper 12, which is slidably received within the open end or mouth 8 of a cylindrical vial body 14. The vial body 14 is made of glass or like material, and it defines a chamber 16 for receiving medicament. An aluminum locking ring 18 surrounds the periphery of the stopper 12 and vial 14, and is crimped in place to secure, connect and seal the cap 10 to the vial body 14. The locking ring 18 includes a central aperture which affords limited access to the stopper 12.

In order to fill such prior art vials with a sterile fluid or other substance, such as a medicament, it is typically necessary to sterilize the unassembled components of the vial, such as by autoclaving the components and/or exposing the components to gamma radiation. The sterilized components then must be filled and assembled in an aseptic isolator of a sterile filling machine. In some cases, the sterilized components are contained within multiple sealed bags or other sterile enclosures for transportation to the sterile filling machine. In other cases, the sterilization equipment is located at the entry to the sterile filling machine. In a filling machine of this type, every component is transferred sterile into the isolator, the storage chamber of the vial is filled with the fluid or other substance, the sterilized stopper is assembled to the vial to plug the fill opening and hermetically seal the fluid or other substance in the vial, and then the crimping ring is assembled to the vial to secure the stopper thereto.

One of the drawbacks associated with such prior art vials, and processes and equipment for filling such vials, is that the filling process is time consuming, and the processes and equipment are expensive. Further, the relatively complex nature of the filling processes and equipment can lead to more defectively filled vials than otherwise desired. For example, typically there are at least as many sources of failure as there are components. In many cases, there are complex assembly machines for assembling the vials or other containers that are located within the aseptic area of the filling machine that must be maintained sterile. This type of machinery can be a significant source of unwanted particles. Further, such isolators are required to maintain sterile air within a barrier enclosure. In closed barrier systems, convection flow is inevitable and thus laminar flow, or substantially laminar flow, cannot be achieved. When operation of an isolator is stopped, a media fill test may have to be performed which can last for several, if not many days, and can lead to repeated interruptions and significant reductions in production output for the pharmaceutical or other product manufacturer that is using the equipment. In order to address such production issues, government-imposed regulations are becoming increasingly sophisticated and are further increasing the cost of already-expensive isolators and like filling equipment. On the other hand, governmental price controls for injectables and vaccines, including, for example, preventative medicines, discourage such major financial investments. Accordingly, there is a concern that fewer companies will be able to afford such increasing levels of investment in sterile filling machines, thus further reducing competition in the injectable and vaccine marketplaces.

In order to address these and other concerns, the present inventor has determined that it would be desirable to manufacture and fill vials by first assembling the stopper to the vial, sterilizing the assembled stopper and vial, such as by irradiation, and then filling the assembled vial by inserting a needle or like injection member through the stopper and introducing the medicament through the needle into the sterilized vial. One problem encountered with this approach, however, is that when the needle or like injection member is inserted through the stopper and then withdrawn, it leaves a tiny hole in the stopper. The material of the stopper is resilient in order to reduce the diameter of the hole, and therefore the hole is usually small enough to keep the medicament from leaking out. However, the hole typically is not small enough to prevent air or other gases from passing through the hole and into the vial, and therefore such holes can allow the medicament to become contaminated or spoiled.

It has been a practice in the pharmaceutical fields to add preservatives to medicaments, such as vaccines, in order to prevent spoilage of the medicaments upon exposure to air or other possible contaminants. Certain preservatives, however, have been determined to cause undesirable effects on patients. Consequently, many medicaments, including vaccines, are preservative free. These preservative-free medicaments, and particularly preservative-free vaccines, are subject to contamination and/or spoilage if contained within a vial wherein the stopper has a needle hole as described above.

As noted above, it is difficult to maintain the sterility of stoppers and vials during the transportation, storage and assembly process. There is a need, therefore, for vials and stoppers which can be assembled and then sterilized as a unit prior to filling the vial assembly with medicament. Although crimped metal rings provide a mechanism for ensuring that the vial has not been compromised, the metal ring does not allow the vial assembly to be easily sterilized as a unit by using a gamma sterilization technique or similar process. A metal ring complicates the gamma sterilization process. Due to the density of the material, shadows (i.e., areas where the gamma radiation is prevented from passing through the material) are created which reduces the assurance that the interior storage cavity has been completely sterilized. Also, the handling of the metal rings during the assembly process can create dust and/or other particulates that can contaminate the clean environment established for vial assembly and filling.

Additionally, the shape of conventional medicament vials can be disadvantageous from a safety and/or handling perspective. For example, when a healthcare worker is withdrawing medicament from the vial, his/her fingers must grasp the cylindrical or spherical vial body. In conventional vials, the vial body has an outer diameter that is greater than the outer diameter of the cap or closure. If the needle slips off of the cap due, for example, to the relative placement of the fingers with respect to the cap, the healthcare worker's fingers are positioned in the slip path of the needle and therefore are likely to be pierced, causing a variety of safety concerns. In addition, such conventional vials have a relatively high center of gravity making them prone to tipping during handling, and further, define shapes and/or configurations that are not always well suited for needle filling and/or automated handling in such needle filling and laser or other thermal resealing machines.

Accordingly, it is an object of the present invention to overcome one or more of the above-described drawbacks and disadvantages of the prior art.

SUMMARY OF THE INVENTION

In accordance with a first aspect, the present invention is directed to method. The method comprises providing a container including a container body and a heat-resealable stopper fusible in response to the application of thermal energy thereto. The body defines an empty chamber, sealed with respect to ambient atmosphere, and in fluid communication with the stopper for receiving therein a predetermined substance. The container further includes a base, a mid-portion, and an upper portion axially spaced from the base on an opposite side of the mid-portion relative to the base, wherein each of the base and upper portion define a laterally-extending dimension greater than a maximum laterally-extending dimension of the mid-portion. The method further comprises the steps of penetrating the stopper with an injection member coupled in fluid communication with a source of predetermined substance, introducing the predetermined substance through the injection member and into the chamber of the container, and withdrawing the injection member from the stopper. Additionally, the method comprises the steps of engaging the base of the body with a support during the step of withdrawing the injection member and substantially preventing axial movement of the body relative thereto, and applying sufficient energy to the stopper to thermally fuse the penetrated region and form a substantially gas-tight seal between the penetrated region and the chamber.

In some embodiments, the method further comprises the step of assembling the stopper and container body robotically and over-molding a tamper-resistant portion to the stopper and container body. In some embodiments, the assembly of the container body and stopper occurs prior to installing the container body/stopper assembly in a molding apparatus.

Another aspect of the present invention is directed to a method. The method comprises forming a container body defining a chamber in a first mold, which is performed in a clean room environment, and forming a stopper in a second mold in the same clean room environment. The stopper is a thermoplastic stopper defining a needle penetration region that is pierceable with a needle to form a needle aperture therethrough, and is heat resealable to hermetically seal the needle aperture by applying laser radiation at a predetermined wavelength and power thereto. The method further comprises the step of assembling the stopper and container body in the clean room environment to form a sealed empty container. In some embodiments, the first and second molds are located side-by-side within the clean room environment.

In some embodiments, the method further comprising the steps of: penetrating the needle penetration region of the stopper with a filling needle such that the filling needle is in fluid communication with the chamber of the container, introducing the substance through the needle and into the chamber of the container, and withdrawing the filling needle from the stopper. Further, the method comprises the steps of transmitting laser radiation at the predetermined wavelength and power onto an aperture formed in the needle penetration region of the stopper, and hermetically sealing the aperture.

Another aspect of the present invention is directed to a method. The method comprises forming a sealed empty container within a mold. The container includes a body defining a sealed empty chamber, and a thermoplastic portion in fluid communication with the body. The thermoplastic portion defines a penetrable region that is penetrable by a filling member and is heat resealable to hermetically seal an aperture therein by applying laser radiation at a predetermined wavelength and power thereto. The method further comprises the steps of: penetrating the penetrable region of the thermoplastic portion with a filling member such that the filling member is in fluid communication with the sealed empty chamber, introducing the substance through the filling member and into the chamber, and withdrawing the filling member from the thermoplastic portion. Further, the method comprises the steps of transmitting laser radiation at the predetermined wavelength and power onto an aperture formed in the penetrable region of the thermoplastic portion, and hermetically sealing the aperture and the substance within the chamber. In some embodiments, the method further comprises sterilizing the sealed empty container between the forming and penetrating steps.

Another aspect of the present disclosure is directed to a vial assembly for storing a substance, such as a medicament, comprising a body defining an opening, and a chamber in fluid communication with the opening for receiving therein the substance. The body defines a base, a mid-portion, and an upper portion axially spaced from the base on an opposite side of the mid-portion relative to the base. Each of the base and upper portion define a laterally-extending dimension that is greater than a maximum laterally-extending dimension of the mid-portion. In a currently preferred embodiment of the present invention, each of the base, mid-portion and upper portion are approximately circular in cross section, and a maximum diameter of each of the base and upper portion is greater than a maximum diameter of the mid-portion to thereby define an approximate diabolo or spool shape. Preferably, the vial assembly includes a plastic tamper-resistant portion that is fixedly secured to the body and extends at least partially over the stopper for preventing unnoticeable removal of the stopper.

In some embodiments, the stopper includes a heat resealable portion overlying a substantially infusible portion. In another embodiment of the present invention, the stopper is a thermoplastic stopper defining a needle penetration region that is pierceable with a needle to form a needle aperture therethrough, and is heat resealable to hermetically seal the needle aperture by applying laser radiation at a predetermined wavelength and power thereto. The stopper comprises a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal a needle aperture formed in the needle penetration region thereof in a predetermined time period of less than approximately 2 seconds and substantially without burning the needle penetration region.

Another aspect of the present disclosure is directed to a method. The method comprises providing a vial including a body defining an opening, a chamber in fluid communication with the opening for receiving therein a predetermined substance, a base, a mid-portion, and an upper portion axially spaced from the base on an opposite side of the mid-portion relative to the base. Each of the base and upper portion define a laterally-extending dimension greater than a maximum laterally-extending dimension of the mid-portion, and a heat-resealable stopper fusible in response to the application of thermal energy thereto. Prior to filling the vial with substance, the method further comprises the step of assembling the stopper and vial and forming a substantially gas-tight seal between the stopper and vial. The method further comprises the steps of sterilizing the empty assembled stopper and vial and supporting the vial with a vial support including a mounting surface in engagement with the mid-portion of the vial, an upper surface located on one side of the mounting surface, and a lower surface located on another side of the mounting surface. Further, the method comprises the steps of penetrating the stopper with a needle coupled in fluid communication with a source of predetermined substance, introducing the predetermined substance through the needle and into the interior of the vial, withdrawing the needle from the stopper, and applying sufficient thermal energy to the penetrated region of the stopper to fuse the penetrated region and form a substantially gas-tight seal between the penetrated region and the interior of the vial.

One advantage of the preferred embodiments of the present invention is that the vial defines a diabolo or spool-like shape, thus facilitating the prevention of accidental needle sticks during use and otherwise facilitating handling of the vial during filling and other processing. Another advantage of certain preferred embodiments of the present invention is that the stopper and vial may be assembled without human intervention and prior to filling to thereby form hermetically sealed, empty vials that may be sterilized and maintained in the sterilized condition prior to filling. Yet another advantage of certain preferred embodiments of the present invention is that the plastic or like tamper-resistant portion allows the empty vials to be sterilized, such as by the application of gamma, e-beam or other radiation thereto.

Other advantages of the present invention, and/or the disclosed embodiments thereof, will become more readily apparent in view of the following detailed description of currently preferred embodiments and accompanying drawings.

BRIEF DESCRIPTION OF THE DRAWINGS

So that those having ordinary skill in the art to which the present application appertains will more readily understand how to make and use the same, reference may be had to the drawings wherein:

FIGS. 12a through 12d are somewhat schematic, cross-sectional, sequential views illustrating an apparatus and method for hermetically sealing the penetrated region of the resealable stoppers of the vials of the present disclosure by direct heat sealing after withdrawing the filling needle therefrom;

FIGS. 13A through 13C are somewhat schematic, cross-sectional, sequential views illustrating an apparatus and method for hermetically sealing the penetrated region of the resealable stoppers of the vials of the present disclosure by laser sealing after withdrawing the filling needle therefrom;

FIGS. 17A through 17C are cross-sectional, sequential views of an alternate over-molding process for making over-molded vials embodying the present disclosure, wherein both the vial closure and the base portion of the vial are formed by injection molding;

FIG. 20 is a cross-sectional view of the stopper of the vial of FIG. 19;

FIG. 21 is a cross-sectional view of the stopper and securing ring of the vial of FIG. 19;

FIG. 22A is a perspective view of the vial of FIG. 18 with the tamper-resistant cover removed;

FIG. 22B is a perspective view of the vial of FIG. 18 including the tamper-resistant cover fixedly secured thereto;

FIG. 22C is a perspective view of the vial of FIG. 18 illustrating the frangible portion of the tamper-resistant cover flipped upwardly to expose the resealable stopper and allow same to be penetrated with the needle of a syringe to withdraw the medicament of other substance contained within the vial into the syringe;

FIG. 36 is a perspective view of a laser sealing and infrared sense manifold mounted downstream of the needle manifold of FIGS. 32-35 in a sterile enclosure of a sterile filling machine for laser resealing the needle holes in the filled vials;

FIG. 37 is a partly exploded, end elevation view of a module including a needle manifold, laser optic assemblies, and sensors, for needle filling and laser resealing the vials therein, and with some parts removed for clarity;

FIG. 38 is an end elevation view of the module of FIG. 37 showing the needle manifold clamped to the drive plate, and with some parts removed for clarity;

FIG. 39A is an end elevation view of the module of FIG. 37, with parts removed for clarity, without any vials received within the module, and showing the needles in the "up" position;

FIG. 39B is an end elevation view of the module of FIG. 39A showing vials received within the module and ready to be needle pierced and filled;

FIG. 39C is an end elevational view of the module of FIG. 39A showing the needle manifold in the "down" position with the needles piercing the resealable stoppers for allowing the medicament or other substance to be pumped through the needles to fill the vials;

FIG. 40B is an end elevation view of the module of FIG. 40A showing the needle piercing the resealable stopper to, in turn, fill the interior chamber of the respective vial with a medicament or other substance to be contained therein;

FIG. 46 is an upper perspective view of the vial of FIG. 45 with the tamper-resistant cover removed;

FIG. 47 is another cross-sectional view of the vial of FIG. 45 including the tamper-resistant cover secured thereto, and illustrating the manner in which the laser resealed portion of the stopper is visually concealed under the tamper-resistant cover upon removal of the frangible portion thereof; and FIG. 48 is an upper perspective view of the vial of FIG. 47.

DETAILED DESCRIPTION OF EMBODIMENTS OF THE INVENTION

Reference is now made to the accompanying figures for the purpose of describing, in detail, preferred embodiments of the present disclosure. The figures and accompanying detailed description are provided as examples of the disclosed subject matter and are not intended to limit the scope thereof.

Figure 1:
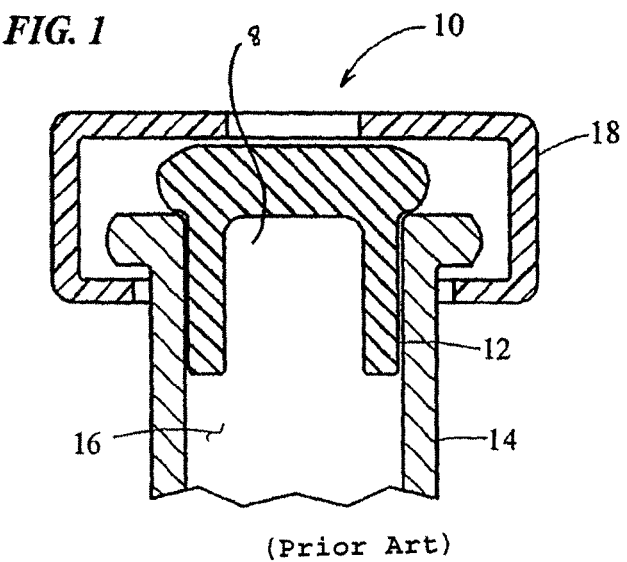
FIG. 1 is a cross-sectional view of a prior art cap for a medicament vial.
Figure 2:
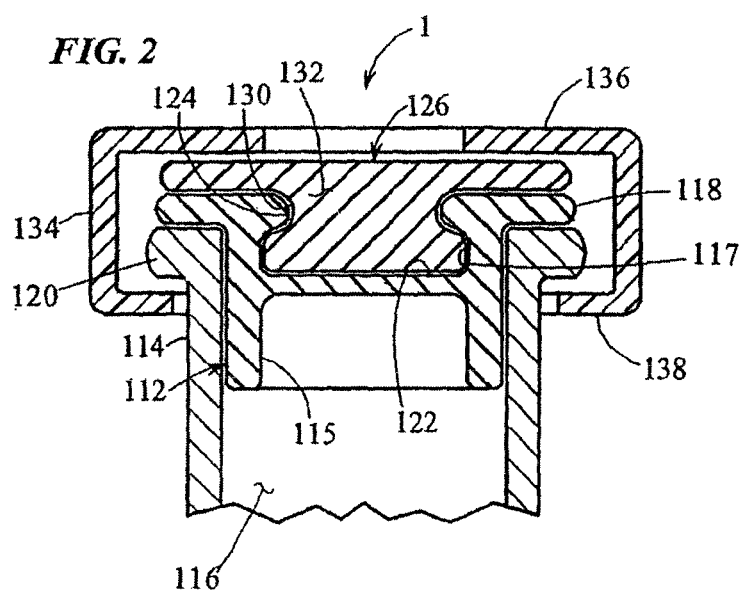
FIG. 2 is a cross-sectional view of a resealable stopper that may be employed in any of the vial assemblies of the present disclosure.
Figure 3:
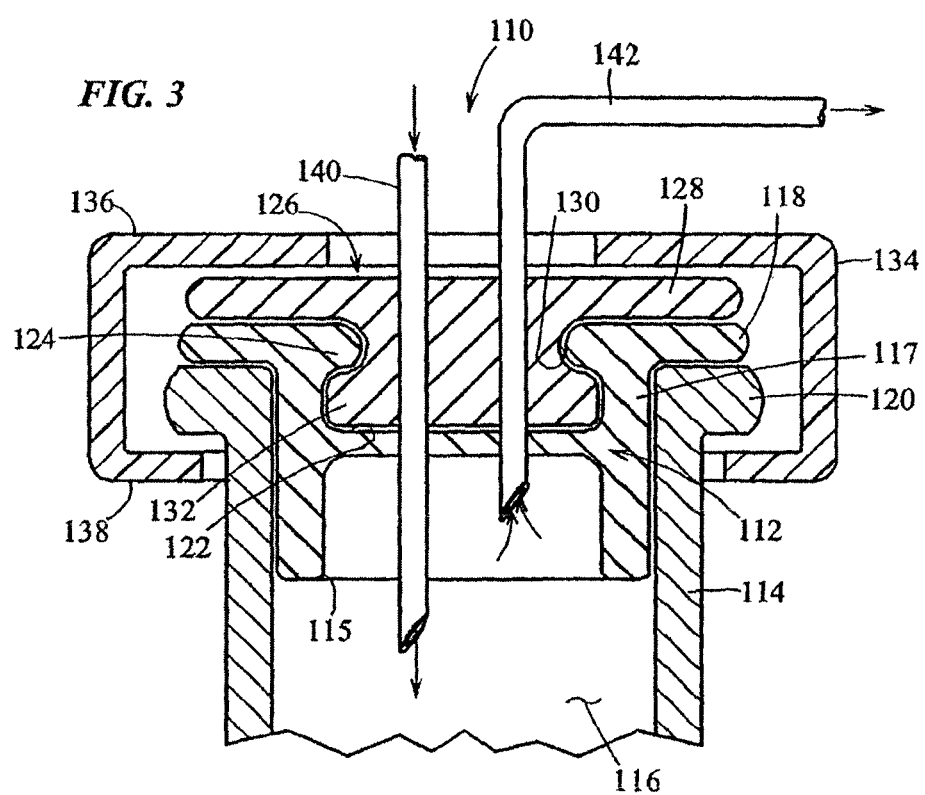
FIG. 3 is a cross-sectional view of the resealable stopper of FIG. 2 shown with an injection needle or syringe inserted through the stopper for introducing medicament into the vial, and a venting needle or syringe inserted through the stopper for venting the vial during filling of the medicament.
Figure 4:
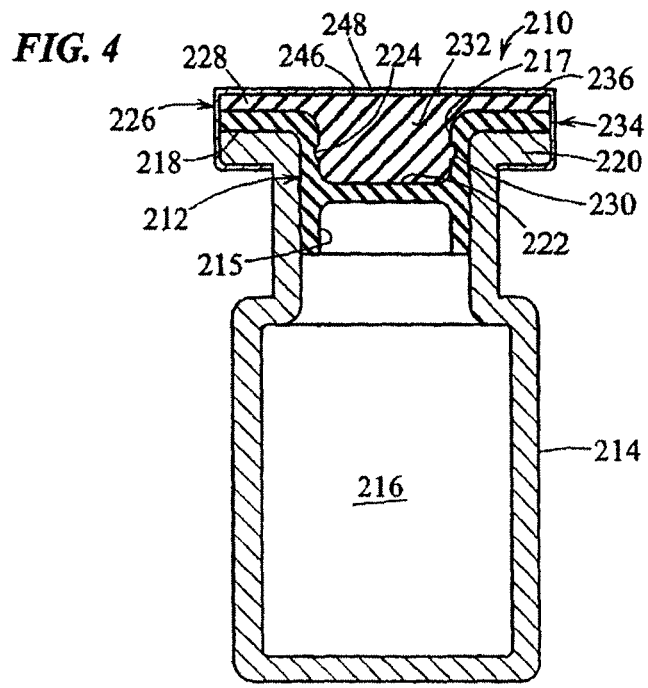
FIG. 4 is a cross-sectional view of another embodiment of the resealable stopper and vial.

Turning to FIG. 2, a heat-resealable cap or stopper that may be used in the vials of the present invention is indicated generally by the reference numeral 110. The cap 110 includes a resilient base 112 made of vulcanized rubber or like material which is known to those of ordinary skill in the pertinent art, and acceptable for use in the manufacture of end caps or the portions thereof placed in contact with, or otherwise exposed to medicaments or other substances to be contained in the vials, such as vaccines. The base 112 defines a lower peripheral wall 115 shaped and dimensioned to be slidably received within the open end of a vial 114. The vial 114 may be made of any of numerous different types of glass or plastic, or any other material that is currently or later becomes known for use in connection with making vials, such as vials for storing medicaments or other substances. The vial 114 defines therein a chamber 116 for receiving medicament. As described further below, the vial preferably defines a "diabolo" or spool-like shape to, for example, facilitate handling of the vial during sterilization, filling and/or other processing of the vial, and during use of the vial. The base 112 of the cap 110 further defines an upper peripheral wall 117 also shaped and dimensioned to be slidably received within the open end of the vial 114, and a peripheral sealing flange 118 projecting outwardly from the upper end of the peripheral wall 117. The vial 114 defines at its open end a peripheral flange 120. As shown in FIGS. 2 and 3, the peripheral flange 118 of the base 112 sealingly engages the peripheral flange 120 of the vial 114 to seal the interface between the cap and vial. The base 112 further defines an upper recess 122 formed within the upper peripheral wall 117, and an annular rim 124 projecting inwardly from the upper end of the peripheral wall.

A resealable portion 126 is fixedly received within the upper recess 122 of the base 112 to form the assembled cap 110. The resealable portion 126 defines an upper peripheral flange 128, an annular recessed portion or recess 130, and a base 132 located on the opposite side of the annular recess 130 relative to the flange, and projecting outwardly from the recess. As can be seen in FIGS. 2 and 3, the annular recess 130 and base 132 of the resealable portion 126 are dimensioned and shaped complementary to (or define the mirror image of) the interior surfaces of the upper recess 122 and annular rim 124 of the base 112. Accordingly, the resealable portion 126 is pressed, snapped or otherwise received within the upper recess 122 such that the annular rim 124 is received within the annular recess 130 to thereby fixedly secure the resealable portion within the base.

The resealable portion 126 is preferably made of a resilient polymeric material, such as a blend of a first polymeric material sold under the registered trademark KRATON® or DYNAFLEX® and a second material in the form of a low-density polyethylene, such as the polyethylene sold by Dow Chemical Co. under the trademarks ENGAGE™ or EXACT™. In some embodiments, the first and second materials are blended within a range of about 50:50 by weight to about 90:10 by weight (i.e., first material: second material). In one embodiment, the blend of the first and second materials is about 50:50 by weight. The benefits of the preferred blend over the first material by itself are improved water or vapor barrier properties, and thus improved product shelf life; improved heat sealability; a reduced coefficient of friction; improved moldability or mold flow rates; and a reduction in hysteresis losses. As may be recognized by those skilled in the pertinent art, these numbers and materials are only exemplary, however, and may be changed if desired or otherwise required.

An important feature of the resealable portion 126 is that it be resealable to form a gas-tight seal after inserting a needle, syringe or like injection member through the resealable member. Preferably, the resealable portion can be sealed by heating the area punctured by the needle as described further below. One advantage of the blended polymer described above is that it is known to minimize the degree to which the medicament can be absorbed into the polymer in comparison to either KRATON® or DYNAF-LEX® itself.

An aluminum locking or crimping ring 134 defining an upper peripheral flange 136 and a lower peripheral flange 138 may be mounted over the end cap 110 and vial 114. The upper and lower flanges 136 and 138, respectively, of the locking ring are crimped or otherwise pressed against the adjacent surfaces of the cap and vial to press the sealing flanges of the cap against the vial and thereby maintain a fluid-tight and/or gas-tight seal between the cap and vial. Alternatively, the locking ring may be formed of a non-metallic material, such as a plastic material, that may be snap-fit to the underside of the peripheral flange 120, or otherwise secured to the flange of the vial body, as described further below.

As shown in FIG. 3, the heat-resealable cap 110 is shown with a hypodermic or other type of needle 140 inserted through the resealable portion 126 and the resilient base 112 in order to dispense medicament into the chamber 116 of the vial. A venting needle 142 likewise may be inserted through the resealable portion 126 and the resilient base 112 in order to allow gas to escape from the vial 114 as the medicament is deposited into the vial. Alternatively, the needle 140 may define one or more axially-elongated grooves in an outer surface thereof to allow gas within the vial to vent therethrough and thereby eliminate the need for the venting needle 142, or the needle may take the form of a "double" or "multi" lumen needle wherein the one lumen of the needle delivers the medicament or other substance to be contained within the vial, and another lumen permits the gas displaced by the medicament or other substance to flow out of the vial. The apparatus and method for dispensing medicament or other substances into the vial may take a form as shown in U.S. Pat. No. 5,641,004 to Daniel Py, issued Jun. 24, 1997, and more preferably, may take a form as shown in U.S. Provisional Patent Application No. 60/484,204, filed Jun. 30, 2003, entitled "Medicament Vial Having A Heat-Sealable Cap, And Apparatus And Method For Filling The Vial," each of which is hereby expressly incorporated by reference as part of the present disclosure.

In operation, the resealable portion 126 is inserted into the base 112, and the assembled end cap 110 is slidably inserted into the open end of the vial 114. The locking ring 134 is then crimped in place to lock the cap 110 to the vial and maintain the gas-tight seal at the interface of the cap and vial. The assembled cap 110 and vial 114 preferably are then sterilized, such as by exposing the assembly to irradiation, such as laser, beta, gamma or e-beam radiation, in a manner known to those of ordinary skill in the pertinent art. The medicament-dispensing needle 140 is then inserted through the resealable portion 126 and the resilient base 112 until the free end of the needle is received into the chamber 116 of the vial to, in turn, dispense medicament into the chamber. The venting needle 142 is likewise inserted through the resealable portion 126 and the resilient base 112 in order to draw gas from the sealed vial as the liquid medicament is deposited within the chamber of the vial. Once the medicament has been deposited within the chamber of the vial, the needles 140 and 142 are withdrawn from the cap 110, and as described further below, a heat or other energy source is applied to the portions of the resealable portion 126 punctured by the needles 140 and 142 to, in turn, seal the punctured areas and hermetically seal the medicament within the vial.

One advantage of the illustrated vial assemblies is that the stopper may be resealed following the deposit of medicament into the interior of the vials, thereby rendering the vials particularly suitable for use with preservative-free medicaments, such as preservative-free vaccines. Accordingly, a further advantage of the illustrated vial assemblies is that the medicament need not contain a preservative, and therefore the above-described drawbacks and disadvantages of such preservatives can be avoided.

Another advantage of the illustrated vial assemblies is that the medicament within the resealed chambers of the vials is not contaminated or otherwise affected by impurities or other agents in the atmosphere where the vial is stored or transported.

Figure 5:
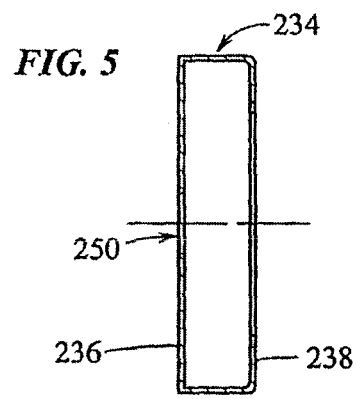
FIG. 5 is a cross-sectional view of the crimpable locking member of FIG. 4 for securing the resealable cap to the vial.
Figure 6:
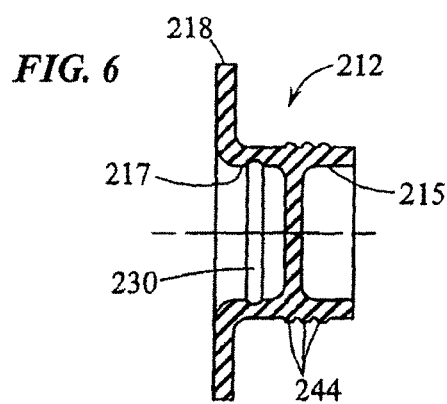
FIG. 6 is a cross-sectional view of the base portion of the resealable stopper of FIG. 4 made of a material compatible with the predetermined medicament to be sealed within the vial, such as vulcanized rubber.

In FIGS. 4 through 8 another resealable stopper or cap that may be employed in the vials of the present invention is indicated generally by the reference numeral 210. The resealable stopper 210 is essentially the same as the stopper 110 described above, and therefore like reference numerals preceded by the numeral "2" instead of the numeral "1" are used to indicate like elements. As shown best in FIGS. 4 and 6, the base 212 of the cap defines on the interior side of its upper peripheral wall 217 an annular groove 230. As shown best in FIGS. 4 and 7, the resealable portion 226 defines on the peripheral surface of its base 232 an annular raised portion or protuberance 224 dimensioned to be frictionally received within the corresponding annular groove 230 of the base 212 to thereby secure the resealable portion to the base. As shown in FIG. 6, the base 212 further defines on the exterior side of its lower peripheral wall 215 a plurality of raised annular portions or protuberances 244 axially spaced relative to each other for frictionally engaging the interior wall of the vial 214 to thereby secure the cap within the vial and facilitate maintaining a hermetic seal between the cap and vial. As shown best in FIGS. 7 and 8, the resealable portion 226 defines on its top surface an annular raised portion or protuberance 246 defining a circular surface portion 248 therein for receiving a filling needle or like instrument, as described further below. As shown in FIG. 5, the locking or crimping ring 234 defines a central aperture 250 in its upper side for receiving therethrough the annular raised portion 246 of the resealable portion 226.

Preferably, the resealable cap 210 and vial 214 are assembled and the locking ring 234 is crimped or otherwise secured in place as described above and shown in FIG. 4 prior to introducing any medicament or other fluid into the vial. Then, one or more of the empty cap/vial assemblies are enclosed, sterilized, and may be transported in accordance with the teachings of the present inventor's commonly owned U.S. Pat. No. 5,186,772, entitled "Method Of Transferring Articles, Transfer Pocket And Enclosure," and/or U.S. patent application Ser. No. 10/241,249, entitled "Transfer Port And Method For Transferring Sterile Items," filed Sep. 10, 2002, each of which is hereby expressly incorporated by reference as part of the present disclosure. The empty cap/vial assemblies may be placed in an internal bag or "pocket" which is closed and, if desired, provided with a sterilization indicator. Then, the internal pocket may be placed within a transfer pocket including a sealing frame defining an annular groove on a peripheral surface thereof. The transfer pocket is stretched over the surface of the frame and closed by an elastic band overlying the transfer pocket and received within the peripheral groove. The transfer pocket likewise may include therein a sterilization indicator. Preferably, the assembled transfer and internal pockets are sealed within an "external" pocket and the assembled pockets are subject to sterilization, such as by exposure to gamma radiation, to sterilize the pockets and the empty cap/vial assemblies within the pockets. The transfer pockets then can be used to store and/or transport the sterilized assemblies to a filling system without contaminating the sterilized assemblies. As further described in the above-mentioned patent and patent application, the filling system is located within a sterile enclosure, and the empty vials are introduced into the enclosure by removing and discarding the external pocket, and connecting the sealing frame of the transfer pocket to a window or transfer port of the enclosure. As further disclosed in the above-mentioned patent and patent application, an adhesive material is preferably superimposed on the sealing frame for securing the transfer pocket to the transfer port of the filling system enclosure. Prior to releasing the vial assemblies into the filling system enclosure, the sterilization indicators may be checked in order to ensure that the sterile condition of the vial assemblies were maintained throughout storage and transfer. As described in the above-mentioned patent and patent application, the portion of the transfer pocket overlying the frame is then cut away and simultaneously sterilized along the trimmed surfaces to destroy any microorganisms or germs thereon, and to allow the internal pocket to be received through the transfer port and into the enclosure.

Once received within the enclosure, the internal pocket is opened and the empty vial assemblies are removed and loaded into a filling machine located within the sterile enclosure. Once loaded into the filling machine, the resealable portion of each empty vial assembly may be sterilized again in order to further ensure that no contaminates enter the vial during the filling process. The resealable portions of the stoppers may be sterilized at this stage by direct heat cauterization, laser cauterization, or the application of another form of radiation, such as e-beam radiation.

Figure 9:
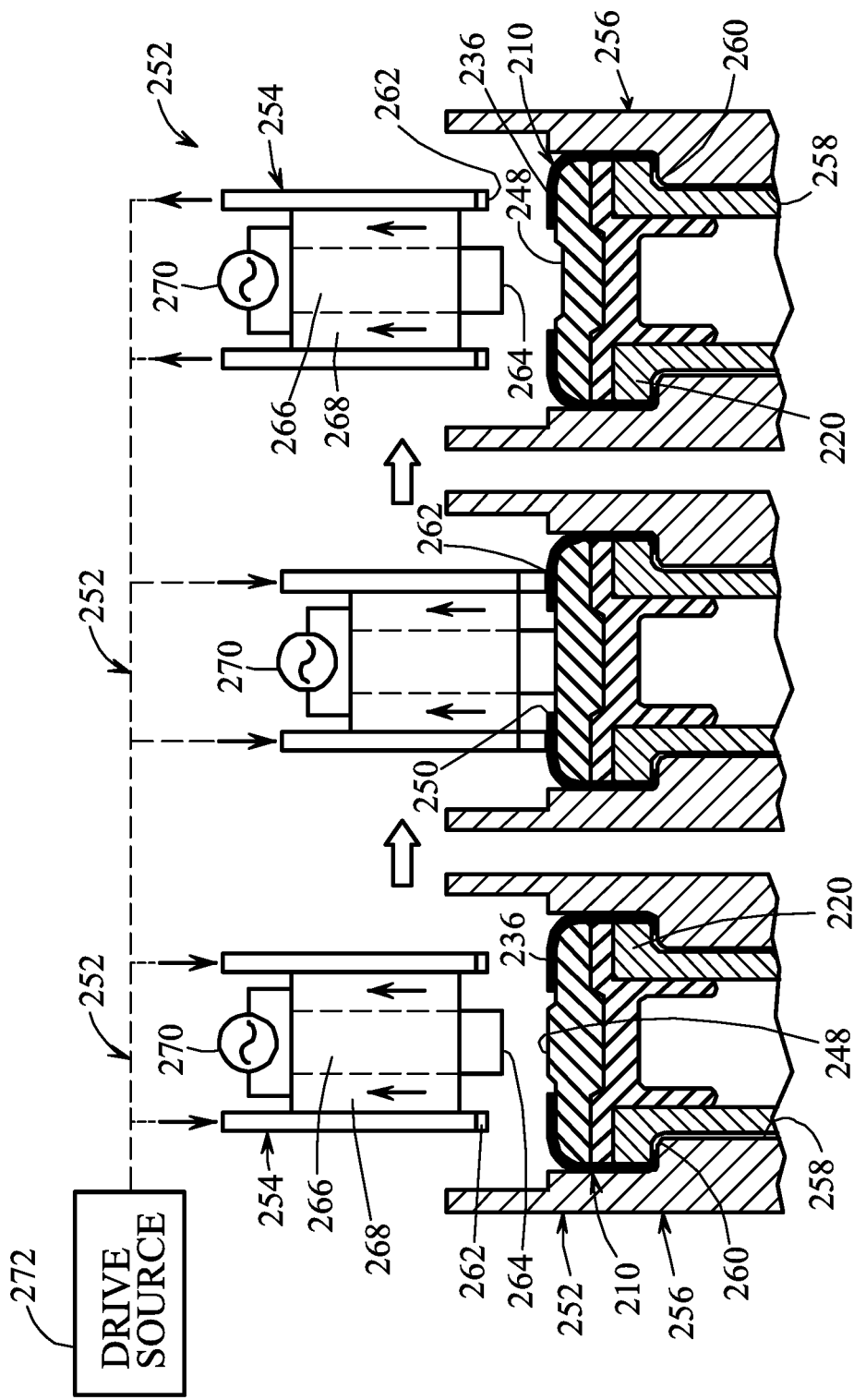
FIGS. 9A through 9C are somewhat schematic, cross-sectional, sequential views illustrating an exemplary apparatus and method for sterilizing the resealable stoppers of the vials of the present disclosure by direct heat cauterization prior to introducing the filling needle or like instrument therethrough.

As shown in FIGS. 9A through 9C, an apparatus for cauterizing the resealable stoppers or caps by application of heat thereto is indicated generally by the reference numeral 252. The apparatus 252 comprises a housing 254 mounted over a vial support 256. The vial support 256 may be adapted to hold a single vial, or preferably, is adapted hold a plurality of vials. The embodiment of the support adapted to hold a plurality of vials defines a channel 258 for receiving therein the vials, and a pair of opposing shoulders 260 formed at the upper edge of the channel for supporting thereon the flange 220 of the vial. If desired, a vibratory drive (not shown) may be drivingly connected to the support 256 to vibrate the support and, in turn, move the vials through the channel at a predetermined rate. Alternatively, the vial support 256 may be mounted on, or otherwise take the form of a conveyor for moving the vials through the sterile filling machine. As may be recognized by those skilled in the pertinent art based on the teachings herein, however, any of numerous different drive systems that are currently, or later become known, may be equally employed to move the vials through the filling machine.

The housing 254 defines a peripheral sealing surface 262 formed on the free end of the housing for sealingly engaging the upper flange surface 236 of each locking member 234. As shown best in FIG. 9b, the peripheral sealing surface surrounds the aperture 250 formed through the locking member and exposing the penetrable region 248 of the resealable portion 226 of the stopper. Preferably, the peripheral sealing surface 262 forms a substantially fluid-tight seal between the housing and the stopper. A heating surface 264 projects outwardly from the free end of a central support 266 of the housing for contacting the penetrable surface 248 of the resealable portion and cauterizing the surface. An annular conduit 268 extends about the periphery of the heating surface 264 and is coupled in fluid communication to a vacuum source 270 for drawing air through the conduit and away from the cauterized surface 248, as indicated by the arrows in the Figures. The housing 254 is drivingly connected to a drive source 272 for moving the housing and thus the heating surface 264 into and out of engagement with the exposed penetrable surface portion 248 for cauterizing the surface, as indicated by the arrows in the Figures. As may be recognized by those skilled in the pertinent art based on the teachings herein, the drive source 272 may take the form of any of numerous different types of drive sources that are currently, or later become known, for performing the function of the drive source as described herein, such as a pneumatic drive, or a solenoid-actuated or other type of electric drive. Similarly, the heating surface 264 may take any of numerous different shapes and configurations, and may be heated in any of numerous different ways that are currently or later become known, such as by an electric resistance heater (or "hot wire"). Preferably, however, the heating surface 264 defines a surface shape and contour corresponding to the desired shape and contour of the penetrable surface region 248 of the cap.

Figure 7:
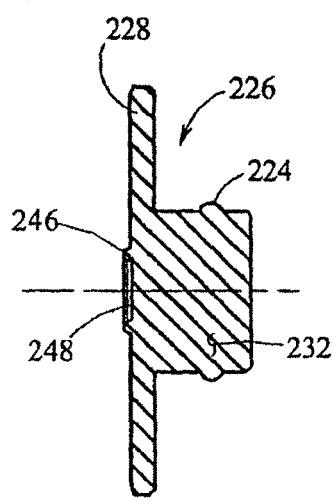
FIG. 7 is a cross-sectional view of the resealable portion of the stopper of FIG. 4 formed of a material that is fusible in response to the application of thermal energy thereto in order to hermetically re-seal the stopper after inserting and removing a filling needle or like instrument therethrough.
Figure 8:
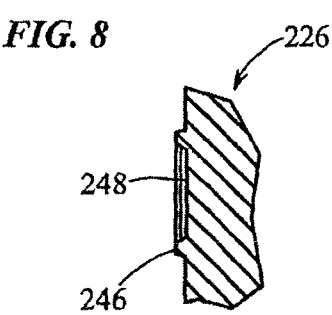
FIG. 8 is an enlarged, partial, cross-sectional view of the resealable portion of FIG. 7 and showing the penetrable portion thereof for receiving a needle or like instrument therethrough.

In the operation of the apparatus 252, and as shown typically in FIG. 9A, each vial is first introduced into the cauterizing station with the penetrable surface region 248 of the resealable portion 226 aligned with the heating surface 264. Then, the drive source 272 is actuated to drive the housing 254 downwardly until the peripheral sealing surfaces 262 sealingly engage the upper flange surface 236 of the respective locking member 234, and the heating surface 264 simultaneously engages the exposed penetrable surface portion 248 of the resealable portion 226. The heated surface 264 is maintained at a predetermined temperature, and is held in contact with the exposed surface portion 248 for a predetermined time period, sufficient to cauterize the exposed surface portion. One advantage of the construction of the resealable portion 226 as shown in FIGS. 7 and 8, is that the cauterization process deforms the annular protuberance 246 into a contour conforming to that of the heated surface, thus allowing an operator (or optical or other automatic sensing system) to visually determine whether each cap has been properly cauterized prior to filling. As shown in FIG. 9c, after cauterizing the exposed surface, the drive source 272 is actuated to drive the housing 254 upwardly and out of engagement with the cap, another vial is moved under the housing, and the process is repeated until all desired vials are cauterized. As described further below, upon exiting the cauterizing station of FIGS. 9A through 9c, the vials are preferably then moved into a filling station to promptly fill the sterilized vials. The cauterization and filling stations are preferably mounted within a sterile enclosure with a laminar gas flow through the enclosure to facilitate maintaining the sterile conditions, as described, for example, in the above-mentioned patent and patent application.

In the embodiment illustrated in FIGS. 9A through 9C, the temperature of the heating surface is within the range of approximately 250° C. to 300° C., and the cycle times (i.e., the time period during which the heating surface is maintained in contact with the exposed surface 248 of the resealable portion) are within the range of approximately 1.0 to 3.0 seconds. The present inventor has determined that these temperatures and cycle times may achieve at least approximately a 6 log reduction in bio-burden testing to thereby effectively sterilize the surface.

Figure 10:
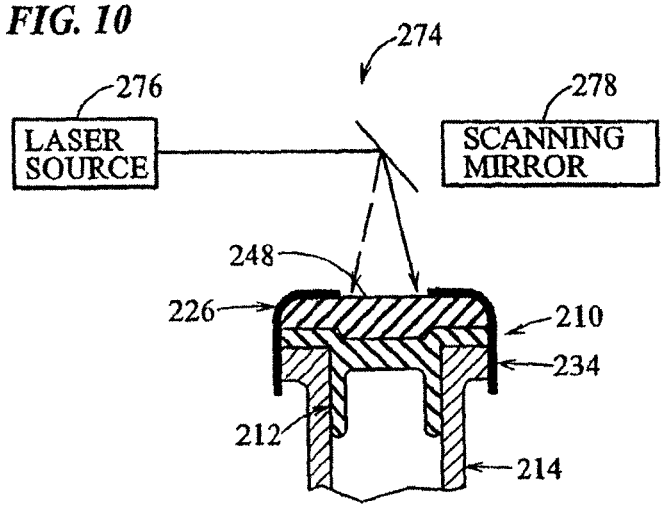
FIG. 10 is a somewhat schematic, partial, cross-sectional view of an apparatus for sterilizing the resealable stoppers of the vials of the present disclosure by laser cauterization prior to introducing the filling needle or like instrument therethrough.

In FIG. 10, an alternative apparatus for cauterizing the resealable caps is indicated generally by the reference numeral 274. The apparatus 274 differs from the apparatus 252 of FIGS. 9A through 9C in that the thermal energy required for sterilizing the filling area of the resealable portion is supplied by a laser (referred to herein as "laser cauterization"). The laser cauterization apparatus 274 comprises a laser or other suitable radiation source 276 optically coupled to a scanning mirror 278 mounted over the vial/cap assembly. Although not shown in FIG. 10, the vials are preferably mounted within the same type of support as shown in FIGS. 9A through 9C in order to allow the resealable caps to be rapidly cauterized in succession prior to filling each vial with medicament, as described further below.

In one embodiment, the laser 276 is a commercially available CO2 or YAG laser. The CO2 laser operates at a wavelength of approximately 10.6 μm. At this wavelength, absorption of the laser energy is governed in part by the electrical conductivity of the material. Therefore, an insulating material, such as the elastomeric material of the resealable portion 226, absorbs and converts most of the incident energy into thermal energy to cauterize the receiving surface 248. The YAG laser operates at wavelength of approximately 1.06 μm. At this frequency, absorption is governed in part by the lattice atoms. Thus, a clear or transparent polymer with little ionization would be permeable to the laser beam. Accordingly, when employing a YAG laser (as with other laser sources, as described below), it is desirable to add a colorant to the elastomeric material of the resealable portion in order to enhance its absorption of the laser energy. With the YAG laser, the superficial layer of the penetrable region of the resealable portion, and any germs, bacteria or other contaminants thereon, are transformed into plasma to rapidly and thoroughly sterilize the effected surface. If necessary, a UV-filtration coating may be applied to the surfaces of the sterile filling enclosure to prevent the operators from receiving any unnecessary UV exposure.

The present inventor has demonstrated that beam energies in the range of approximately 15 to 30 W are sufficient to effectively cauterize the surface 248 of the elastomeric resealable portion. In addition, bio-burden testing has demonstrated that laser energies of approximately 20 W or greater may achieve about a 6.0 log reduction. At these energies, the apparatus may effectively sterilize the surface 248 within a cycle time of approximately 0.5 seconds. Accordingly, a significant advantage of the laser cauterization apparatus and method is that they may involve significantly shorter cycle times than various direct heat methods. Yet another advantage of laser cauterization, is that it involves both a non-contact method and apparatus, and therefore there is no need to be concerned with the cleaning of a contact head or like heating surface.

Figure 11:
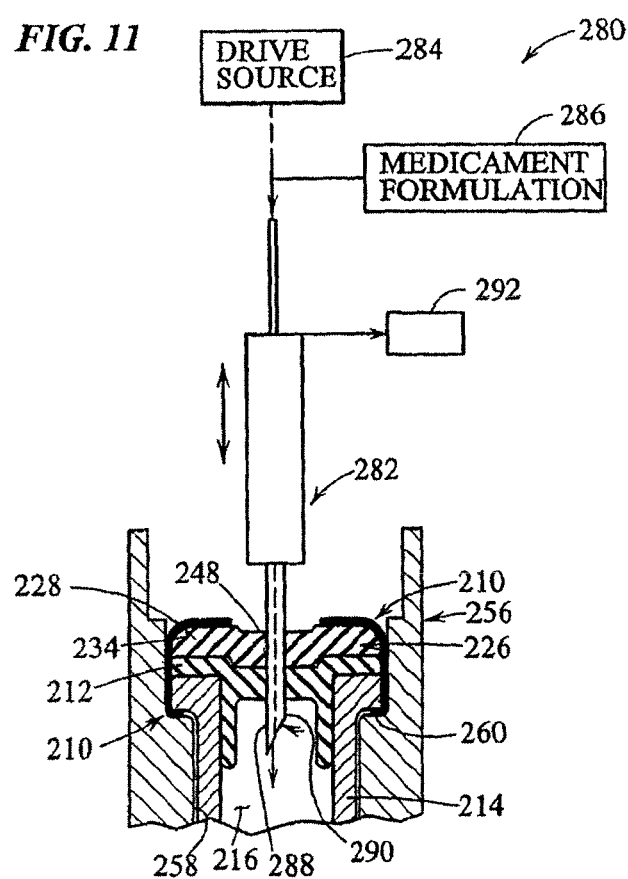
FIG. 11 is a somewhat schematic, partial, cross-sectional view of an apparatus for needle filling the vial assemblies of the present disclosure with a predetermined medicament or other substance to be contained therein.

Turning to FIG. 11, after direct heat or laser cauterization of the resealable portion 226 of each vial, the vial is moved within the support 256 (such as by vibratory drive) into a filling station 280. The filling station 280 includes a needle or like injection member 282 reciprocally mounted over the support 256, as indicated by the arrows in FIG. 11, and axially aligned with the penetrable region 248 of the resealable portion 226 of each vial assembly passing therethrough. A drive source 284 is drivingly connected to the needle 280 for reciprocally driving the needle 282 into and out of engagement with each cap or stopper 210. A medicament or other formulation reservoir 286 is coupled in fluid communication with the needle 282 for introducing a predetermined medicament or other formulation through the needle and into the vial. In the illustrated embodiment, the needle 282 defines a plurality of fluid conduits therein, including a first fluid conduit 288 for injecting the predetermined medicament or other formulation into the vial, as indicated by the arrow in FIG. 11, and a second fluid conduit 290 coupled in fluid communication with a vacuum source 292 for withdrawing air or other gases from the interior cavity 216 of the vial prior to and/or during the filling of the cavity with the medicament or other formulation. In the illustrated embodiment, the needle 282 is a "double lumen" needle, defining a central fluid conduit 288 for injecting the predetermined medicament or other formulation into the vial, and an outer annular fluid conduit 290 for drawing the displaced air or other gases out of the interior cavity of the vial. Alternatively, the outer fluid conduit 290 of the double-lumen needle may be defined by one or more axially-elongated grooves formed in the outer wall of the needle that form fluid-flow passageways between the needle and the pierced portion of the resealable stopper. As may be recognized by those of ordinary skill in the pertinent art based on the teachings herein, the needles used to needle fill the vial assemblies of the present invention may take any of numerous different shapes and/or configurations that are currently known, or later become known for performing the functions of the needles as described herein.

As shown in FIGS. 12a through 12d, after filling the vial with the medicament or other formulation and withdrawing the needle 282 from the cap or stopper 210, the penetrated region of the cap defines a needle hole 294 along the path of the withdrawn needle (FIG. 12b). Upon withdrawing the needle, the vulcanized rubber base 212 of the stopper is sufficiently resilient to close upon itself in the penetrated region and thereby maintain the vial in a sealed condition. However, as described above, vapors, gases and/or liquid may be allowed over time to pass through the needle hole of the vulcanized rubber base, and therefore each vial/cap assembly is passed through a sealing station, as shown typically in FIG. 12c, to heat seal the resealable portion 226 of the cap promptly after withdrawing the needle therefrom. As shown typically in FIG. 12c, a heated member or surface 264 may be reciprocally mounted over, and axially aligned with the penetrable region 248 of the vial/cap assembly received within the filling station. A drive source 272 is drivingly connected to the heated member 264 to reciprocally drive the heated member into and out of engagement with the resealable portion of each cap. As shown typically in FIG. 12c, the heated member 264 is maintained at a sufficient temperature, and maintained in engagement with the penetrated region of the resealable portion 226 to fuse the elastomeric material and hermetically seal the needle hole 294. As a result, and as shown typically in FIG. 12d, the needle hole is eliminated from the exterior region of the resealable portion to thereby maintain a hermetic seal between the cap and vial.

As may be recognized by those skilled in the pertinent art based on the teachings herein, the drive source and heating member/surface of FIGS. 12a through 12d may take the form of any of numerous different drive sources and heating members as described above. As indicated typically in FIG. 12c, however, the heating member 264 may define a smaller width than the heating member/surface described above for cauterizing the penetrable region of the cap prior to filling. In addition, the temperature of the heating member 264 for sealing may be higher than that of the heating member described above in order to rapidly melt and seal the penetrated region. One advantage of resealable stoppers is that the base thermally insulates the heated region from the medicament in the vial to thereby maintain the medicament in the vial within an appropriate temperature range throughout the cauterization and heat sealing processes and thereby avoid any thermal damage to the medicament.

Alternatively, and as shown in FIGS. 13A through 13C, the laser source 276 and scanning mirror 278 may be employed to heat seal the penetrated region 294/248 of the resealable portion. Accordingly, the same type of laser source 276 and scanning mirror 278 as described above may be employed in the heat sealing station to perform this function, or alternatively, a different type of laser system may be employed. In one embodiment, a CO2 laser of approximately 50 W is employed to seal a region approximately 0.10 inch in diameter in the resealable stopper.

In some embodiments of the present disclosure, each sealable cap or stopper is formed of a thermoplastic material defining a needle penetration region that is pierceable with a needle to form a needle aperture therethrough, and is heat resealable to hermetically seal the needle aperture by applying laser radiation at a predetermined wavelength and power thereto. As described further below, each cap or stopper includes a thermoplastic body or body portion defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region and/or the cover portion of the stopper (i.e., without creating an irreversible change in molecular structure or chemical properties of the material). In some embodiments, the predetermined time period is approximately 2 seconds, and is preferably less than or equal to about 1.5 seconds. In some of these embodiments, the predetermined wavelength of the laser radiation is about 980 nm, and the predetermined power of each laser is preferably less than about 30 Watts, and preferably less than or equal to about 10 Watts, or within the range of about 8 to about 10 Watts. Also in some of these embodiments, the predetermined color of the material is gray, and the predetermined opacity is defined by a dark gray colorant added to the stopper material in an amount within the range of about 0.3% to about 0.6% by weight.

In addition to the thermoplastic materials described above, the thermoplastic material may be a blend of a first material that is preferably a styrene block copolymer, such as the materials sold under either the trademarks KRATON or DYNAFLEX, such as DYNAFLEX G2706-10000-00, and a second material that is preferably an olefin, such as the materials sold under either the trademarks ENGAGE or EXACT, such as EXACT 8203. In some embodiments of the invention, the first and second materials are blended within the range of about 50:50 by weight to preferably about 90:10 by weight, and most preferably about 90:5 by weight (i.e., first material:second material). The benefits of the preferred blend over the first material by itself are improved water or vapor barrier properties, and thus improved product shelf life; improved heat sealability; a reduced coefficient of friction; improved moldability or mold flow rates; and a reduction in hysteresis losses.

Alternatively, the thermoplastic material of the resealable stoppers may take the form of a styrene block copolymer sold by GLS Corporation of McHenry, Ill. under the designation LC 254-071. This type of styrene block copolymer compound exhibits approximately the following physical properties: (i) Shore A Hardness: about 28-29; (ii) Specific Gravity: about 0.89 g/cm3; (iii) Color: approximately grey to dark grey; (iv) 300% Modulus, flow direction: about 181-211 psi; (v) Tensile Strength at Break, flow direction: about 429-498 psi; (vi) Elongation at Break, flow direction: about 675%-708%; and (vii) Tear Strength, flow direction: about 78-81 lbf/in. In one embodiment, the predetermined color and opacity of the thermoplastic is defined by a grey colorant that is provided in an approximately 3% color concentrate (i.e., there is an approximately 33:1 ratio of the concentrate to the natural resin or TPE). The color concentrate contains about 88.83% carrier or base resin, and the remainder is pigment. In one embodiment, the pigment is grey carbon black. Thus, the pigment is about 0.34% by weight of the resulting thermoplastic.

In addition, if desired, a lubricant of a type known to those of ordinary skill in the pertinent may be added to the thermoplastic compound, such as the aforementioned styrene block copolymer compound, in order to prevent or otherwise reduce the formation of particles upon penetrating the needle penetration region of the thermoplastic portion with a needle or other filling member. In one embodiment, the lubricant is a mineral oil that is added to the styrene block copolymer or other thermoplastic compound in an amount sufficient to prevent, or substantially prevent, the formation of particles upon penetrating same with the needle or other filling member. In another embodiment, the lubricant is a silicone, such as the liquid silicone sold by Dow Corning Corporation under the designation "360 Medical Fluid, 350 CST," that is added to the styrene block copolymer or other thermoplastic compound in an amount sufficient to prevent, or substantially prevent, the formation of particles upon penetrating same with the needle or other filling member.

Each of the vials of the present invention may be made of any of numerous different materials that are currently, or later become known for making vials. For example, in some embodiments of the present invention, the vials are made of glass. In one such example, the vial body is made of glass; however, a laterally extending base is made of plastic, and is secured to the base of the glass vial body by an adhesive, snap-fit, over-molding, or other known joining mechanism, and the locking ring likewise is made of plastic and is secured to the open end of the vial body by an adhesive, snap-fit, over-molding, or other known joining mechanism. In other currently-preferred embodiments of the present invention, the vial bodies are made of a thermoplastic material, such as the thermoplastic material sold under the trademark TOPAS by Ticona Corp. of Summit, N.J. In some embodiments of the present invention, the TOPAS™ material is sold under any of the following product codes: 5013, 5513, 6013, 6015, and 8007, and is a cyclic olefin copolymer and/or cyclic polyolefin.

As may be recognized by those skilled in the pertinent art based on the teachings herein, the specific formulations of the polymeric compounds used to form the stoppers and the vials or other containers of the present invention can be changed as desired to achieve the desired physical characteristics, including sorption (both absorption and adsorption), and moisture-vapor transmission ("MVT"). For example, the wall thicknesses of the vials and/or stoppers can be increased or otherwise adjusted in order to provide an improved or otherwise adjusted MVT barrier. Alternatively, or in conjunction with such measures, the blend of components forming the thermoplastic compounds may be changed as desired to meet desired sorption levels with the particular product(s) to be contained within the vial, and/or to achieve desired MVT characteristics. Still further, in those embodiments of the resealable stopper of the present invention employing multiple layers of fusible and infusible materials, the relative thicknesses of the different materials can be adjusted to, in turn, adjust the MVT characteristics of the stopper. In addition, as described further below, a tamper-resistant or other cover, that may include a frangible or like portion that is removable immediately prior to use of the vial to expose the resealable stopper, can form a hermetic or gas-tight seal between the needle penetrable surface of the stopper and the ambient atmosphere, to further improve the MVT barrier to medicament or other substance contained within the vial. As also may be recognized by those of ordinary skill in the pertinent art based on the teachings herein, the above-mentioned numbers and materials are only exemplary, and may be changed as desired or otherwise required in a particular system.

Figure 14A:
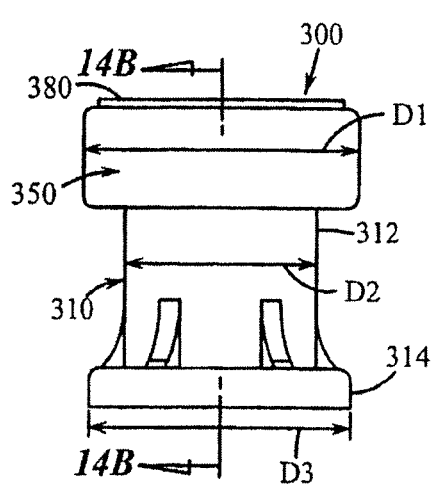
FIG. 14A is a side elevation view of a vial embodying the present disclosure.
Figure 14B:
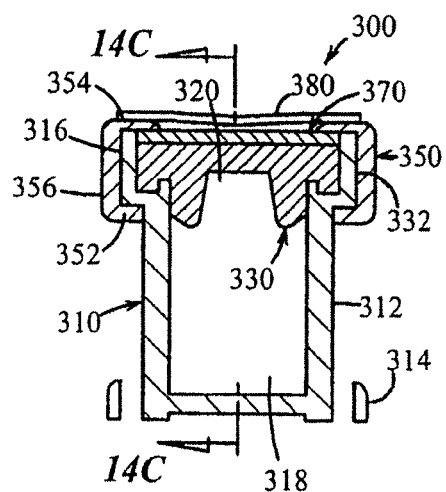
FIG. 14B is a cross-sectional view of the vial of FIG. 14A taken along line 14B-14B and illustrating a three-piece closure assembly partially inserted into the mouth of the vial, wherein the closure assembly includes a stopper, a heat-resealable portion and an over-molded securing or locking ring.
Figure 14C:
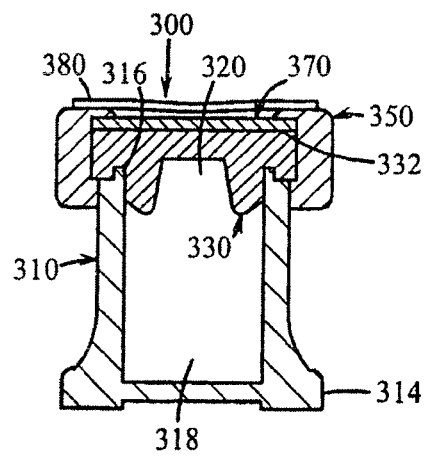
FIG. 14C is a cross-sectional view of the over-molded vial of FIG. 14 taken along line 14C-14C thereof, wherein the vial has a relatively enlarged base portion.

Referring now to FIGS. 14A through 14C, a further embodiment of an assembled medicament vial constructed in accordance with the inventive aspects of the present disclosure is designated generally by reference numeral 300. Vial assembly 300 includes, among other things, a storage vial 310, a stopper member 330, a securing ring 350 and a heat resealable disc 370.

Storage vial 310 includes a body 312, a base 314 and a neck 316. Body 312 defines an interior chamber 318 that is adapted for storing a predetermined medicament or other substance to be contained therein. As shown herein, body 312 is substantially cylindrical in shape. However, those skilled in the art would readily appreciate that body 312 can be spherical or any other shape conducive to defining an interior chamber suitable for the storage of medicaments or other substances. Neck 316 is associated with the top of body 312 and defines a vial mouth 320. In the currently preferred embodiments, medicament flow into and out of the interior chamber 318 is through a needle (both directions).

Stopper member 330 is inserted into mouth 320 and includes an outer peripheral surface 332 which is adapted and configured for insertion into mouth 320 and for engagement with neck 316 of storage vial 310. The stopper member 330 provides a first primary seal for containing the predetermined medicament within the interior chamber 318 of storage vial 310. Stopper member 330 may be formed of vulcanized rubber. However, those skilled in the art to which this application appertains would readily appreciate that other suitable materials may be used for stopper member 330.

Heat-resealable portion 370 is also inserted into the mouth 320 of storage vial 310 and preferably completely overlies stopper member 330. As described above with respect to the other embodiments of the resealable stopper, heat-resealable portion 370 is preferably made of a resilient polymeric material, such as a blend of a first polymeric material sold by Shell Oil Co. under the registered trademark KRATON® or DYNAFLEX®, and a second material in the form of a low-density polyethylene, such as the polyethylene sold by Dow Chemical Co. under the trademarks ENGAGE™ or EXACT™. In one embodiment, the first and second materials are blended within a range of about 50:50 by weight to about 90:10 by weight (i.e., first material:second material). In another embodiment, the blend of the first and second materials is about 50:50 by weight. The benefits of the preferred blend over the first material by itself are improved water or vapor barrier properties, and thus improved product shelf life; improved heat sealability; a reduced coefficient of friction; improved moldability or mold flow rates; and a reduction in hysteresis losses. As may be recognized by those skilled in the pertinent art, these numbers and materials are only exemplary, however, and may be changed if desired or otherwise required in a particular system.

An important feature of the heat-resealable portion 370 is that it can be resealed to form a gas-tight seal after inserting a needle, syringe or like injection member therethrough. Preferably, the resealable portion can be sealed by heating the area punctured by the needle in the manner described above. One advantage of the blended polymer described above is that it minimizes the degree to which the medicament can be absorbed into the polymer in comparison to either KRATON® or DYNAFLEX® itself.

With continuing reference to FIGS. 14A through 14C, securing ring 350 is shown engaged with the neck 316 of the vial 300 and is adapted and configured for retaining the heat-resealable portion 370 and the stopper member 330 within the vial mouth 320 and effectuating a second seal. The securing ring 350 is formed preferably from at least one of a thermoplastic and elastic material. The securing ring can be formed from a resilient polymeric material and a low-density polyethylene, similar to that used in the heat-resealable portion 370. Preferably, the securing ring 350 is formed by inserting the storage vial 310/stopper member 330 assembly into a molding apparatus and then molding the securing ring material directly over a portion of the storage vial 310 and stopper member 330 (referred to as "over-molding").

As noted above, it is difficult to maintain the sterility of caps and vials during the transportation, storage and assembly process. The use of a non-metallic material for securing ring 350 allows the vial and cap to be assembled and then sterilized as a unit prior to filling the vial assembly with medicament by using, for example, a gamma sterilization technique or other irradiation or sterilization process. Unlike threaded plastic caps, an over-molded securing ring provides a mechanism for ensuring that the vial has not been compromised and prevents the stopper from being removed.

As shown in FIG. 14b, securing ring 350 defines a somewhat C-shaped cross-section having a web 356 that separates a lower flange 352 and an upper flange 354. The securing ring 350 is formed so that lower flange 352 is engaged with shoulder 322 of storage vial 310. Additionally, upper flange 354 partially overlies stopper member 330 and heat-resealable portion 370 and thereby secures these elements within the mouth 320 of vial body 310.

During the over-molding process, if desired, the material used to form the securing ring 370 can be provided to the mold at a temperature that is sufficient to partially melt in the region of interface of the neck 316 of the vial and/or the heat-resealable disc 370 or stopper member 330. As a result, upon the cooling of the materials, the securing ring 370 is effectively fused with the neck 316 of the vial and/or the heat-resealable portion 370 or stopper member 330. The fusing of the materials further enhances the sealing and retaining function of securing ring 350. Partial fusion of one or more of the elements as described also is advantageous in vials having a relatively large diameter mouth, since the insertion of a needle into a stopper tends to push the stopper into the interior chamber. If necessary, the fusing of the securing ring with the stopper or heat-resealable portion may facilitate preventing the collapse of the stopper. It should be noted that the fusion of the materials can be accomplished by ultrasonic welding, by applying thermal energy or by using any other known technique for joining thermoplastics, elastics or other materials employed.

It is presently envisioned that in an alternate embodiment, the heat-resealable disc can be removed and the securing ring can be formed so that it completely overlies the stopper member. In this embodiment, the securing ring could be formed of heat-resealable material that is the same as or similar to that described for disc 370 or otherwise described above. In operation, the stopper member and the securing ring would be penetrable by a needle or like filling member for the introduction of medicament into the interior chamber of the vial. Upon withdrawal of the filling needle, thermal energy would be applied to the securing ring for hermetically sealing any hole created by the filling needle.

With continuing reference to FIGS. 14A through 14C, vial assembly 300 further includes a peel back cover 380. Cover 380 is adhered to sealing ring 350 subsequent to the filling and resealing processes and provides a tamper-proof seal which signifies whether medicament has been withdrawn or the vial tampered with subsequent to the filling process and vial storage. In addition, if necessary or otherwise desired, the peel back cover can provide a further barrier to moisture and/or vapor transmission into or out of the interior of the vial.

As shown in FIG. 14A, the vial 310 defines a spool-like or diabolo shape. More specifically, the upper portion or securing ring 350 defines a first laterally-extending dimension or diameter "D1," the vial body 312 defines a second laterally-extending dimension or diameter "D2," and the base 314 defines a third laterally extending dimension or diameter "D3". As can be seen, both D1 and D3 are greater than D2, thus forming a diabolo or spool-like shape. As described above, this shape facilitates handling during use by permitting the user to grasp the reduced diameter D2 of the vial body with, for example, an index finger and thumb of one hand. The relatively larger diameter D1 of the upper portion and relatively larger diameter D3 of the base facilitate a user's ability to secure the vial against axial movement. Further, the relatively larger diameter D1 of the upper portion facilitates in preventing needle sticks by guarding a user's fingers in the event the needle slips or otherwise misses the stopper. In addition, as described further below, the diabolo or spool-like shape can cause the vial to define a lower center of gravity than other prior art vials, and thus better prevent tipping of the vial during handling in, for example, an automated filling machine. As also described further below, the diabolo or spool-like shape facilitates in securing and otherwise handling the vial during automated sterilization, needle filling and/or thermal resealing of the vial.

Figure 15:
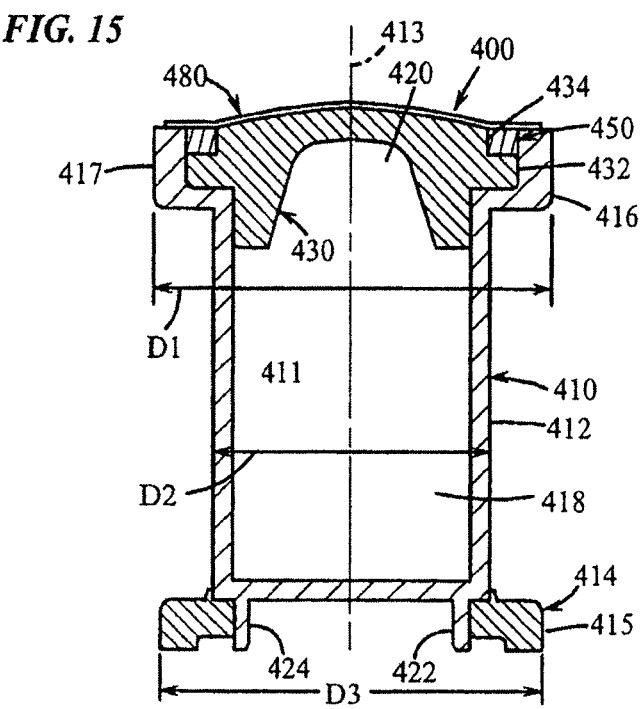
FIG. 15 is a cross-sectional view of another vial embodying the present disclosure, and including a closure or cap wherein the over-molded securing ring is formed in an annular recess defined between the outer periphery of the stopper and the vial body.

Referring now to FIG. 15, another vial assembly constructed in accordance with a representative embodiment of the present disclosure is designated generally by reference numeral 400. Vial assembly 400 includes, among other things, a storage vial 410, a stopper member 430, and a securing ring 450. Storage vial 410 has a cylindrical body 412 which interconnects a base 414 and a neck 416. The body 412 has an outer wall 411 that defines an interior chamber 418 for storing a predetermined medicament and a central axis 413 for vial assembly 400.

Unlike vial 300, in which base 314 and body 312 are formed as a unit, the base 414 and the body 412 of storage vial 410 are formed independently. Base 414 includes an inner surface 422 which is adapted and configured for engagement with an axially depending flange 424 of storage vial 410. The base 414 can be engaged with the body 412 by means of a press-fit relationship, adhesion, ultrasonic welding or any other joining technique. Due to its width, and as with the base of the vial 300 as described above, the base 414 increases the vertical stability of vial assembly 400 when placed on a horizontal surface.

With continuing reference to FIG. 15, in the embodiment shown herein, stopper member 430 has an annular groove 434 defined in outer periphery 432. When stopper member 430 is inserted into the mouth 420 of storage vial 410, an annular recess is formed between stopper member 430 and the neck 416 of storage vial 410. Securing ring 450 is formed in this recess preferably in the manner hereinafter described.

Figure 16A:
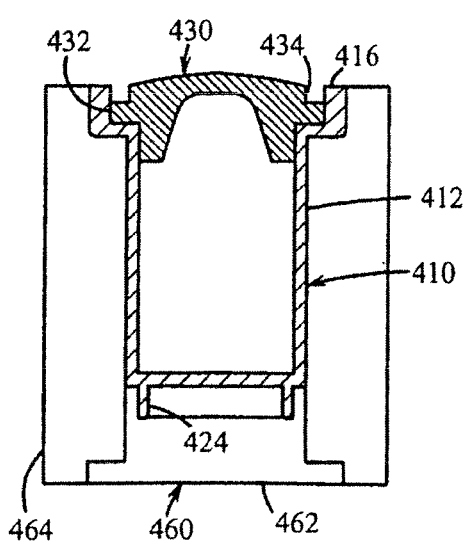
FIGS. 16A and 16B illustrate representative sequential views of an exemplary over-molding process for making over-molded vials embodying the present disclosure.
Figure 16B:
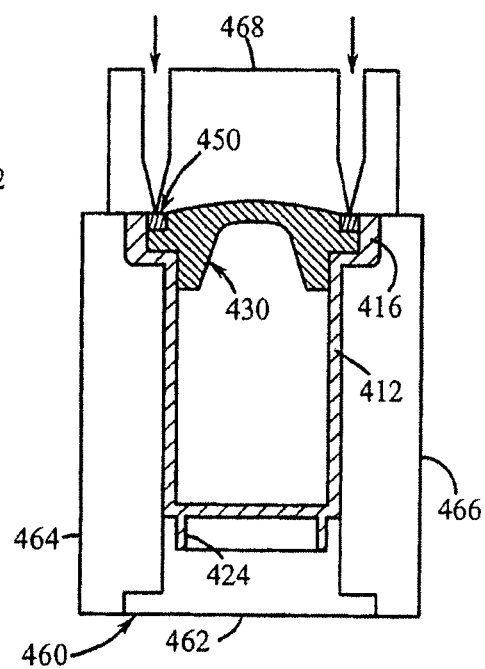

Referring now to FIGS. 16A and 16B, a representative process for forming securing ring 450 is illustrated. As shown in FIG. 16A, vial body 412 is first placed within a cavity defined by lower mold assembly 460. For ease in manufacturing, base 414 has not yet been engaged with flange 424 of vial body 412. Mold assembly 460 includes a bottom 462 and first and second sidewalls 464 and 466, respectively.

Stopper member 430 is then inserted into the mouth of vial body 412. As noted above with respect to FIG. 15, stopper member 430 has an annular groove 434 defined in its outer periphery 432. When stopper member 430 is inserted into the mouth of vial body 412, an annular recess is formed between stopper member 430 and the neck 416 of storage vial 410. Alternatively, to reduce the potential for particulate contamination, vial body 412 and stopper member 430 can be formed in side-by-side molds in a clean room environment. The stopper member 430 can be inserted into the mouth of the vial body 412 prior to the transfer out of the clean room environment and to mold assembly 460 thereby preventing particulate from accumulating in the interior chamber 418.

Next, as shown in FIG. 16*b*, upper mold element 468 is positioned over lower mold assembly 460. Securing ring 450 is then formed by injecting (indicated by the flow arrows) at least one of a thermoplastic and elastic material in liquefied form into the annular recess. During the molding process, and when the vial body is formed of a plastic material (as opposed to glass, for example) the temperature of the material used to form securing ring 450 is sufficient to partially melt on contact the adjacent material of neck 416. Therefore, upon cooling, securing ring 450 is partially fused with neck 416 so as to retain stopper member 430 within the vial mouth. It should be noted that the fusion can be achieved by ultrasonic welding, by applying thermal energy or by any other known technique for joining thermoplastics, elastics, or other materials employed.

A closure for a vial manufactured in accordance with the method detailed in FIGS. 16A and 16B includes a sealing ring formed by injecting liquefied ENGAGE™ polyolefin into the annular recess defined between the stopper and the vial neck at a temperature in excess of about 390° F. The stopper is made from a thermoplastic comprising a blend of ENGAGE™ and DYNAFLEX™ in the manner described above. The temperature of the liquefied ENGAGE™ is sufficient to locally melt the thermoplastic stopper as well as the vial neck. Upon cooling of the materials, air may be supplied to the interior chamber through an aperture drilled or otherwise formed in the bottom of the vial body. Applicant has determined that the interior chamber may be pressurized in excess of about 80 psi without dislodging the closure formed by the stopper and securing ring from within the vial mouth.

Referring now to FIGS. 17A through 17C, a representative process for making a vial assembly in accordance with the present disclosure is illustrated. Vial assembly 500 includes a storage vial 510, an over-molded stopper 530 and an over-molded base 580. Storage vial 510 is structurally similar to storage vials 310 and 410 described above, except that storage vial 510 has both an open top and an open bottom end.

As with the vial 310 described above, and as shown in FIG. 15, the vial 410 defines a diabolo or spool-like shape formed by the relatively larger diameters D1 of the upper portion 417 and D3 of the base 415, and the relatively smaller diameter D2 of the body 412 extending axially between the upper portion and base.

As shown in FIG. 17A, storage vial 510 is first positioned within a cavity partially defined by mold assembly 560. Mold assembly 560 includes bottom portion 562, first and second sidewalls 564 and 566, respectively, and upper portion 568. Bottom portion 562 of mold assembly 560 has a cylindrical mold insert 570 projecting therefrom and into storage vial 510. An upper surface 572 of mold insert 570 is adapted and configured for defining a lower surface for over-molded stopper 530. Over-molded stopper 530 is formed by injecting at least one of a thermoplastic and elastic material in liquefied form into the cavity defined by the molding elements.

Upon the formation of stopper 530, the vial body 510 with over-molded stopper 530 is removed from the mold. As shown in FIG. 17B, a base member 514 is engaged with the bottom of storage vial 510 by any of the methods described above. Lastly, the assembled vial is positioned within a second mold assembly (not shown) and an over-molded base 580 is formed in a manner similar to the previously described over-molding process.

Figure 18:
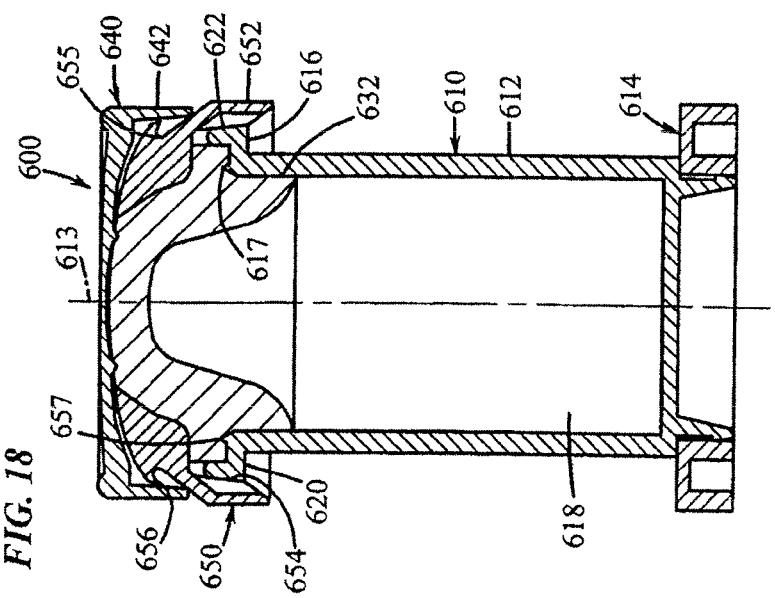
FIG. 18 is a cross-sectional view of another vial embodying the present disclosure wherein the base and locking ring are snap fit to the vial body, and the tamper-resistant cover is snap fit to the locking ring.
Figure 23:
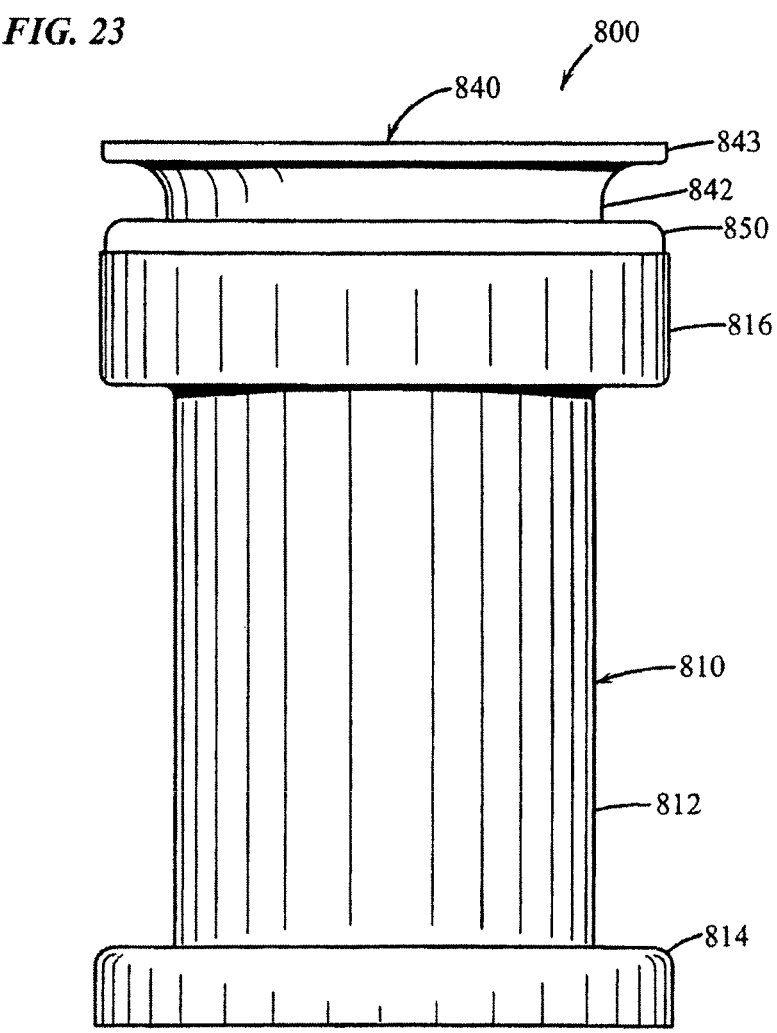
FIG. 23 is a side elevation view of another vial embodying the present disclosure wherein the locking ring, cover and base are connected together by ultrasonic welding.

Referring now to FIG. 18, another vial assembly constructed in accordance with a representative embodiment of the present disclosure is designated generally by reference numeral 600. Similarly to the previously described embodiments, vial assembly 600 includes a storage vial 610 and a stopper member 630. Storage vial 610 has a cylindrical body 612, a snap-on base 614 and a neck 616. Body 612 defines an interior chamber 618 for storing a predetermined medicament and a central axis for vial assembly 600.

As described above, stopper member 630 includes an outer peripheral surface 632 which is adapted and configured for engagement with the neck 616 of storage vial 610. Peripheral surface 632 of stopper member 630 provides a first primary seal for containing the predetermined medicament within the interior chamber of vial body. As can be seen, the neck 616 of the vial defines a pointed annular protuberance 617 that projects axially into the overlying stopper material to thereby further effectuate a hermetic seal between the stopper and vial. In contrast to the previously described embodiments, vial assembly 600 further includes a locking or securing ring or locking ring 650 and a snap-off, tamper-resistant cover 640. Locking ring 650 has an outer peripheral flange 652 that defines a shoulder 654 on an inner surface thereof. Shoulder 654 is adapted and configured for interlocking engagement with lower surface 620 of neck 614. Locking ring 650 is made from a relatively flexible, non-metallic material, such as plastic.

During the assembly process, locking ring 650 is positioned over stopper member 630. Locking ring 650 is pressed axially downward so as to compress and retain stopper member 630 within the mouth of the vial. The flexibility and configuration of flange 652 of the locking ring allows the flange to flex radially outward of outer peripheral surface 622 of neck 614. Once shoulder 654 passes axially downward beyond lower surface 620, the flange 652 flexes back and shoulder 654 and lower surface 620 form a snap-fit, interlocking engagement. In a representative embodiment, an annular recess is scored or otherwise formed in the outer surface of flange 652 after the locking ring 650 is engaged with neck 614 of storage vial 610. As can be seen, locking ring 650 can not be disengaged from neck 614 without breaking flange 652. This feature functions to prevent removal of the stopper and any tampering with the contents of the vial without piercing the stopper.

Locking ring 650 defines a central aperture that allows stopper member 630 to be accessed therethrough by a needle or like device. Tamper-resistant cover 640 is configured to overlie the central aperture of locking ring 650 and engage with locking ring 650, thereby protecting the exposed stopper material. In the embodiment shown herein, cover 640 is engaged with locking ring 650 by means of a press-fit similar to that previously described for the locking ring 650. Cover 640 includes an outer peripheral flange 642 that defines a shoulder 655 on an inner diameter thereof which is adapted for interlocking engagement with peripheral recess 656 associated with locking ring 650. Tamper-resistant cover 640 further defines on its underside a pointed annular protuberance 657 that is pressed into engagement with the adjacent stopper material to thereby effectuate a hermetic seal between the cover 640 and stopper 630. Preferably, tamper-resistant cover 640 cannot be removed from the vial without breaking the cover, thus providing a further tamper-resistant feature. Alternatively, this tamper-resistant feature can be created by using ultrasonic welding, adhesion, or any other connection technique to engage tamper-resistant cover 640 with locking ring 650 so that once removed, cover 640 can not be re-engaged with locking ring 650.

As may be recognized by those of ordinary skill in the pertinent art based on the teachings herein, the vial may be made of glass, plastic, or a combination of glass and plastic. For example, the vial body may be made of glass, whereas the base 614 may be made of plastic, and the locking ring 650 and tamper-resistant ring may be made of plastic. The plastic base and locking ring may be attached to the glass vial body in any of the numerous different ways described herein, including by over-molding the plastic component onto the glass component, by mechanical snap-fit or other interlocking engagement between the plastic component and the glass component, or by adhesively joining the plastic component to the glass component. In addition, in this embodiment of the invention, the stopper may include a vulcanized rubber or other infusible base portion, and a thermoplastic or other thermally fusible portion overlying the base portion that is thermally fusible in the manner described above. One advantage of this type of embodiment of the present invention, is that the medicament or other substance contained within the vial is exposed to, or stored in contact with only the glass and vulcanized rubber surfaces. Thus, this type of embodiment may be easily used with medicaments or other substances that are were in the past stored in glass vials with vulcanized rubber or like stoppers.

In FIGS. 22A, 22B and 22C, the cover 640 is illustrated in further detail and includes a frangible portion 660 connected to the remainder of the cover by a plurality of radially-spaced frangible connections 662. As can be seen, in order to access the resealable stopper 630 with a needle or like device, the frangible portion 660 must be flipped away from the stopper with sufficient force to break the frangible connections 662 and thus permit release of the frangible portion 660 therefrom. As can be seen, the cover 640 may define a peripheral rim 664 that is engageable by a user's thumb, for example, to press and, in turn, break away the frangible portion 660. Once the frangible connections 662 are broken, the frangible portion 660 cannot be reattached, thus providing a tamper-proof feature. In addition, the annular protuberance 657 and associated portion of the cover overlying the stopper material within the central aperture of the locking ring 650 further seals the stopper and interior portions of the vial from the ambient atmosphere, and thus further prevents the exposure of ambient gases, vapors or other unwanted substances to either the stopper or the substances contained within the vial. For example, the cover 640 can significantly improve the vapor (or MVT) barrier provided by the stopper assembly and thereby increase the effective shelf-life of the substances contained within the vial.

One of the advantages associated with the vial assembly 600, as well as vial assemblies 300, 400, and 500, is that they are configured to be spool-shaped or diabolo-shaped. As described above, the upper and lower portions of the vial assemblies have outer peripheral surfaces which are positioned radially outward of the central vial body. As a result, during the withdrawal of the medicament by the healthcare worker, the fingers that grasp the recessed vial body are protected and are less likely to be pierced by a needle that has slipped off of the stopper.

Configuring the vial assembly so as to be diabolo-shaped also improves the stability of the filled vials, as well as the handling of the vials during the sterilization and filling processes. A vial with a base that has an outer peripheral surface positioned radially outward of the central vial body has a lower center of gravity than a traditional blow molded vial of the same height with a base that does not protrude radially from the vial body. The protrusion of the upper and lower portions beyond the outer diameter of the vial body also improves the handling of the vial body or assembly by providing upper and lower shoulders which can be used to guide the vial during the handling process and facilitate the use of automated handling equipment (e.g., pick and place robotics).

A further advantage of the vial assemblies described herein is that the tamper-resistant covers may be hermetically sealed to the underlying locking members and/or the resealable stoppers to thereby seal the stoppers within the locking members and covers and with respect to the ambient atmosphere. In accordance with one aspect of a preferred embodiment of the present invention, the overlying locking members and covers can be formed of relatively rigid materials and/or of materials having relatively high resistances to moisture and vapor transmission in comparison to the material of the resealable stopper itself, in order to facilitate preventing the loss of any medicament or other substance contained within the vial or other container therethrough, or the ingress of moisture or vapor into the vial or other container, during, for example, storage, transportation and/or product shelf life.

Figure 19:
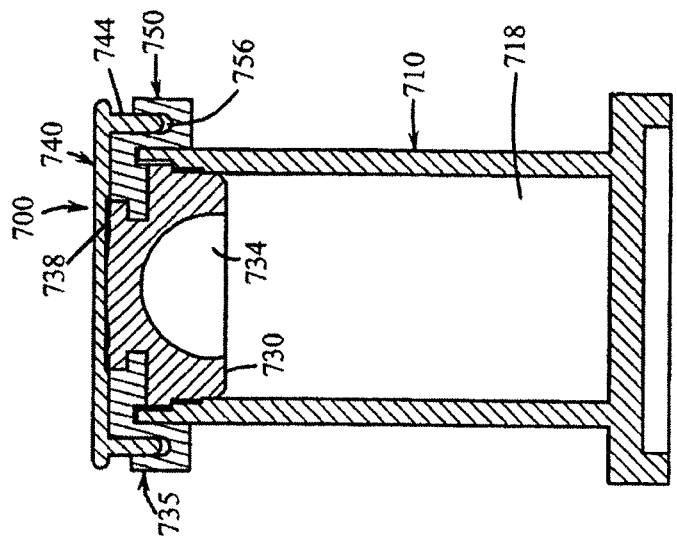
FIG. 19 is a cross-sectional view of another vial embodying the present disclosure wherein the stopper and securing ring are formed using a sequential molding process.

With reference to FIGS. 19 through 21, there is illustrated another vial assembly 700 constructed in accordance with inventive aspects of the present disclosure. Vial assembly 700 includes, among other features, a closure assembly 735 and a vial body 710. Similar to the closure assembly of FIG. 18, closure assembly 735 is a three-piece assembly comprising a stopper member 730, a locking or securing ring or cap 750 and a tamper-resistant cover 740.

Unlike the closure assembly of FIG. 18, closure assembly 735 is formed partially by a sequential molding process. More specifically, the stopper 730 (FIG. 20) and the locking ring 750 are formed as a unit by a two-step molding process. The stopper 730 is first fabricated by any known molding process. As shown in FIG. 20, the outer periphery 732 of stopper 730 includes an annular recess 736. Stopper 730 is then placed in a mold assembly and is used to define at least a portion of the inner surface 752 of locking ring 750. A thermoplastic or elastic is injected into the mold so as to form locking ring 750 having an annular protrusion 754 that is engaged within the annular recess 736 of stopper 730.

Then, as shown in FIG. 19, the unitized stopper/locking ring is engaged with the open end of vial body 710 so as to seal interior cavity 718.

Locking ring 750 includes an annular groove 756 formed along its outer periphery. As shown in FIG. 19, tamper-resistant cover 740 includes an outer peripheral flange 744 depending therefrom. Flange 744 is slidably engaged within groove 756 of locking ring 750 and secures cover 740 to locking ring 750. When the tamper-resistant cover 740 is pressed into engagement with locking ring 750, annular rib 738 of stopper 730 is compressed by the bottom of the cover and a second hermetic seal is thereby formed. Accordingly, the tamper-resistant cover 740 forms a hermetic or gas-tight seal between the exterior surface of the stopper and the ambient atmosphere, thereby providing a further MVT barrier between the interior of the vial and the ambient atmosphere. As may be recognized by those of ordinary skill in the pertinent art based on the teachings herein, the material(s) and/or thickness of the tamper-resistant cover 740 and/or of the locking ring 750, or at least the portion(s) of the cover and/or locking ring that overly and seal the exposed surface(s) of the stopper, may be selected to control the MVT barrier between the interior and exterior of the vial in the direction through the stopper.

The annular groove 756 formed along the outer periphery of locking ring 750 also functions to reduce the likelihood of an accidental needle stick. In order to access stopper 730, for the purpose of removing medicament from within interior chamber 718, cover 740 is disengaged from locking ring 750 exposing groove 756. If by chance the needle being used to withdraw the medicament accidentally slips off of or relative to the stopper 730, the needle will likely slide into annular groove 756 rather than continue in a downward trajectory and potentially pierce the hand of the healthcare worker.

With continuing reference to FIGS. 19 and 20, cavity 734, which is defined in the bottom of stopper 730, allows the upper portion of the stopper 730 to flex upon the application of force to annular rib 738 by cover 740. As a result, the lower portion of the stopper member is forced radially outward and the circumferential seal created between the outer periphery 732 of the stopper 730 and the vial body 710 is improved. Additionally, the upper portion of stopper 730 is radially compressed as a result of the forces applied to annular rib 738, forming a hermetic or gas-tight seal between the tamper-resistant cover 740 and the exposed surface of the stopper to thereby further seal the stopper from the ambient atmosphere and, if desired, further improve the MVT barrier between the interior of the vial and the ambient atmosphere.

Figure 24:
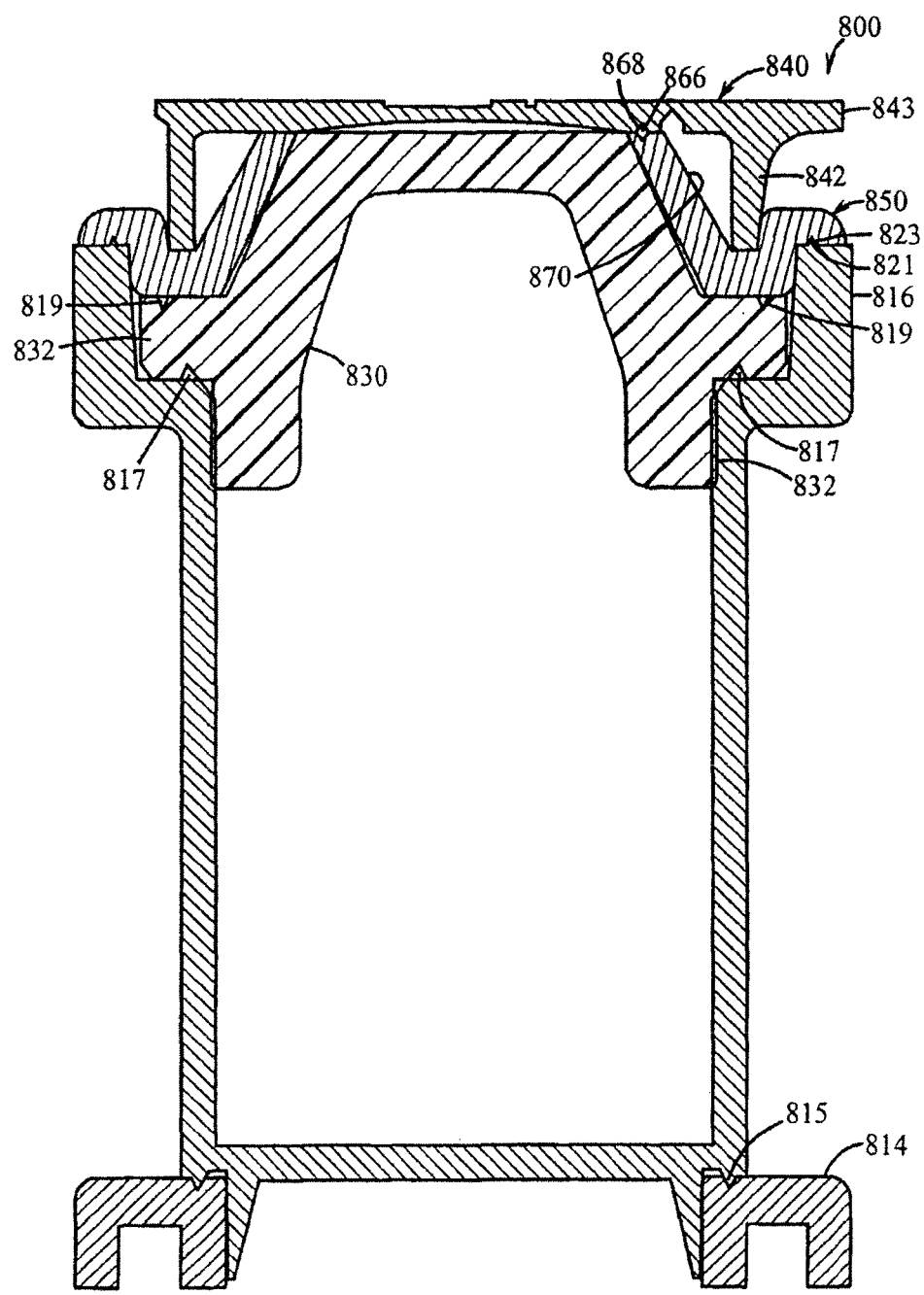
FIG. 24 is a cross-sectional view of the vial of FIG. 23.
Figure 25:
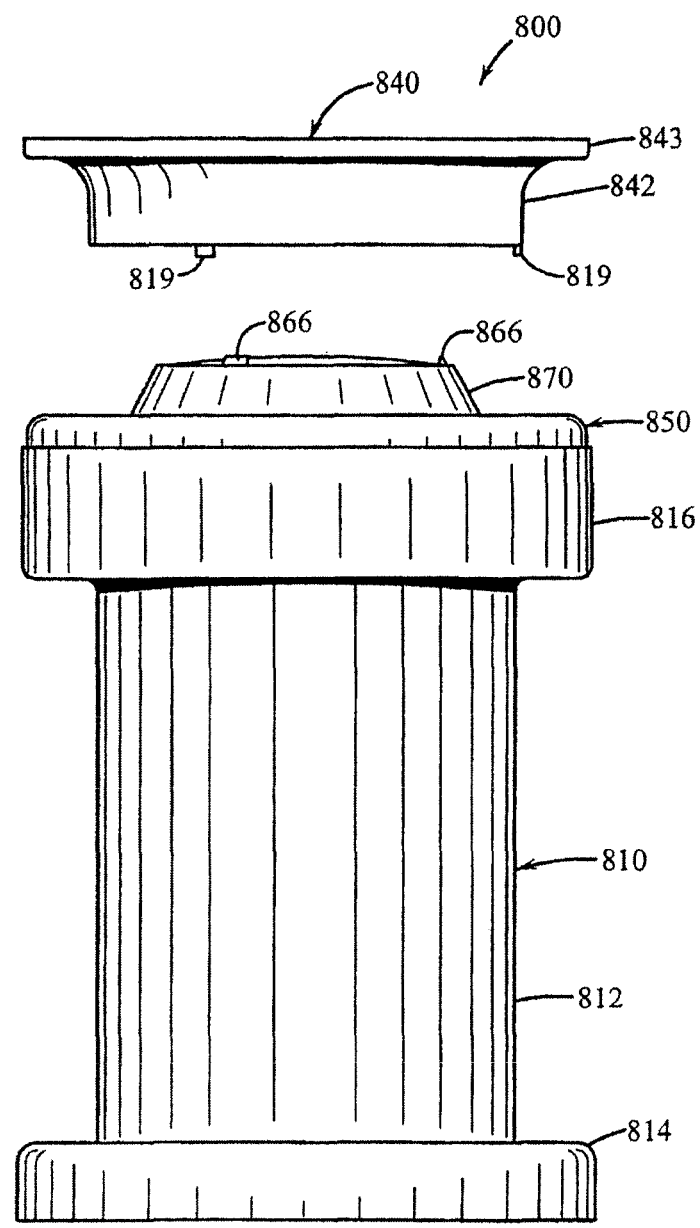
FIG. 25 is a partially exploded, perspective view of the vial of FIG. 23.
Figure 26:
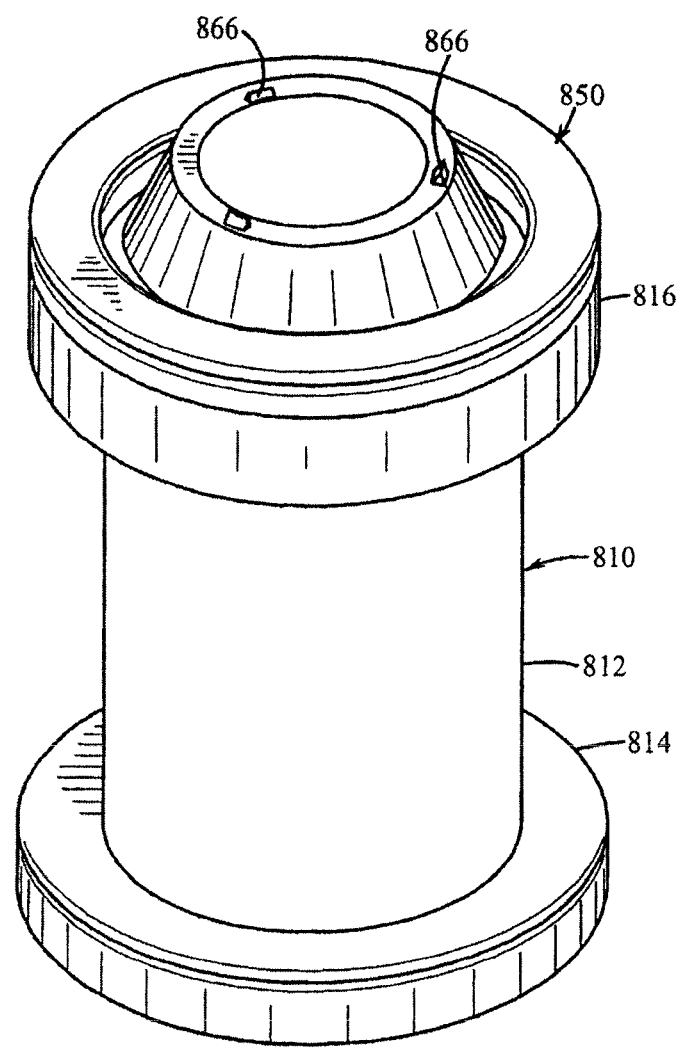
FIG. 26 is a perspective view of the vial assembly of FIG. 23 with the tamper-resistant cover removed.
Figure 27:
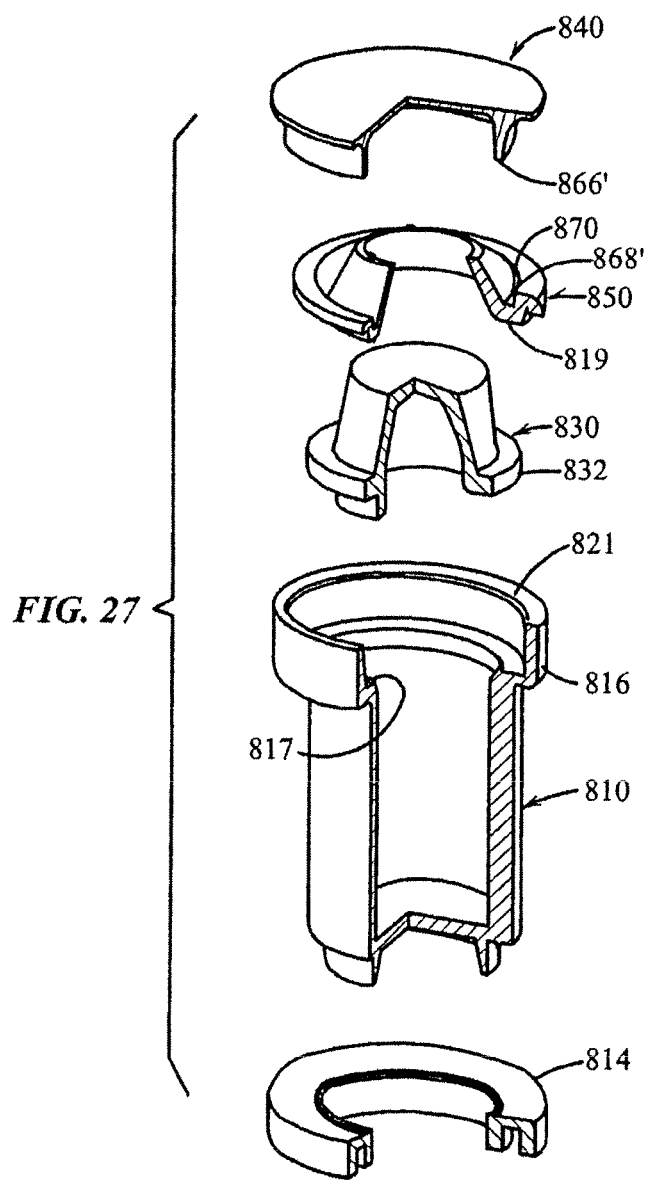
FIG. 27 is an exploded, perspective view of the vial of FIG. 23.
Figure 28:
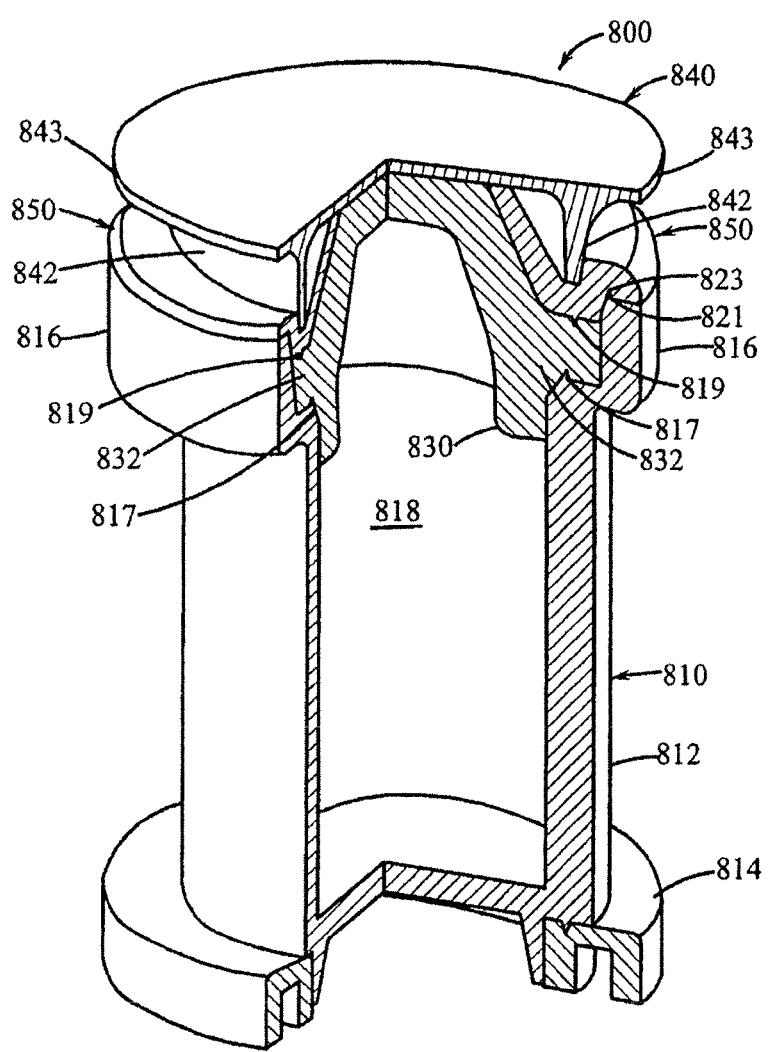
FIG. 28 is partially cut-away, perspective view of the vial of FIG. 23.

In FIGS. 23 through 28, another vial embodying the present invention is indicated generally by the reference numeral 800. The vial 800 is similar in many respects to the vials described above with reference to FIGS. 14 through 23, and therefore like reference numerals preceded by the numeral "8" are used to indicate like elements. The primary difference of the vial 800 in comparison to the vials described above is that the locking ring 850 is welded, such as by ultrasonic welding, to the neck 816 of the vial body. In addition, the flip-top or tamper-resistant cover 840 is tack welded, such as by ultrasonic welding, to the locking ring 850. As shown in FIGS. 24 and 28, the stopper 830 defines an annular flange 832, the neck 816 of the vial body defines a pointed annular protuberance 817 that projects into one side of the stopper flange 832, and the locking ring 850 defines another annular protuberance 819 that projects into the opposite side of the stopper flange 832. Thus, the annular protuberances 817 and 819 define continuous, annular sealing surfaces that facilitate in effectuating a gas-tight or hermetic seal between the stopper and vial body. Further, as shown in FIG. 24, the peripheral surface 832 forms an interference fit with the interior of the valve body 810 to further effectuate a gas-tight or hermetic seal between the stopper and vial body. The neck 816 defines on its axial face a pointed annular protuberance 821 that is received within a corresponding annular recess 823 defined in the underside of the locking ring 850. The annular protuberance 821 is fused to the locking ring 850 within the annular recess 823 by ultrasonic welding, for example, to thereby fixedly secure the locking ring to the vial body. In addition, the annular weld preferably defines a hermetic or gas-tight seal between the locking ring and vial body to further effectuate a gas-tight or hermetic seal between the interior of the vial and the ambient atmosphere. The locking ring 850 further defines on its distal end a plurality of discrete radially-extending protuberances 866 received within corresponding recesses 868 formed within the underside of the locking ring 840. The protuberances 866 are fused to the cover 840 within the recesses 868 by, for example, ultrasonic welding, to thereby define a plurality of frangible connections between the cover 840 and locking ring 850. Alternatively, as shown in FIG. 27, protuberances 866' may be formed at the base of the flange 842 of the cover and may be fused within corresponding recesses 868' formed within the annular recess 870 of the locking ring. As also shown in FIGS. 24, 27 and 28, the base of the vial body defines a pointed annular protuberance 815 that is received within a corresponding annular recess formed in the base 814 for fixedly securing the base to the body, such as, for example, by ultrasonic welding.

In order to fill the vial 810, the stopper 830, locking ring 850, and base 814 are assembled to the empty vial body, such as by ultrasonic welding. Then, the empty vial is sterilized, such as by the application of gamma or other type of radiation thereto. Then, the sterilized, empty vials are needle filled and thermally resealed, such as by laser resealing as described above. Then, the tamper-resistant cover 840 is assembled to the filled vial by fixedly securing the cover to the locking ring 850, such as by ultrasonic welding as described above. As shown typically in FIG. 24, the exterior surface of the stopper 830 may form an interference fit with the interior surface of the tamper-resistant cover to further effectuate a gas-tight or hermetic seal between the cover and stopper to, in turn, form a further MVT barrier between the interior of the vial and the ambient atmosphere through the cover. If desired, a peripheral seal may be formed between frusto-conical portion 870 of the locking ring and the underside of the tamper-resistant cover 840 by forming an annular seal at 866, 868 by, for example, ultrasonic welding, to form the hermetic or gas-tight seal between the stopper and the ambient atmosphere and, in turn, form the desired MVT barrier. In order to use the vial, the tamper-resistant cover 840 is removed by gripping with, for example, a thumb, the peripheral edge 843 of the cover, and pushing the cover upwardly or substantially axially away from the locking ring to, in turn, break the frangible connections 866, 868 or 866', 868' and release the cover, or a frangible portion thereof, from the locking ring to expose the underlying stopper. As may be recognized by those of ordinary skill in the pertinent art based on the teachings herein, the tamper-resistant cover and/or the frangible portion thereof may taken any of numerous different shapes and/or configurations that are currently or later become known for performing the function of the tamper-resistant cover as described herein.

Figure 29:
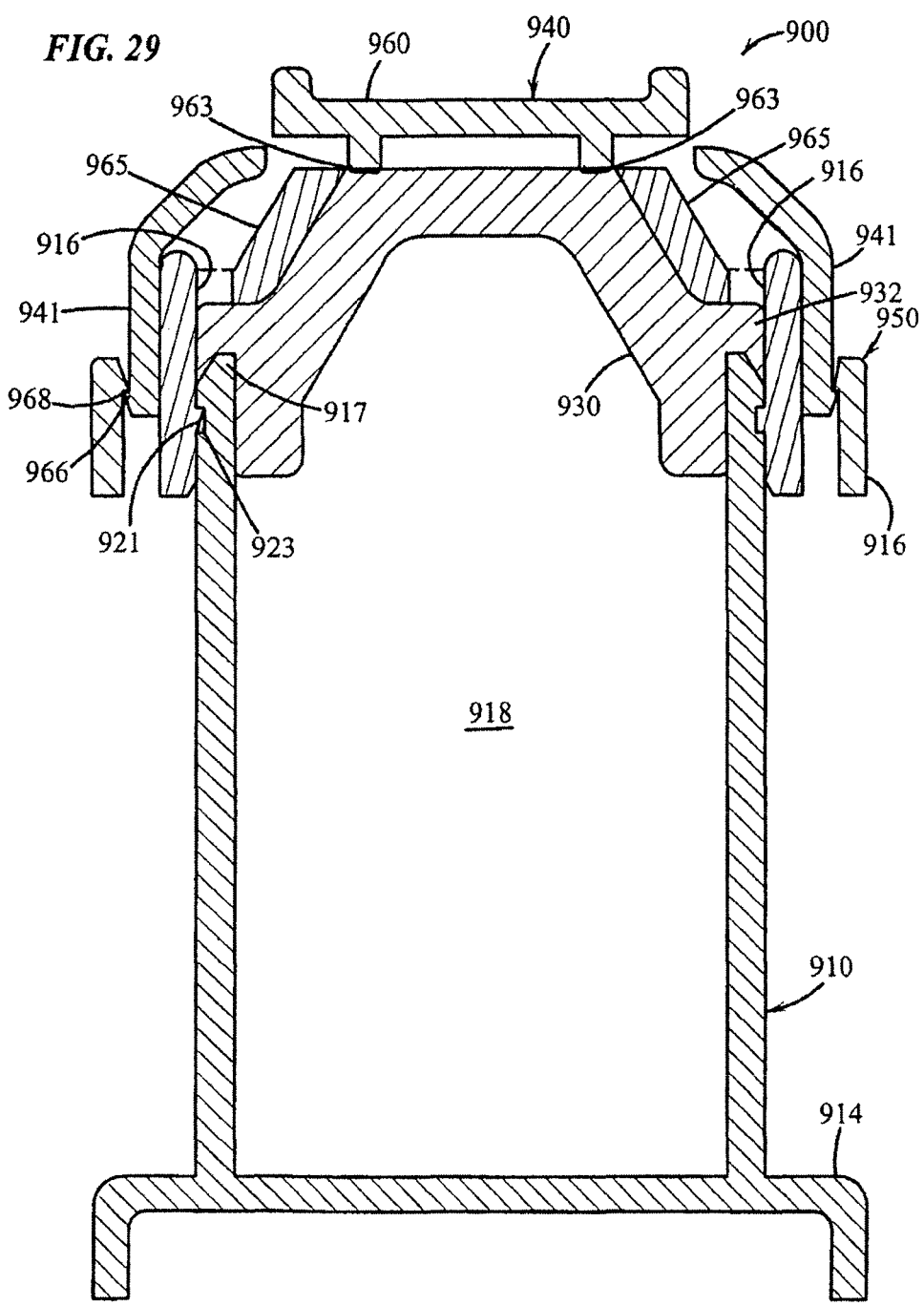
FIG. 29 is a cross-sectional view of another vial embodying the present disclosure.
Figure 30:
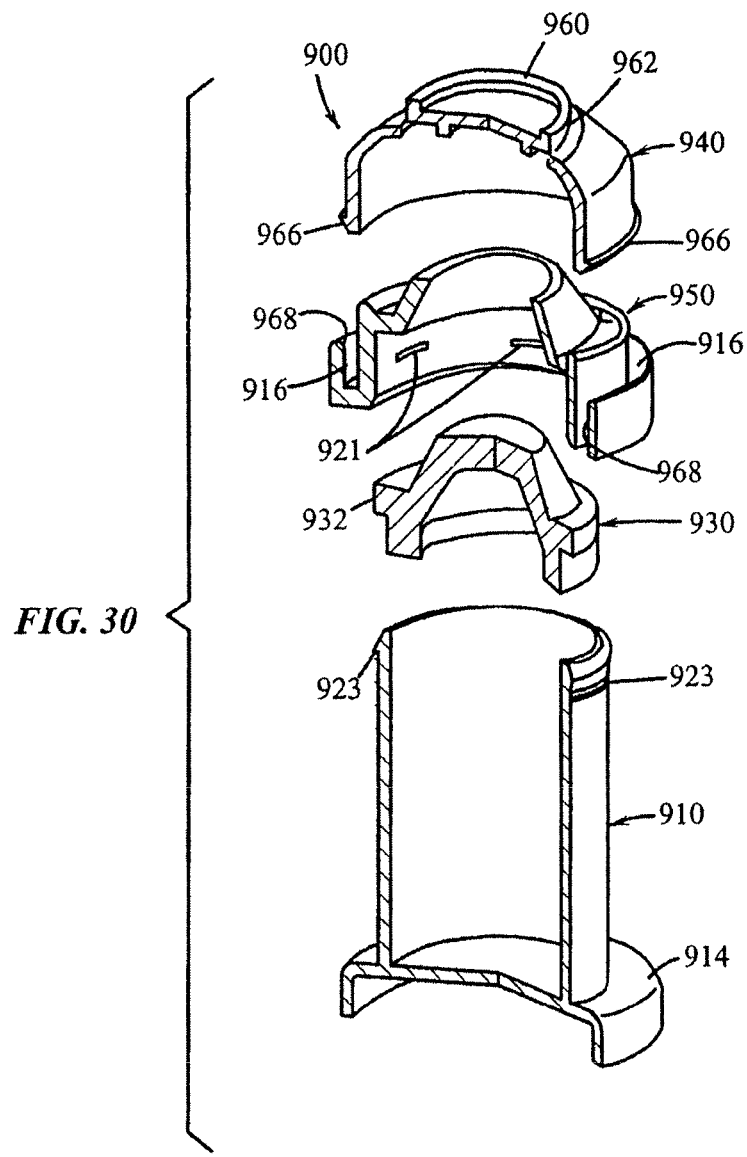
FIG. 30 is a perspective, exploded view of the vial of FIG. 30.
Figure 31:
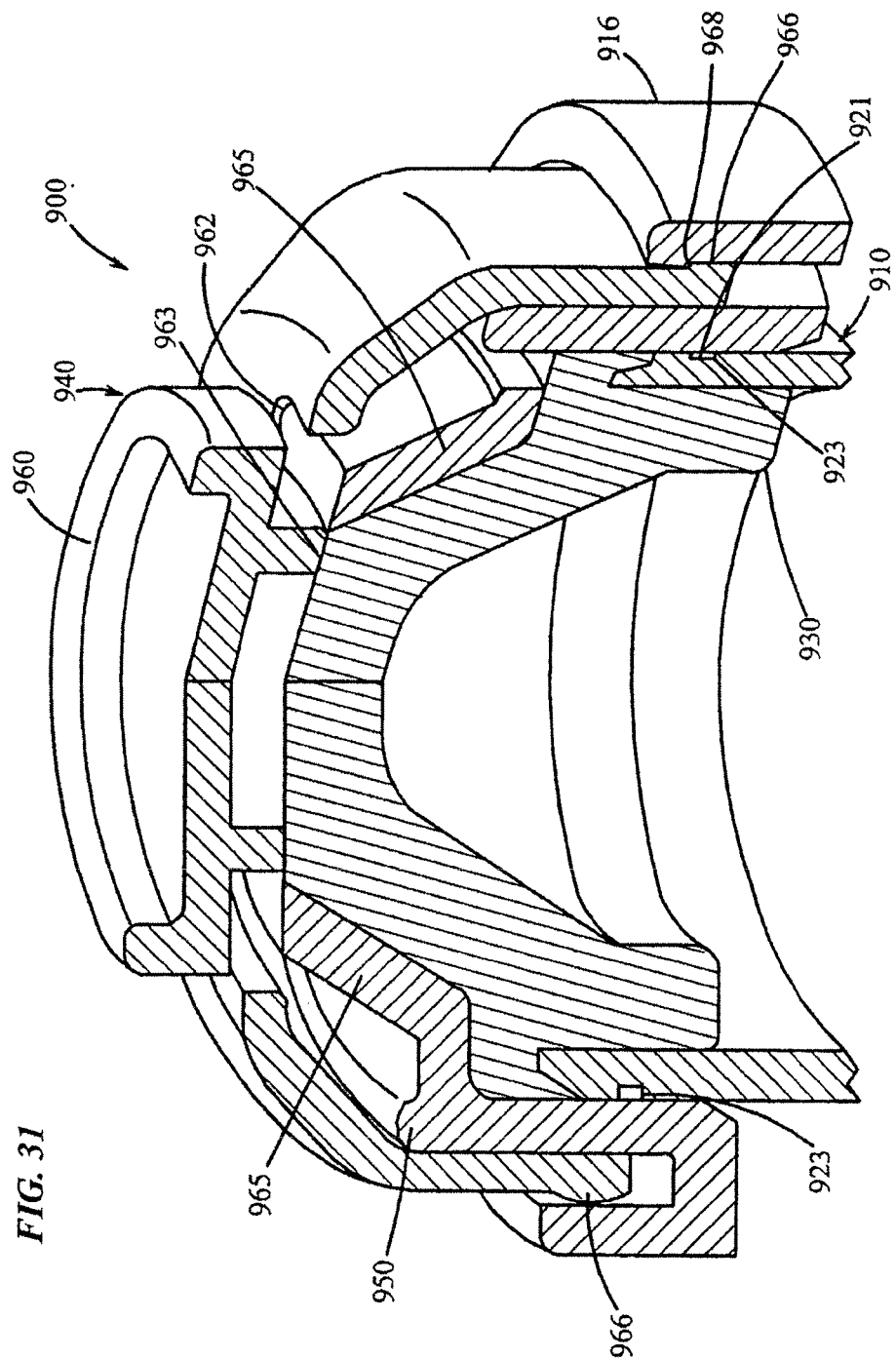
FIG. 31 is a perspective, partial, cut-away view of the vial of FIG. 30.

In FIGS. 29 through 31, another vial embodying the present invention is indicated generally by the reference numeral 900. The vial 900 is similar in many respects to the vials described above with reference to FIGS. 14 through 28, and therefore like reference numerals preceded by the numeral "9" are used to indicate like elements. The primary difference of the vial 900 in comparison to the vials described above is that the locking ring 950 is snap-fit to the vial body 910, and the locking ring 950 defines the neck 916 of the vial. As can be seen, the locking ring 950 defines a peripheral flange forming the neck 916 and further defines on its interior edge an annular recess 968 for receiving therein an annular protuberance 966 formed on the tamper-resistant cover 940. As can be seen, the interior edge of the annular flange 916 leading into the recess 968 defines a chamfered surface, and the leading edge of the annular protuberance 966 of the cover also is chamfered to allow the protuberance to be snapped into, or otherwise fixedly received within the recess, but to prevent removal of the cover therefrom. Similarly, the locking ring 950 defines on its inner diameter an annular protuberance 921 that is snapped into, or otherwise fixedly received within a corresponding annular recess 923 formed on the exterior of the vial body to fixedly secure the cover to the vial body. In this embodiment, the base 914 of the vial body is formed integral with the remainder of the vial body in order to reduce the number of parts; however, if desired, the base 914 can be made as a separate part that is snap-fit or otherwise attached to the vial body.

As shown typically in FIG. 31, the tamper-resistant cover 940 defines a centrally-located frangible portion 960, an inwardly depending annular protuberance 963 that engages the exposed surface of the stopper 930 and forms a hermetic or gas-tight seal therebetween, and a frusto-conical portion 965 that is formed on its outer end contiguous to the annular protuberance 963 and preferably forms a gas-tight or hermetic seal therebetween. As shown in FIGS. 30 and 31, a plurality of frangible connections 962 are angularly spaced relative to each other and extend between the frangible portion 960 and a substantially dome-shaped cover body 941 to allow removal of the frangible portion and access to the underlying stopper 930. As indicated by the arrow in FIG. 32, the frangible portion 960 of the cover is pressed downwardly by, for example, a user's finger to slightly depress the underlying stopper material and, in turn, break the frangible connections 962. Once removed, the frangible portion 960 cannot be reconnected to thereby provide a tamper-proof feature. Thus, prior to removing the frangible portion 960 of the tamper-resistant cover 940, the frangible portion 960, along with its annular protuberance 963, and the frusto-conical portion 965 of the locking ring 950, form a substantially gas-tight or hermetic seal between the stopper and ambient atmosphere, and thus provide a further MVT barrier between the interior of the vial and ambient atmosphere in the direction through the stopper. If desired, or otherwise deemed necessary to further obtain a desired MVT barrier, the frusto-conical portion 965 and peripheral flange 916 may form a continuous solid barrier, as indicated in broken lines in FIG. 29 (i.e., without any openings), to completely seal the stopper from the ambient atmosphere.

Turning to FIGS. 32 through 36, a plurality of the diabolo shaped vials 610 of the present invention are shown mounted within a sterile filling machine that needle fills and laser reseals the vials as disclosed in co-pending U.S. Provisional Patent Application Ser. No. 60/484,204, filed Jun. 30, 2004, and incorporated by reference above. As can be seen, each vial 610 does not include the tamper-resistant cover 640 (FIG. 18) during the needle filling and laser resealing process, but rather the tamper-resistant covers are secured to the vials after needle filling and laser resealing. As may be recognized by those of ordinary skill in the pertinent art based on the teachings herein, although the vials 610 are shown mounted within the sterile filling machine, any of the other vials described herein or otherwise embodying the features of the invention equally may be filled and sealed in the illustrated sterile filling machine. The sterile filling machine includes a sterile enclosure (not shown), a laminar flow source (not shown) that provides a substantially laminar flow of sterile air of other gas over the vials being transported within the enclosure, and as shown in FIGS. 33-36, a transport system comprising in the illustrated embodiment a plurality of star wheels 1010, and associated guides 1012 spaced adjacent to the periphery of each star wheel 1010 for supporting the vials 610 therebetween.

As shown in FIGS. 33-36, each of the star wheels 1010 has a plurality of recesses 1014 along its peripheral surface that are adapted to receive the mid-portions of the vials 610. One or more of the star wheels may have a saw-tooth like periphery that reduces the likelihood of jamming against vials as they are received, for example, from a turntable and infeed channel into the star wheels. In such embodiment, the periphery of the star wheel defines a plurality of teeth, wherein each tooth has a pointed end, and each two successive teeth form a respective one of the recesses adapted to receive a vial. In this embodiment, the teeth and/or recesses are shaped and/or dimensioned such that the portion of the tooth that is substantially upstream and adjacent to the point defines a seat in which a respective vial rests. Also in this embodiment, the seat defines a surface that pushes against the container. Other designs may of course also be employed. If desired, the recesses 1014 of one or more star wheels may be provided with vacuum ports which are selectively connected to a vacuum source (not shown) to thereby allow the star wheels to carry and release vials as appropriate.

As shown best in FIGS. 32-35, a needle fill manifold 1016 is disposed at a first position along the periphery of the star wheel 1010 in a needle filling station of the sterile filling machine. The needle fill manifold 1016 holds a plurality of needles, e.g., four needles 1018, 1020, 1022 and 1024, which are used to deliver medicament or other substances into the sealed vials. The needle manifold 1016 is drivingly mounted such that each needle is movable into and out of engagement with the resealable stoppers to pierce the stoppers and fill the vials with a medicament or other substance to be contained therein, and to then withdraw the needle upon filling the vial. Providing multiple needles makes it possible to fill multiple vials concurrently. Each of the needles is in flow communication with a respective flexible tube 1026, 1028, 1030 and 1032 that connects the respective needle 1018, 1020, 1022 and 1024 to a respective medicament or other substance source (not shown) through a respective one of a plurality of pumps (not shown). The medicament source may be located inside the filling machine or outside of the filling machine.

Figure 32:
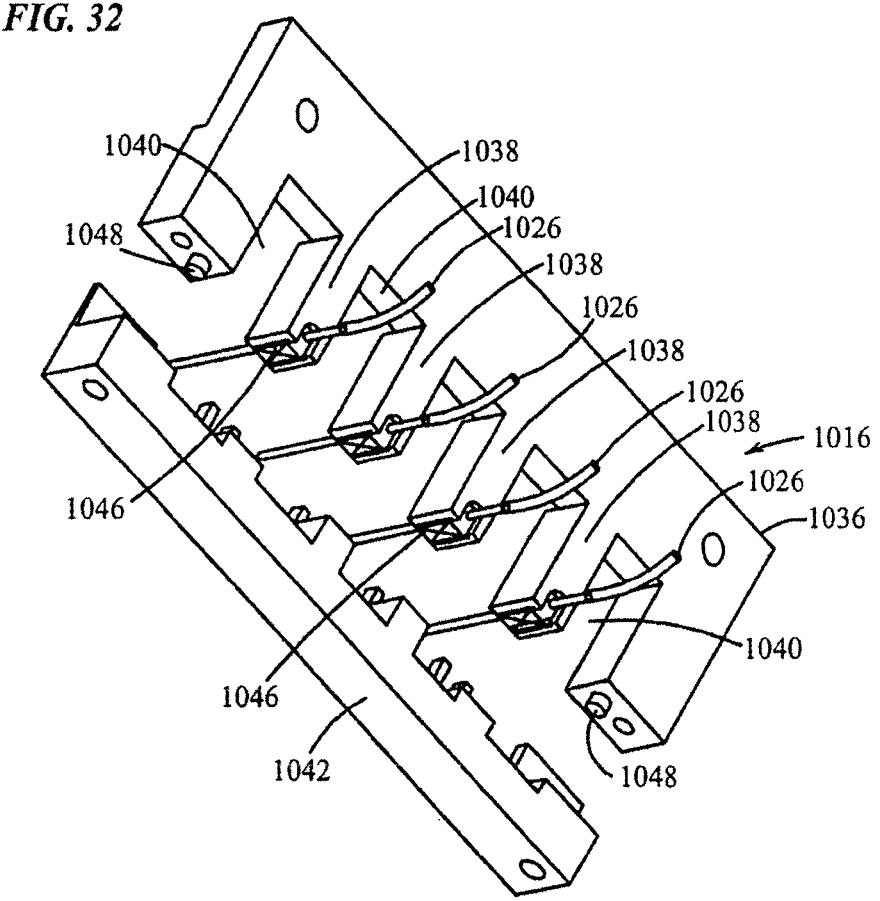
FIG. 32 is a perspective, partly exploded view of a needle manifold used in a needle filling module of a sterile filling machine for needle filling the vials with a medicament or other substance to be contained therein.
Figure 33:
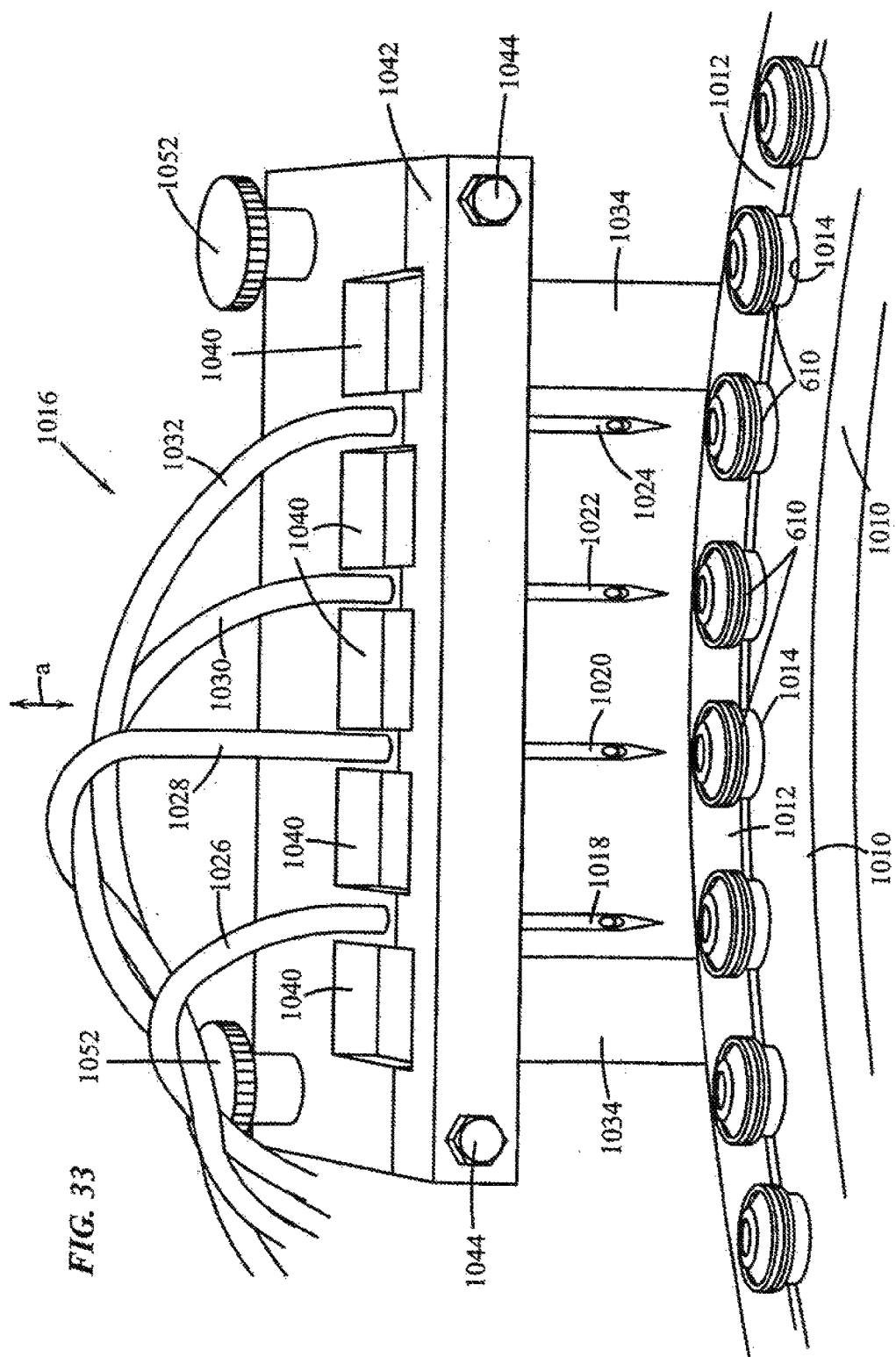
FIG. 33 is a front perspective view of the needle manifold of FIG. 32 located in an "up" position within a sterile enclosure of a sterile filling machine, and with a plurality of vials mounted within a transport system including a star wheel and associated guide, that are aligned with the needles and ready for needle filling.
Figure 34:
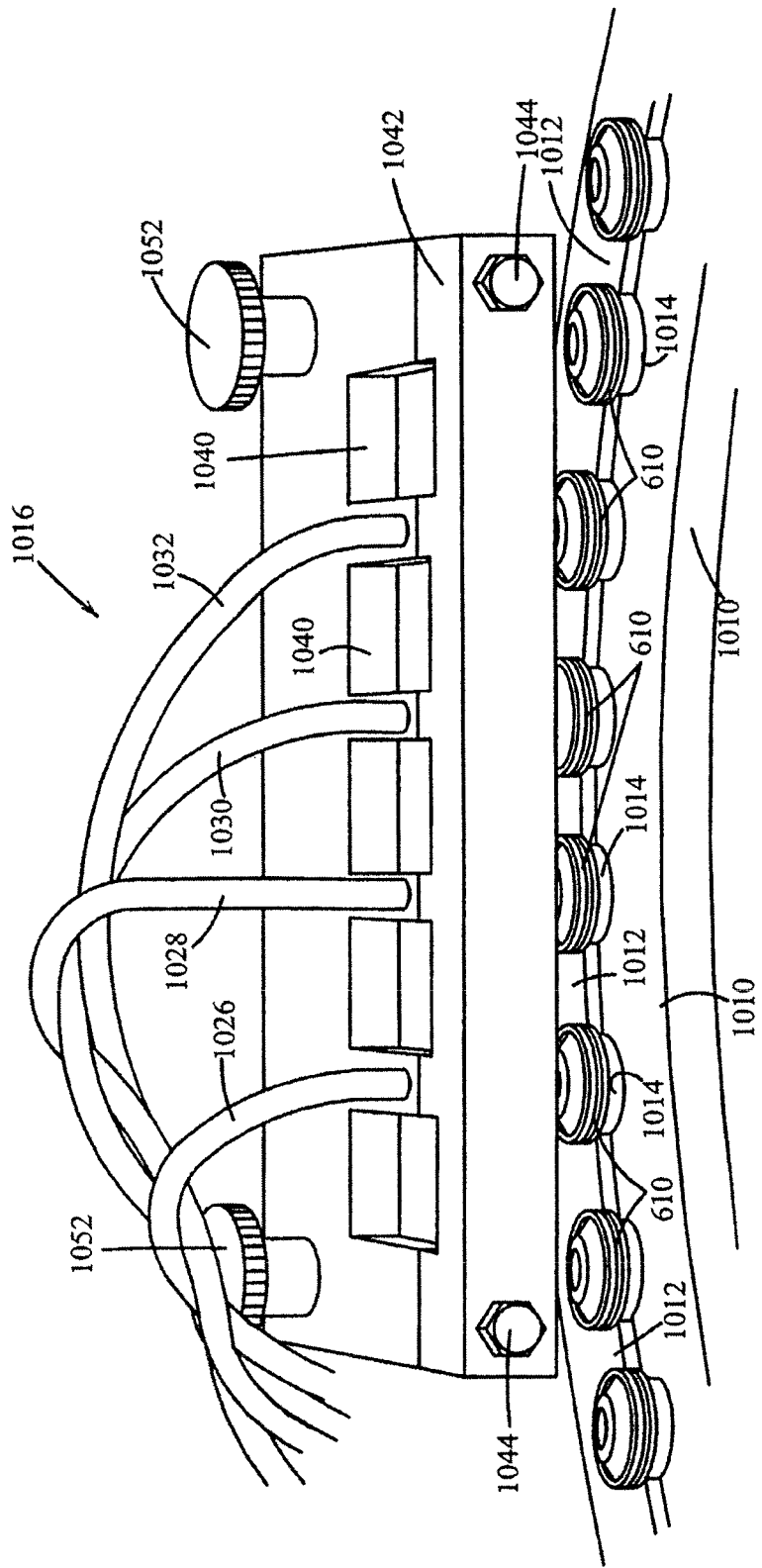
FIG. 34 is a front perspective view of the needle manifold and transport system of FIG. 33 showing the needle manifold in a "down" position with the needles penetrating the resealable stoppers of the vials and filling the interiors of the vials with a medicament or other substance to be contained therein.
Figure 35:
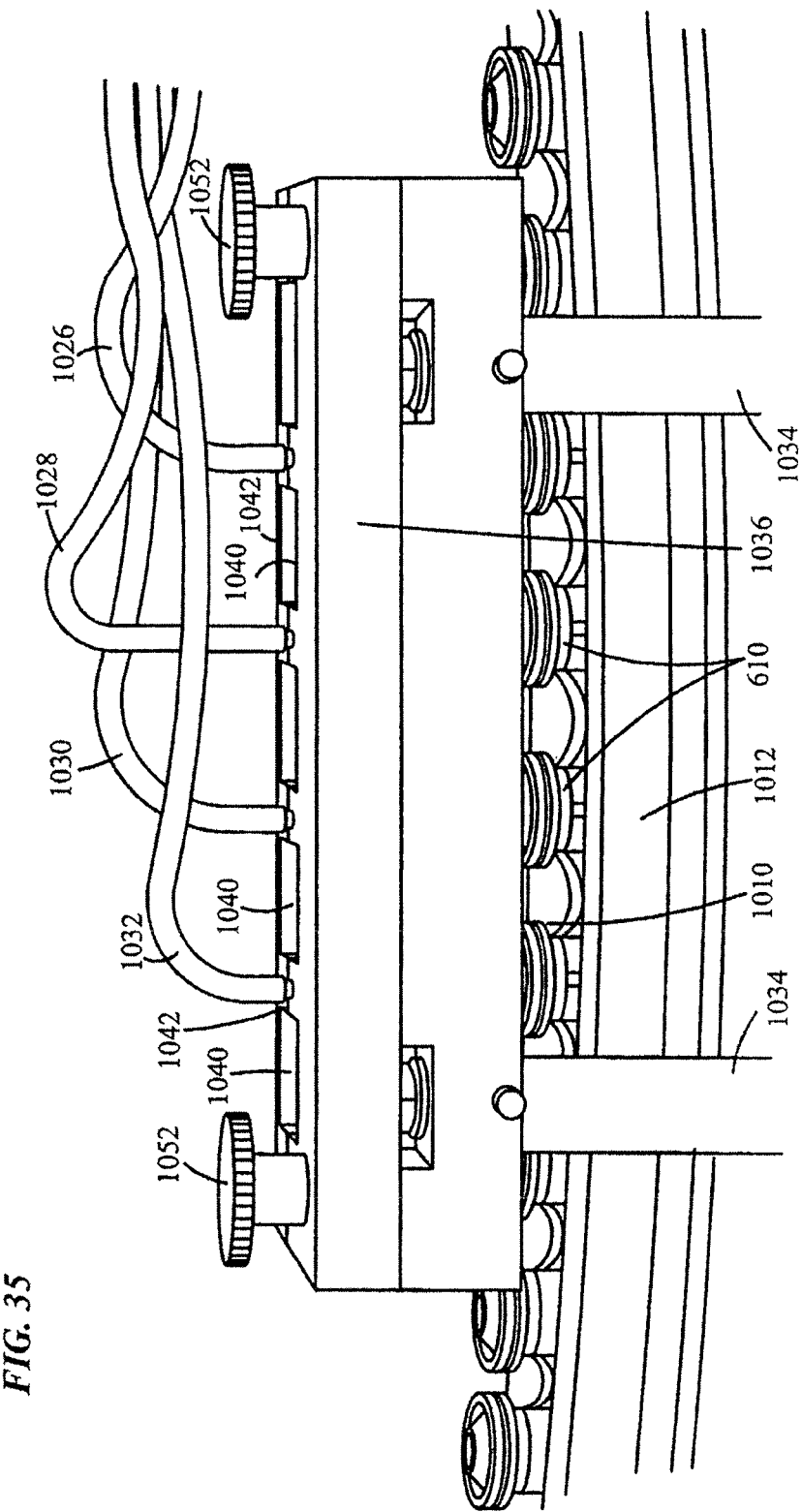
FIG. 35 is a rear perspective view of the needle manifold and transport system of FIG. 33 showing the needle in the "down" or fill position.

As shown in FIGS. 33-35, the needle fill manifold 1016 is mounted on a pair drive shafts 1034 that are drivingly connected to a suitable drive source (not shown) driving the needle manifold, and thus the bank of needles mounted on the manifold, into and out of engagement with the resealable stoppers of the vials mounted in the needle filling station, as indicated by the arrow "a" shown typically in FIG. 33. Although not shown, a bellows may encase the base of each shaft to seal the movable parts of the shafts. As shown best in FIG. 32, the needle manifold 1016 further includes a base 1036, a plurality of needle mounts 1038 spaced relative to each other and defining laminar flow apertures 1040 therebetween, and a clamp 1042 that is fixedly secured by fasteners 1044 (FIG. 33) to the base 1036 to, in turn, secure the needles to the manifold. As shown in FIG. 32, each needle includes a mounting flange 1046 that is slidably received within an aperture formed in the respective needle mount 1038, and is fixed in place upon securing the clamp 1042 to the base 1036. Alignment pins 1048 project outwardly from the front face of the base 1036 and are received within corresponding apertures formed in the clamp 1042 to ensure proper alignment of the clamp and needles on the manifold. As shown in FIG. 35, the a mounting plate 1050 is fixedly secured to the ends of the drive shafts 1034, 1034 and is movable therewith. Alignment pins (not shown) extend between the base 1036 of the needle manifold 1016 and the drive plate 1050 to ensure proper alignment of the needle manifold, and thus the needles, on the drive plate. A pair of thumb screws 1052 are threadedly received through opposite ends of the base 1036 of the manifold to releasably secure the manifold to the drive plate 1050.

As shown in FIG. 36, a laser sealing and infrared (IR) sense manifold 1054 is disposed at a second position along the periphery of the star wheel 1010, downstream of the needle fill manifold 1016. As shown typically in FIG. 36, the laser sealing and infrared (IR) sense manifold 1054 holds a plurality of laser optics assemblies (e.g., four laser optic assemblies 1056, 1058, 1060 and 1062), along with a plurality of IR sensors (e.g., four IR sensors 1064, 1066, 1068 and 1070). The laser optic assemblies are adapted to provide a laser beam to reseal the resealable stoppers on the vials after needle filling. Each of the plurality of laser optic assemblies is mounted at a respective location near the periphery of the star wheel 1010 for transmitting a respective laser beam onto a respective resealable stopper to heat seal the needle aperture in the resealable stopper. Each of the laser optic assemblies 1056, 1058, 1060 and 1062 is connected to a respective fiber optic cable that connects the respective optic assembly to a respective laser source (not shown). Providing multiple fiber optic assemblies makes it possible to reseal multiple vials concurrently. In this embodiment, each of the plurality of IR sensor assemblies 1064-1070 is mounted at a respective location near the periphery of the star wheel 1010. Preferably, the laser sources (not shown) are mounted outside of the enclosure to enable repair and/or replacement of the laser sources without having to open the enclosure and/or otherwise risk contamination of the sterile enclosure. The IR sensors 1064-1070 detect the temperature of the needle penetration region of the resealable stopper achieved during laser resealing, and therefore can be used to determine whether the stopper was sufficiently reheated to achieve resealing. Each of the IR sensors 1064-1070 is connected to a respective IR sensor module (not shown). Providing multiple IR sensors enables the sterile filling machine to sense the temperature of multiple vials concurrently, for example, as they are being resealed.

As described above, each laser source transmits a predetermined wavelength of laser radiation at about 980 nm, and the predetermined power of each laser is preferably less than about 30 Watts, and preferably less than or equal to about 10 Watts, or within the range of about 8 to about 10 Watts. In the illustrated embodiment, each laser source is a semiconductor diode laser that outputs at about 15 Watts, and is fiber-optically coupled through a fiber-optic cable to respective collimating lens mounted over the vials within the interior of the filling unit. The laser and IR sensor manifold 1054 includes a tinted enclosure 1072 including a plurality of tinted glass or translucent or transparent plastic panels that surround the lasers on four sides to filter out potentially harmful radiation generated by the laser beams. Capacitor sensors (not shown) also may be provided along the periphery of the star wheel 1010, downstream of the needle fill manifold 1016 in order to sense whether each vial received the medicament or other substance to be contained therein and to reject the vial if defective.

In the operation of the sterile filling machine, the star wheel 1010 transports the vials 610 along the guide 1012 in the manner illustrated. The star wheel 1012 is indexed four positions and then paused for a momentary dwell. During the dwell, the needle manifold 1016 is driven downward so as to drive the four needles 1018-1024 through the resealable stoppers on the four vials beneath the needle manifold. Medicament or other substance is thereafter delivered by the pump through the needles and into the interior chambers of the vials, and the manifold is then driven up to thereby retract the four needles 1018-1024 from the four stoppers. In one embodiment, the needles are initially withdrawn at a relatively slow speed to allow the vials to fill "bottom-up"; then, when the vials are filled, the needles are withdrawn at a relatively faster speed to quickly remove the needles and decreases overall cycle time. As shown in FIGS. 33-35, the diabolo or spool-like shape of the vials facilitates the ability to transport the vials on the star wheels or other conveying system, and further, the diabolo shape support the vials and prevents axial movement of the vials during insertion and withdrawal of the needles during filling. The mid-portion of each vial is secured within the recess of the star wheel or other conveying mechanism, the relatively larger diameter upper portion of each vial prevents axial downward movement of the vial upon inserting the needle into the resealable stopper of the vial by engaging the upper surface of the star wheel and/or guide, and the relatively larger diameter base portion of the vial prevents upward axial movement of the vial upon withdrawal of the needle from the resealable stopper by engaging the underside of the star wheel and/or guide.

Also during the dwell, the four laser optic assemblies 1056-1062 deliver laser energy to the resealable stoppers on the four vials beneath the laser and IR manifold to reseal the stoppers. As the resealable stoppers are heated by the laser energy, the four IR sensors 1064-1070 detect the temperature of each stopper, so as to be able to determine whether each stopper was heated sufficient to cause resealing. After the dwell, the process is repeated, i.e., the star wheels index another four positions and then dwell again so that the next four vials are filled and four more vials are resealed.

After resealing, the vials are transferred to the another star wheel (not shown), which employs the vacuum ports in its recesses to retain each vial as it is transported. If a vial was successfully filled and sealed, then the star wheel transports that vial until reaching a discharge guide, at which point the vacuum to the associated vacuum port is selectively removed and the vial is transferred to the discharge guide. The discharge guide transports the vial to a bin (not shown) of successfully filled and sealed containers. If a vial was not successfully filled and sealed, then the star wheel transports that vial until it reaches another star wheel, at which point the vacuum to the associated vacuum port is selectively removed and vacuum is applied to the respective vacuum port on the other star wheel, thereby transferring the vial to the other star wheel for disposal with any other defective vials.

In FIGS. 37-48, a module for needle filling and laser resealing the vials is indicated generally by the reference numeral 2000. The needle filling and laser resealing module 2000 is similar in many respects to the needle manifold and laser and IR sensor manifold described above, and therefore like reference numerals preceded by the numeral "2" instead of the numeral "1" are used to indicate like elements. One of the primary differences of the module 2000 in comparison to the manifolds described above, is that the module 2000 permits both needle filling and laser resealing in the same module. Further, if desired, the module 2000 can include an e-beam or other suitable radiation or sterilization source to further ensure sterilization of the vials and filling needles, as described further below.

The module 2000 may be mounted within any of numerous different types of sterile enclosures, and may be used with any of numerous different types of conveying systems for conveying the vials through the module. If desired, the sterile enclosure may include a laminar flow source as described in the above-mentioned co-pending patent application. Preferably, the transport system through the module is substantially linear, and includes a guide 2010 defining an axially elongated aperture 2014 extending therethrough. As shown in FIGS. 39 and 40, the axially extending aperture 2014 is dimensioned to slidable receive therein the mid-portions of the diabolo-shaped vials, to support on the upper opposing surfaces of the guide 2010 the relatively larger diameter upper portion of each vial, and if desired, to support against the opposing lower surfaces of the guide the relatively larger diameter base portion of each vial. In one embodiment of the present invention illustrated in FIG. 43, the transport system comprises a screw-type drive including a lead screw 2015 defining a helical groove 2017 forming the recesses for receiving the vials 610. A motor 2019 is drivingly connected to one end of the lead screw and rotatably drives the screw as indicated by the arrow "b" to, in turn, axially drive the vials 610 through the manifold 2000. The motor 2019 is electrically connected to a control unit (not shown) to precisely control the starting, stopping and speed of the screw, and to coordinate same with the actuation of the needle manifold and laser sources. As may be recognized by those of ordinary skill in the pertinent art based on the teachings herein, the transport system may include any of numerous different structures for driving the vials through the manifold, including, for example, other types of conveyors, that are currently, or later become known, for performing this function.

The needle fill manifold 2016 is mounted on a pair drive shafts 2034 that are drivingly connected through a common drive shaft 2035 (FIG. 42) to a suitable drive source (not shown) for driving the needle manifold, and thus the bank of needles 2018 (only one shown) mounted on the manifold, into and out of engagement with the resealable stoppers of the vials received within the guide 2010 of the manifold. Although not shown, a bellows may encase the base of each shaft to seal the movable parts of the shafts. The needle manifold 2016 includes a base 2036, a plurality of needle mounts 2038 spaced relative to each other, and a clamp 2042 that is fixedly secured by fasteners (not shown) to the base 2036 to, in turn, secure the needles to the manifold. If desired, laminar flow apertures may be formed between the needle mounts 2038 to allow the flow of sterile air or other gas therethrough and over the sides of the needles. Each needle includes a mounting flange 2046 that is slidably received within an aperture formed in the respective needle mount 2038, and is fixed in place upon securing the clamp 2042 to the base 2036. Providing multiple needles makes it possible to fill multiple vials concurrently. Each of the needles is in flow communication with a respective flexible tube 2026 that connects the respective needle 2018 to a respective medicament or other substance source (not shown) through a respective one of a plurality of pumps (not shown). The medicament source may be located inside the filling machine or outside of the filling machine.

Figure 40A:
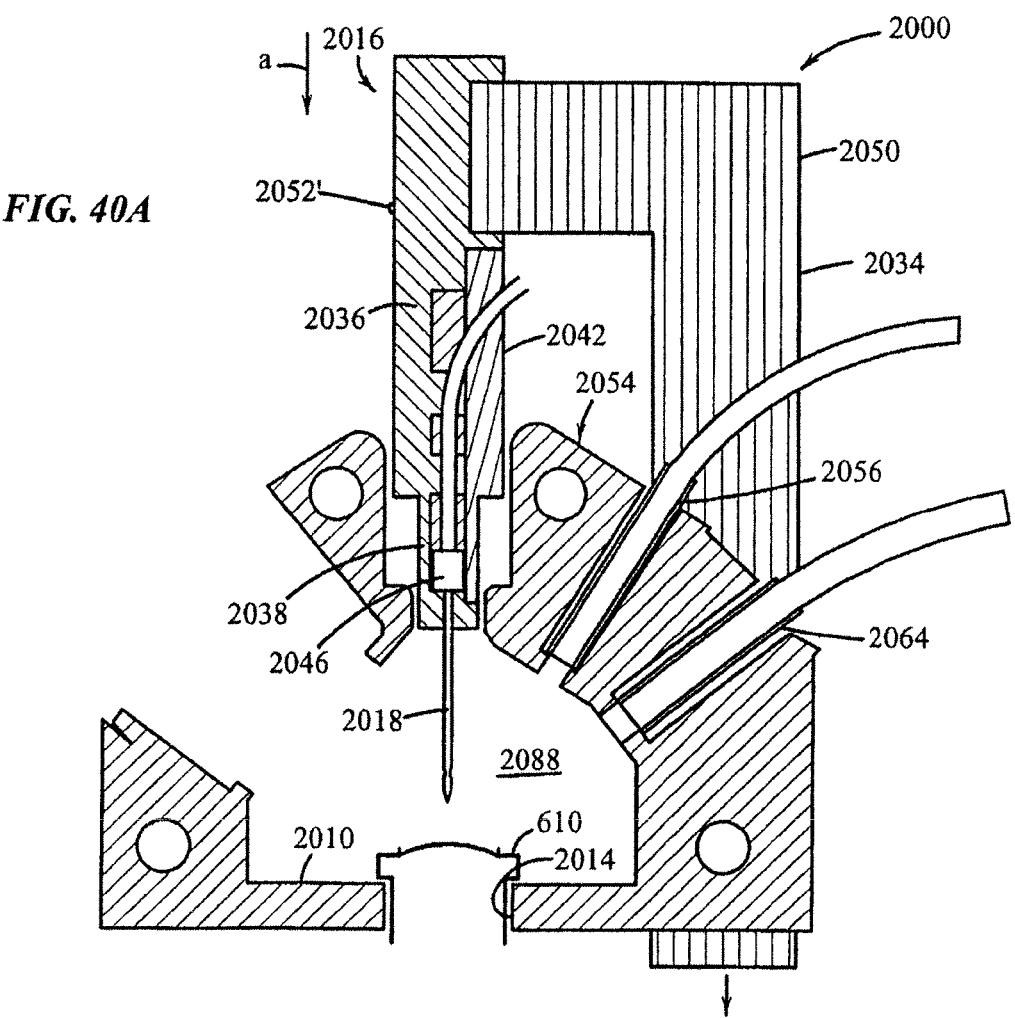
FIG. 40A is an end elevation view of the module with parts removed for clarity, and showing an exemplary laser optic assembly and sensor.
Figure 40C:
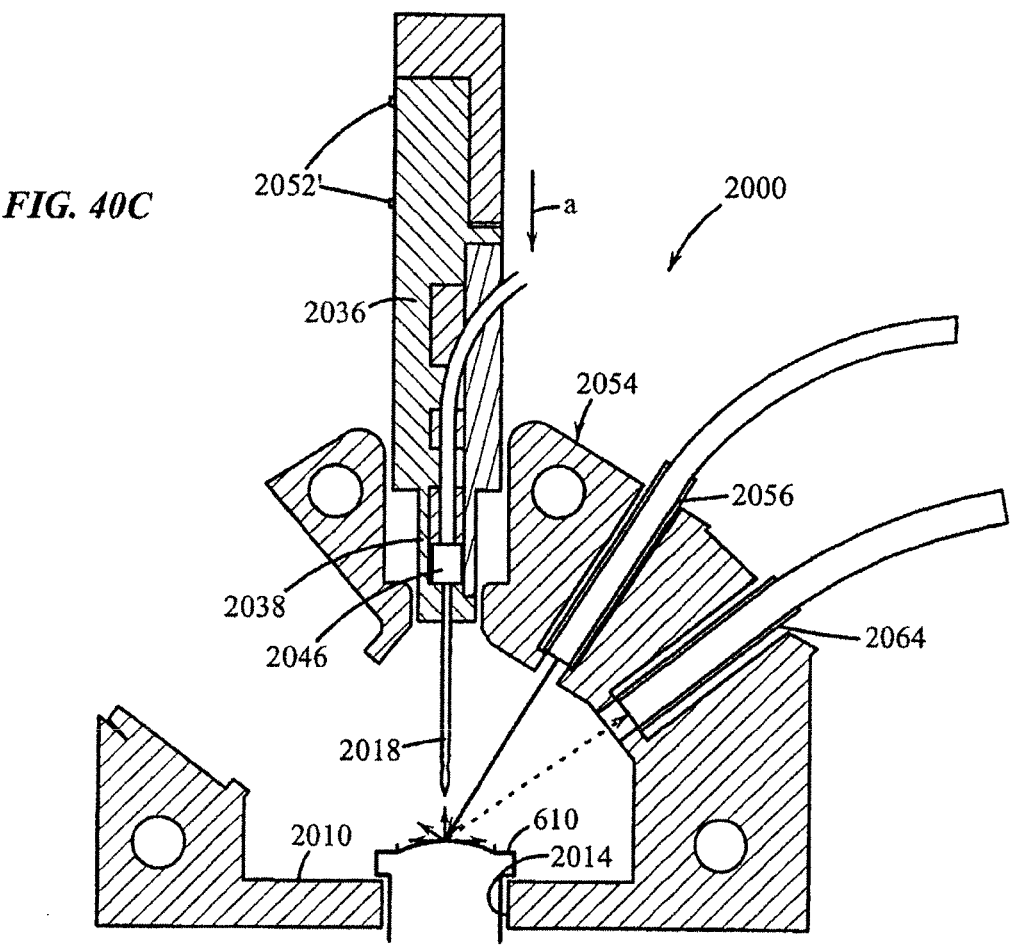
FIG. 40C is an end elevation view of the module of FIG. 40A showing the needle removed from the resealable stopper, the laser beam being transmitted onto the penetration point of the needle, and the IR sensor sensing the temperature of the resealed portion of the stopper to ensure the integrity of the seal.
Figure 41:
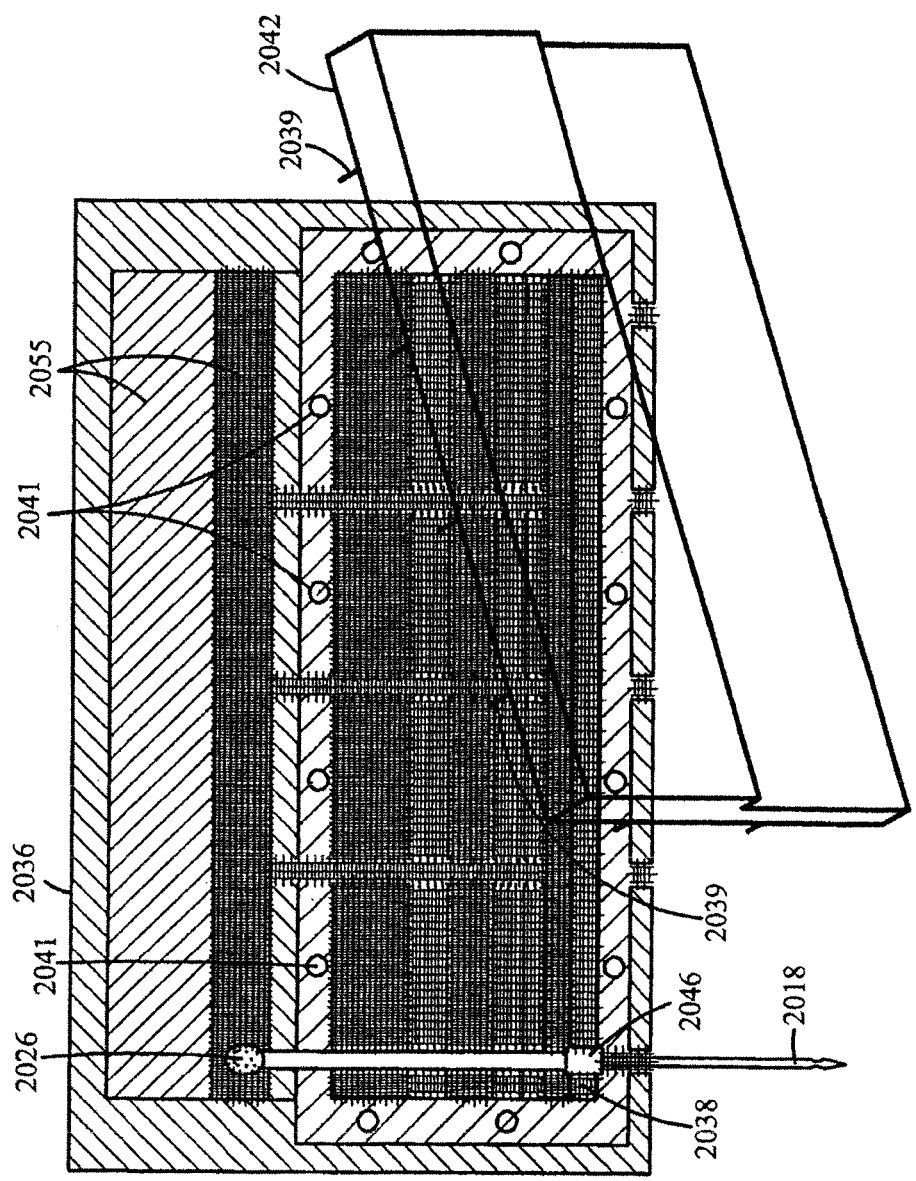
FIG. 41 is a partly exploded view of the needle manifold of the module with some parts removed for clarity.

As shown typically in FIG. 41, alignment pins 2039 may be provided on the clamp 2042 and received within corresponding pin holes 2041 formed on the base 2036 to ensure proper alignment of the clamp and needles on the manifold. A mounting plate 2050 is fixedly secured to the ends of the drive shafts 2034, 2034 and is movable therewith. The drive plate 2050 defines a mounting surface 2053 that is received within corresponding mounting grooves 2055 formed within the base 2036 of the manifold to mount and align the manifold on the drive plate. Alignment pins (not shown) may extend between the base 2036 of the needle manifold 2016 and the drive plate 2050 to ensure proper alignment of the needle manifold, and thus the needles, on the drive plate. A locking clamp 2052 is pivotally mounted on the drive plate 2050 and is movable between an open position to either release the manifold from, or attach the manifold to the drive plate, as shown in FIG. 37, and a closed position fixedly securing the manifold to the drive plate, as shown in FIG. 38. Alternatively, as shown in FIGS. 40A-40C, fasteners 2052' may be employed to secure the manifold to the drive plate, instead of the clamp. As may be recognized by those or ordinary skill in the pertinent art based on the teachings herein, any of numerous different clamps or fastening mechanisms that are currently known, or later become known, equally may be employed to secure the manifold to the drive plate.

Figure 42:
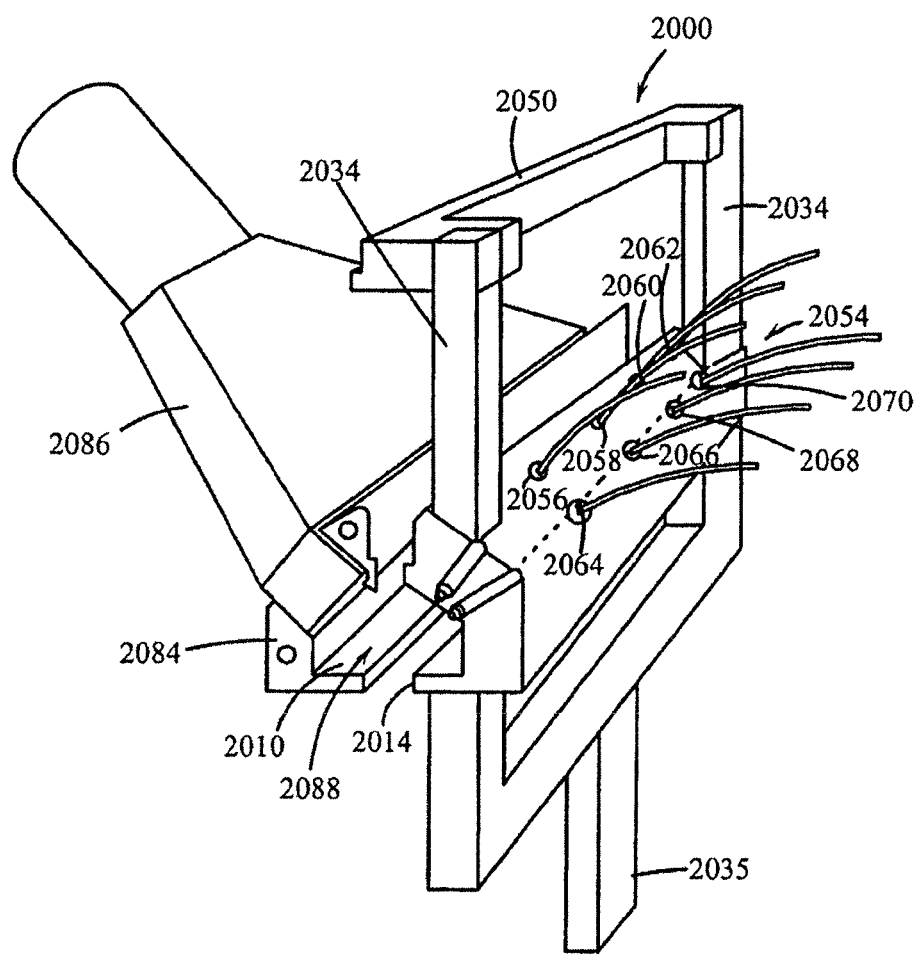
FIG. 42 is a perspective view of the module showing an e-beam unit mounted within the module for sterilizing selected surfaces of the vial and needles located within the module chamber, and with the needle manifold and other parts removed for clarity.
Figure 43:
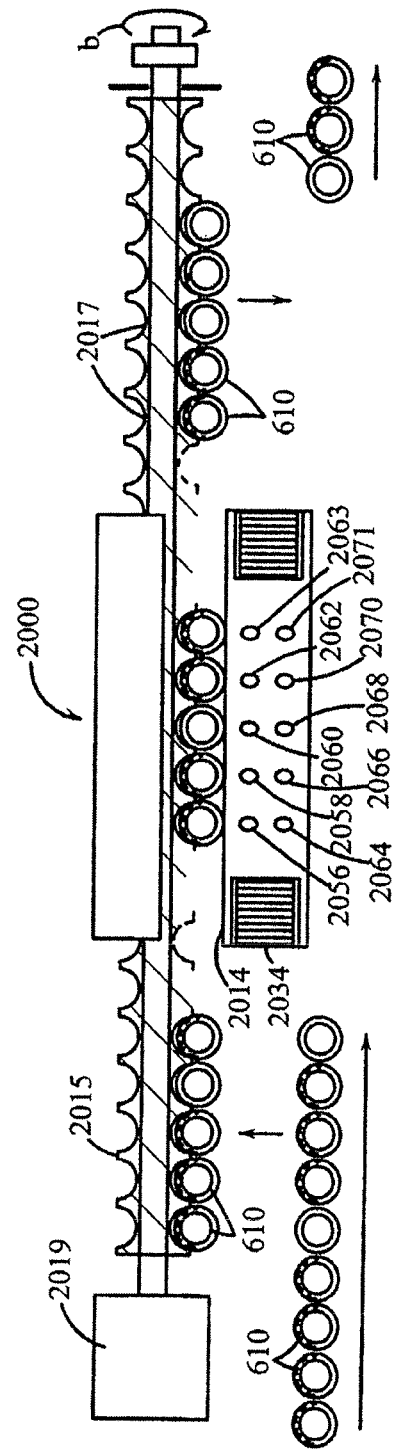
FIG. 43 is a top plan, somewhat schematic view of the module mounted adjacent to a screw-type conveyor for driving the vials through the module.

The module 2000 further includes a laser sealing and infrared (IR) sense manifold 2054 that is radially spaced adjacent to the needle manifold 2036 for laser sealing the pierced stoppers immediately following needle filling and withdrawal of the needles therefrom. As shown typically in FIG. 42, the laser sealing and infrared (IR) sense manifold 2054 holds a plurality of laser optics assemblies (e.g., five laser optic assemblies 2056, 2058, 2060, 2062 and 2063), along with a plurality of IR sensors (e.g., five IR sensors 2064, 2066, 2068, 2070 and 2071). Note that although only four laser optic assemblies and associated IR sensors are shown in FIG. 42 for simplicity, five laser optic assemblies and associated IR sensors are shown in FIG. 43. The laser optic assemblies are adapted to provide a laser beam to reseal the resealable stoppers on the vials after needle filling. Each of the plurality of laser optic assemblies is mounted at a respective location adjacent to the guide 2010 for transmitting a respective laser beam onto the resealable stopper of a respective vial 610 to heat seal the needle aperture in the resealable stopper. In addition, each laser optic assembly is aligned with a respective needle 2018 on the needle manifold 2016 to seal the location of the resealable stopper pierced by the respective needle. Each of the laser optic assemblies 2056-2063 is connected to a respective fiber optic cable that connects the respective optic assembly to a respective laser source (not shown). As can be seen, providing multiple fiber optic assemblies makes it possible to reseal multiple vials concurrently. In this embodiment, each of the plurality of IR sensor assemblies 2064-2071 is mounted adjacent to, and aligned with a respective laser optic assembly and needle 2018 on the needle manifold 2016. Preferably, the laser sources (not shown) are mounted outside of the sterile enclosure of the needle filling machine within which the module 2000 is mounted to enable repair and/or replacement of the laser sources without having to open the enclosure and/or otherwise risk contamination of the sterile enclosure. The IR sensors 2064-2071 detect the temperature of the needle penetration region of the resealable stopper achieved during laser resealing, and therefore can be used to determine whether the stopper was sufficiently reheated to achieve resealing. Each of the IR sensors 2064-2071 is connected to a respective IR sensor module (not shown). Providing multiple IR sensors enables the sterile filling machine to sense the temperature of multiple vials concurrently, for example, as they are being resealed.

As described above, each laser source transmits a predetermined wavelength of laser radiation at about 980 nm, and the predetermined power of each laser is preferably less than about 30 Watts, and preferably less than or equal to about 10 Watts, or within the range of about 8 to about 10 Watts. In the illustrated embodiment, each laser source is a semiconductor diode laser that outputs at about 15 Watts, and is fiber-optically coupled through a fiber-optic cable to a collimating lens of the respective laser optic assembly. If desired, the module 2000 can be enclosed, or partially enclosed within a tinted enclosure (not shown) including a plurality of tinted glass or translucent or transparent plastic panels that surround the laser optic assemblies on four sides to filter out potentially harmful radiation generated by the laser beams. In addition, capacitor sensors (not shown) may be provided downstream of the module 2000 in order to sense whether each vial received the medicament or other substance to be contained therein and to reject the vial if defective.

In the operation of the module 2000, the drive motor 2019 is rotatably driven in the direction of the arrow "b" to rotate the lead screw 2015 and, in turn, transport the vials 610 along the guide 2012 in the manner illustrated, for example, in FIG. 43. In the exemplary module of FIG. 43, the module includes five needles, five laser optic assemblies and five IR sensors, thus permitting the needle filling and laser resealing of five vials at one time. Accordingly, the lead screw 2015 is indexed five positions and then paused for a momentary dwell. As may be recognized by those or ordinary skill in the pertinent art based on the teachings herein, the module 2000 may include any desired number of needles, laser optic assemblies, and/or sensors. In addition, if desired, the lasers and sensors may be mounted within the module downstream of the needle manifold, to allow simultaneous filling and sealing of different vials, and thereby possibly increase the overall throughput of the module. During the dwell, the needle manifold 2016 is driven downward so as to drive the needles 2018 through the resealable stoppers on the vials beneath the needle manifold. Medicament or other substance is thereafter delivered by the pumps (not shown) through the needles and into the interior chambers of the vials, and the manifold is then driven up to thereby retract the needles 2018 from the stoppers. In one embodiment, the needles are initially withdrawn at a relatively slow speed to allow the vials to fill "bottom-up"; then, when the vials are filled, the needles are withdrawn at a relatively faster speed to quickly remove the needles and decrease overall cycle time. As can be seen, the diabolo or spool-like shape of the vials facilitates the ability to transport the vials in the conveying system, and further, the diabolo shape supports the vials and prevents axial movement of the vials during insertion and withdrawal of the needles during filling. The mid-portion of each vial is secured within the aperture 2014 of the guide 2010, the relatively larger diameter upper portion of each vial prevents axial downward movement of the vial upon inserting the needle into the resealable stopper of the vial by engaging the upper surface of the guide, and the relatively larger diameter base portion of the vial prevents upward axial movement of the vial upon withdrawal of the needle from the resealable stopper by engaging the underside of the guide.

Also during the dwell, and following withdrawal of the needles from the resealable stoppers, the laser optic assemblies 2056-2063 deliver laser energy to the resealable stoppers on the vials to reseal the stoppers. As the resealable stoppers are heated by the laser energy, the IR sensors 2064-2071 detect the temperature of each stopper, so as to be able to determine whether each stopper was heated sufficient to cause resealing. After the dwell, the process is repeated, i.e., the lead screw indexes another five positions and then dwells again so that the next five vials can be filled and resealed.

Figure 44:
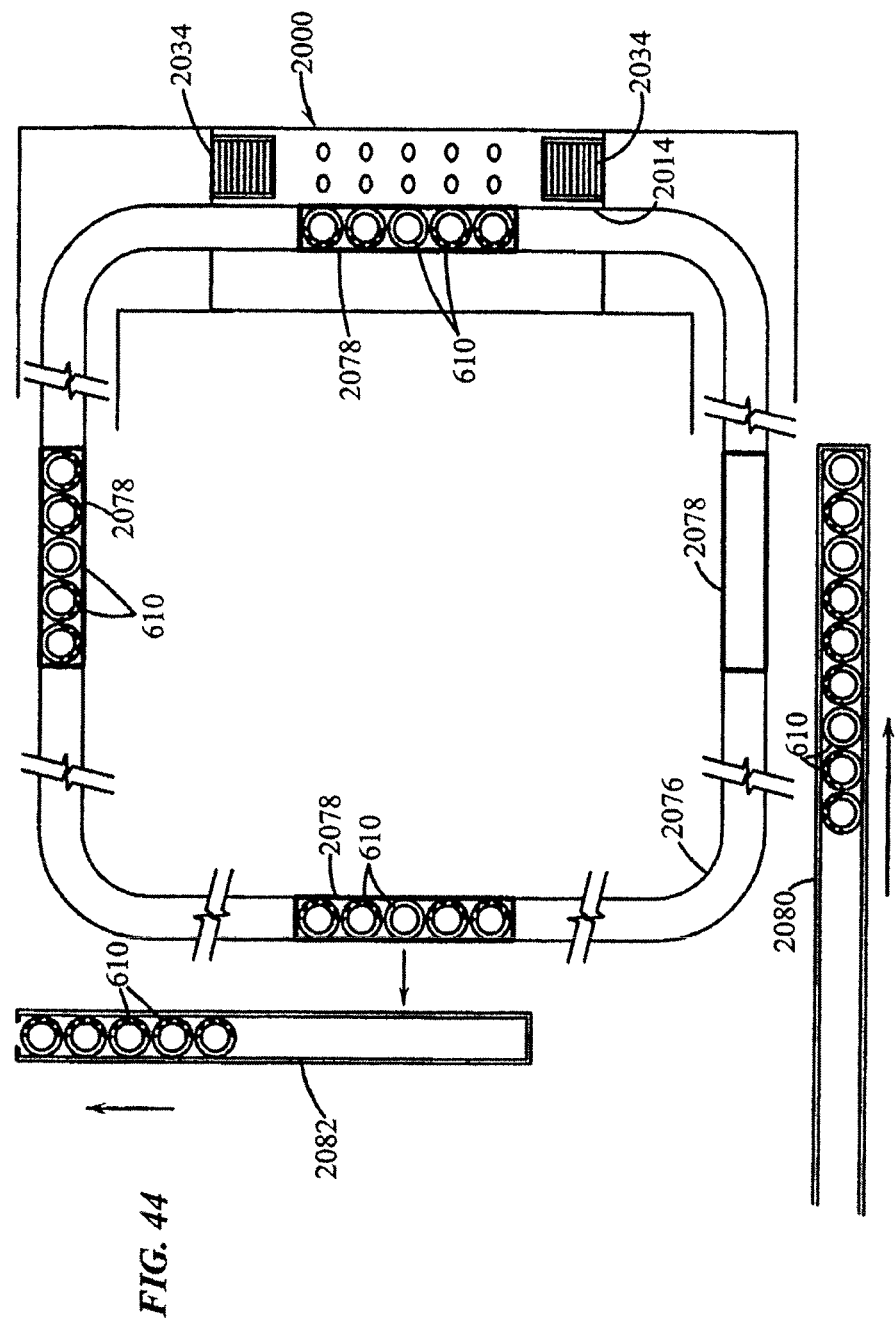
FIG. 44 is a top plan, somewhat schematic view of the module mounted adjacent to a closed-loop conveyor, an inlet conveyor for transferring the empty vials onto the closed loop conveyor, and an outlet conveyor for receiving the filled and resealed vials.

As shown in FIG. 44, the module 2000 may be mounted in a sterile enclosure wherein the transport system includes an endless conveyor 2076 and carriers 2078 mounted on the endless conveyor 2076 for transporting the vials 610 through the module 2000. An infeed conveyor 2080 feeds the sealed, empty vials onto the carriers 2078 of the endless conveyor 2076. Then, the endless conveyor 2076 feeds the vials through the module 2000 in the same manner, or in a manner similar to that described above. After the vials are filled and resealed in the module 2000, they are dispensed onto an outlet conveyor 2082. As may be recognized by those of ordinary skill in the pertinent art based on the teachings herein, the conveyers 2076, 2080 and 2082 and/or the components thereof may take the form of any of numerous different conveyors or conveyor components that are currently, or later become known for performing the functions of one or more of these conveyors or conveyor components.

As shown in FIG. 42, the module 2002 further includes an axially elongated port 2084 located on an opposite side of the needle manifold 2016 relative to the laser optic assemblies and sensors for mounting therein an e-beam unit 2086 that transmits an e-beam into the axially-elongated chamber 2088 of the module and, in turn, sterilizes the surfaces of the vial and the needle surfaces within the chamber. The e-beam assembly, including the e-beam source, the chamber for containing the e-beam, and the conveyor for conveying the vials through the e-beam chamber, may be the same as, or similar to that disclosed in co-pending U.S. patent application Ser. No. 10/600,525, filed Jun. 19, 2003, entitled "STERILE FILLING MACHINE HAVING NEEDLE FILLING STATION WITHIN E-BEAM CHAMBER," and U.S. Provisional Patent Application Ser. No. 60/390,212, entitled "STERILE FILLING MACHINE HAVING NEEDLE FILLING STATION WITHIN E-BEAM CHAMBER," filed Jun. 19, 2002, each of which is hereby expressly incorporated by reference as part of the present disclosure. As described in these co-pending patent applications, the e-beam unit may be any of numerous different types of e-beam units or sources that are currently, or later become known, for performing the function of the e-beam unit described herein.

E-beam radiation is a form of ionizing energy that is generally characterized by its low penetration and high dose rates. The electrons alter various chemical and molecular bonds upon contact with an exposed product, including the reproductive cells of microorganisms, and therefore e-beam radiation is particularly suitable for sterilizing vials and other containers for medicaments or other sterile substances. An e-beam source produces an electron beam that is formed by a concentrated, highly charged stream of electrons generated by the acceleration and conversion of electricity. Preferably, the electron beam is focused onto a penetrable surface of each vial for piercing by the respective needle. For example, in one embodiment, the electron beam is focused onto the upper surface of the resealable stopper to sterilize the penetrable surface of the stopper prior to insertion of the filling needle therethrough. In addition, reflective surfaces may be mounted on opposite sides of the conveyor relative to each other to reflect the e-beam, and/or the reflected and scattered electrons, onto the sides of the vials to facilitate sterilization of these surfaces of the vial, if necessary. Alternatively, or in combination with such reflective surfaces, more than one e-beam source may be employed, wherein each e-beam source is focused onto a respective surface or surface portion of the vials or other containers to ensure sterilization of each surface area of interest. In some embodiments, the current, scan width, position and energy of the e-beam, the speed of the transport system, and/or the orientation and position of any reflective surfaces, are selected to achieve at least about a 3 log reduction, and preferably about a 6 log reduction in bioburden testing on the upper surface of the vial's resealable stopper, i.e., the surface of the stopper defining the penetrable region that is pierced by a respective filling needle to fill the vial. In addition, as an added measure of caution, one or more of the foregoing variables also are preferably selected to achieve at least about a 3 log reduction on the sides of the vial, i.e., on the surfaces of the vial that are not pierced by the needle during filling. In addition, the e-beam may be directed onto the needles prior to entry through the resealable stoppers, or at least the portions of the needles that contact the stoppers, to further ensure sterilization of the needles and vials. These specific levels of sterility are only exemplary, however, and the sterility levels may be set as desired or otherwise required to validate a particular product under, for example, United States FDA or applicable European standards, such as the applicable Sterility Assurance Levels ("SAL").

Figure 45:
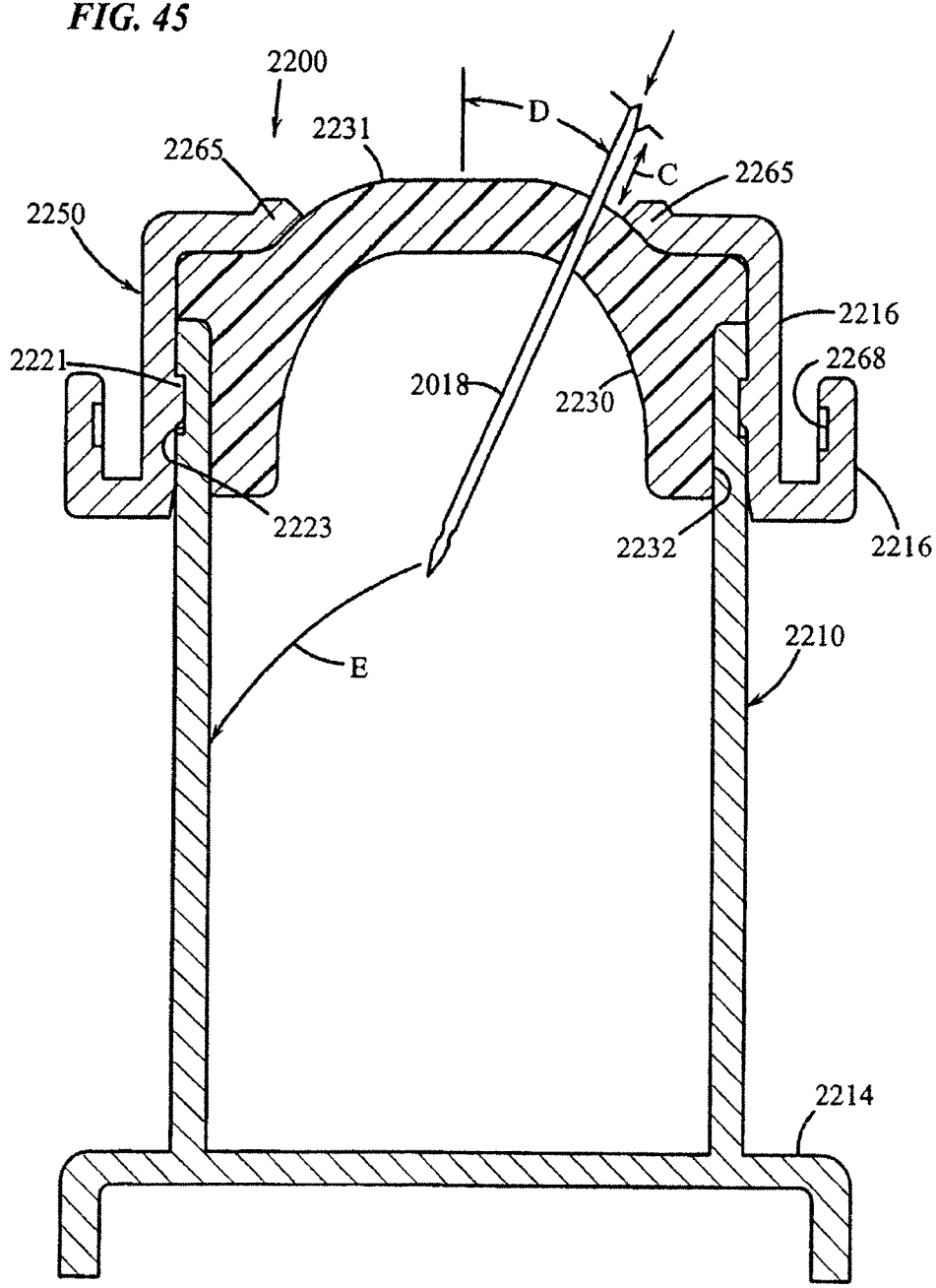
FIG. 45 is a cross-sectional view of another vial embodying the present disclosure wherein the filling needle may penetrate the stopper in a marginal portion of the penetrable region of the stopper at an acute angle relative to the axis of the vial, and the resealed portion of the stopper may be concealed under the tamper-resistant cover upon removing the frangible portion thereof.

Turning to FIGS. 45-48, another vial embodying the present invention is indicated generally by the reference numeral 2200. The vial 2200 is similar in many respects to the vial 900 described above with reference to FIGS. 29-31, and therefore like reference numerals preceded by the numeral "22" instead of the numeral "9" are used to indicate like elements. With reference to FIG. 45, a primary difference of the vial 2200 in comparison to the vial 900 described above is that the frusto-conical or innermost edge 2265 of the locking ring 2250 is spaced relatively inwardly to, in turn, permit a filling needle 2018 to pierce the resealable stopper 2230 at an acute angle "D" relative to the axis of the vial and in a peripheral portion of the penetrable region 2231 of the stopper. One advantage of this configuration is that, as shown in FIG. 47, the penetrated and laser (or otherwise thermally) resealed portion 2231 of the stopper is located on a marginal or peripheral portion of the region 2231 of the stopper, and thus can be concealed under an inner edge 2233 of the tamper-resistant cover 2240 when the frangible portion 2260 of the tamper-resistant cover is removed in use, as described further below.

As can be seen, the locking ring 2250 defines a peripheral flange forming the neck 2216 and further defines on its interior edge an annular recess 2268 for receiving therein an annular protuberance 2266 formed on the tamper-resistant cover 2250. The interior edge of the annular flange 2216 leading into the recess 2268 may define a chamfered surface, and the leading edge of the annular protuberance 2266 of the cover also may be chamfered to allow the protuberance to be snapped into, or otherwise fixedly received within the recess, but to prevent removal of the cover therefrom. Similarly, the locking ring 2250 defines on its inner diameter an annular protuberance 2221 that is snapped into, or otherwise fixedly received within a corresponding annular recess 2223 formed on the exterior of the vial body 2210 to fixedly secure the locking ring 2250 to the vial body. In this embodiment, the base 2214 of the vial body 2210 is formed integral with the remainder of the vial body in order to reduce the number of parts; however, if desired, the base 2214 can be made as a separate part that is snap-fit or otherwise attached to the vial body.

As shown in FIGS. 47 and 48, the tamper-resistant cover 2240 defines a centrally-located frangible portion 2260, and an inwardly depending annular protuberance 2263 that engages the exposed surface of the stopper 2230 and, if desired, may form a hermetic or gas-tight seal therebetween. As shown in FIGS. 47 and 48, a plurality of frangible connections 2262 are angularly spaced relative to each other and extend between the frangible portion 2260 and a substantially dome-shaped cover body 2241 to allow removal of the frangible portion and access to the underlying stopper 2230. The frangible portion 2260 of the cover is pressed downwardly by, for example, a user's finger, to slightly depress the underlying stopper material and, in turn, break the frangible connections 2262. Once removed, the frangible portion 2260 cannot be reconnected to thereby provide a tamper-proof feature. The tamper-resistant cover 2240 further includes a second downwardly depending protuberance 2235 located adjacent to the first protuberance 2263 and in engagement with the exposed stopper to form a hermetic or gas-tight seal therebetween. If desired, the first and second annular protuberances 2263 and 2235, respectively, may be formed contiguous with each other to, in turn, form a gas-tight or hermetic seal therebetween, and thereby increase the MVT barrier of the vial in the direction through the stopper.

As indicated in FIG. 45, the vial 2200 may be filled in, for example, a needle filling and laser resealing module as described above. However, one difference enabled by the vial 2200 is that the needle 2018 is inserted into the penetrable region 2231 of the resealable stopper 2230 at an acute angle "D" relative to the axis of the vial, and in a marginal or outer peripheral portion of the penetrable region adjacent to the inner edge 2265 of the locking ring 2250. As can be seen in comparison to the locking ring 950 described above in connection with FIG. 29, the inner edge 2265 of the locking ring 2250 is spaced radially outwardly to, in turn, expose the marginal portion of the penetrable region 2231 of the stopper and permit same to be penetrated by the needle 2018 at the acute angle "D". One advantage of penetrating the stopper 2230 with the needle 2018 at the acute angle D, is that the fluid injected by the needle is directed onto the side wall of the vial body 2210 substantially at the acute angle, as indicated by the arrow "E" in FIG. 45, and thus facilitates creating a laminar flow, or substantially laminar flow of fluid into the vial. This type of flow facilitates in preventing the formation of bubbles or like turbulent effects upon filling the vial with fluid, and thus permits the vials to be filled more quickly and/or otherwise in a more desirable manner. As may be recognized by those of ordinary skill in the pertinent art based on the teachings herein, the acute angle "D" may be created by orienting the needles on the needle manifold at an acute angle relative to the axis of the vial, or by orienting the axes of the vials in the filling station at an acute angle relative to the axes of the needles, or a combination of both. In the illustrated embodiment, the angle "D" is within the range of about 30° to about 45°; however, these angles are only exemplary, and may be changed as desired to obtain the desired flow and/or filling characteristics, or otherwise as desired to meet the requirements of a particular application.

Another advantage of this embodiment of the present invention is that the penetrated/resealed portion of the stopper may be visually concealed from the end user throughout the use of the vial. As shown typically in FIG. 47, the needle hole, and thus the resealed portion 2231 of the stopper, is concealed under the inner edge portion 2233 of the tamper-resistant cover 2240. Accordingly, upon removing the frangible portion 2260 of the tamper-resistant cover 2240 to access with a syringe the contents of the vial, the underlying and visually exposed portion of the stopper 2230 does not include the resealed portion 2231, and thus may be considered more aesthetically desirable or pleasing than having the resealed portion visually exposed.

As may be recognized by those skilled in the pertinent art based on the teachings herein, numerous changes and modifications may be made to the above-described and other embodiments of the present application without departing from the inventive aspects disclosed herein. For example, the resealable portion may be integrally molded with a base such as by insert molding, the resealable portion may be fused or otherwise melted to a base, or the resealable portion may be sequentially molded to a base. Alternatively, the resealable stopper may be formed of only one material, i.e., the resealable portion with the infusible base or other infusible layer, may be formed with multiple layers, wherein some or all of the layers are thermally resealable. Thus, the resealable stopper may be made of any of numerous different materials which are currently known, or later become known for performing the functions of the resealable portion or stopper described herein, such as any of numerous different thermoplastic and/or elastomeric materials. In addition, the vials may be made of any of numerous different materials that are currently or later become known for forming vials, such as medicament vials, including any of numerous different types of glass or plastic, or combinations of glass and plastic. For example, the vial body can be formed of glass, and the base, locking ring and/or tamper-resistant cover can be formed of plastic, and can be joined to the body or to each other in accordance with any of numerous different joining mechanisms that are currently, or later become known, such as by over-molding, mechanical snap-fit or other interlocking engagements, by adhesively joining glass to plastic, or by ultrasonically welding or otherwise welding plastic to plastic. In addition, the needles used to fill the vials may take the form of any of the needles disclosed in British patent application no. GB 0308705.2, filed Apr. 28, 2003, entitled "Novel Device," the vial closure may take any of the forms of the closures disclosed in British patent application no. GB0304268.6, filed Feb. 26, 2003, entitled "Novel Device," the conveyor system and/or the components thereof may take any of the forms as shown in British patent application no. GB0221510.1, filed Sep. 17, 2002, entitled "Novel Device," and the needle filling and/or processing stations may take any of the forms shown in British patent application no. GB0221511.9, filed Sep. 17, 2002, entitled "Novel Device," each of which is hereby expressly incorporated by reference in its entirety as part of the present disclosure. Accordingly, this detailed description of the preferred embodiments is to be taken in an illustrative, as opposed to a limiting sense.

What is claimed is:

1. A method comprising the following steps:
filling a sealed, empty device defining a chamber sealed with respect to ambient atmosphere and a penetrable portion in fluid communication with the chamber, wherein the filling step comprises:
penetrating the penetrable portion with a filling or injection member coupled in fluid communication with a source of a substance;
introducing the substance through the filling or injection member and into the chamber of the device;
withdrawing the filling or injection member from the penetrable portion; and
covering the penetrated portion with a covering portion such that the covering portion is attached to the device and engaging the covering portion against the penetrable portion one or more of (a) at the penetration aperture; (b) contiguous to the penetration aperture; or (c) directly adjacent to the penetration aperture around an entirety of the penetration aperture, and thereby one or more of (i) hermetically sealing the penetrated portion from the ambient atmosphere; (ii) hermetically sealing the substance within the chamber; or (iii) forming a gas-tight seal between the ambient atmosphere and the chamber.

2. A method as defined in claim 1, wherein the penetrable portion is defined by an elastomeric portion sufficiently resilient to close upon itself after withdrawal of the filling or injection member to thereby maintain the device in a sealed condition between the withdrawing and covering steps.

3. A method as defined in claim 1, further comprising the step of introducing substance through a first fluid passageway of the filling or injection member, and allowing fluid to flow out of the chamber of the device through a second fluid passageway upon introducing substance from the first fluid passageway into the chamber.

4. A method as defined in claim 1, wherein the filling or injection member comprises a needle.

5. A method as defined in claim 1, wherein the device is a vial and the penetrable portion is defined by a resealable stopper.

6. A method as defined in claim 1, wherein the substance comprises one or more of a liquid or a medicament.

7. A method as defined in claim 1, wherein the covering portion comprises one or more of (i) a cover; or (ii) a cover layer.

8. A method as defined in claim 1, wherein the penetrable portion is resealable by applying radiation or energy thereto, and further comprising the step of applying radiation or energy thereto.

9. A method as defined in claim 8, wherein the step of applying radiation or energy comprises applying laser radiation or energy.

10. A method as defined in claim 1, wherein the penetrable portion comprises a base portion comprising a first material compatible with the substance and defining a substance-exposed surface in fluid communication with the chamber, and further comprising the step of providing a resealing portion overlying the base portion comprising a second material that upon the transmitting of radiation or energy thereto one or more of (i) hermetically seals the penetrated portion from the ambient atmosphere; (ii) hermetically seals the substance within the chamber, or (iii) forms a gas-tight seal between the ambient atmosphere and the chamber.

11. A method as defined in claim 10, wherein the first material is substantially infusible by the radiation or energy.

12. A method as defined in claim 10, further comprising the step of transmitting radiation or energy to the resealing portion.

13. A method as defined in claim 10, wherein the step of transmitting radiation or energy comprises transmitting laser radiation or energy.

14. A method as defined in claim 1, wherein the covering step further comprises one or more of (i) compressing the penetrable portion or (ii) forming an interference fit with the penetrable portion.

15. A method as defined in claim 14, wherein the penetrable portion is defined by an elastomeric portion sufficiently resilient to close upon itself after withdrawal of the filling member to thereby maintain the device in a sealed condition prior to covering the penetrated portion with the covering portion.

16. A method as defined in claim 8, wherein the penetrable portion includes a body defining a predetermined wall thickness that substantially absorbs laser radiation or energy at a predetermined wavelength and power and substantially prevents the passage of the radiation or energy therethrough, and a penetrable region that is penetrable with the filling or injection member and that defines a predetermined color and opacity that substantially absorbs the laser radiation or energy at the predetermined wavelength and power to hermetically seal an aperture therein formed by the filling or injection member, and the method further comprises the following steps:
applying laser radiation or energy from a laser source at the predetermined wavelength and power to the penetrable region of the body;
substantially absorbing within the penetrable region of the body the laser radiation or energy at the predetermined wavelength and power and substantially preventing the passage of the radiation or energy through the predetermined wall thickness of the body; and
hermetically sealing the aperture in the penetrable region of the body with the laser radiation or energy within a predetermined time period.

17. A method as defined in claim 16, further comprising the step of using the body to insulate the substance in the chamber from the laser radiation or energy applied by the laser source to avoid damage to the substance in the chamber.

* * * * *